US009089501B2

(12) United States Patent
Altman et al.

(10) Patent No.: US 9,089,501 B2
(45) Date of Patent: *Jul. 28, 2015

(54) SERICIN EXTRACTED FABRICS

(71) Applicant: Allergan, Inc., Irvine, CA (US)

(72) Inventors: Gregory H. Altman, Arlington, MA (US); Rebecca Horan, Arlington, MA (US); David J. Horan, Westfield, MA (US); Jingsong Chen, Virginia Beach, VA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,712

(22) Filed: Dec. 20, 2013

(65) Prior Publication Data

US 2014/0105951 A1     Apr. 17, 2014

Related U.S. Application Data

(60) Continuation of application No. 13/561,808, filed on Jul. 30, 2012, now Pat. No. 8,623,398, which is a division of application No. 12/770,588, filed on Apr. 29, 2010, now abandoned, which is a continuation of application No. 10/800,134, filed on Mar. 11, 2004, now abandoned, which is a continuation-in-part of application No. 10/008,924, filed on Nov. 16, 2001, now Pat. No. 6,902,932.

(60) Provisional application No. 60/453,584, filed on Mar. 11, 2003.

(51) Int. Cl.
| | |
|---|---|
| A61F 2/00 | (2006.01) |
| A61F 2/08 | (2006.01) |
| A61K 9/70 | (2006.01) |
| A61K 38/17 | (2006.01) |
| A61L 27/22 | (2006.01) |
| A61L 27/36 | (2006.01) |
| A61L 27/38 | (2006.01) |
| A61L 27/48 | (2006.01) |
| C12N 5/077 | (2010.01) |
| C07K 14/435 | (2006.01) |
| A61K 35/12 | (2015.01) |

(52) U.S. Cl.
CPC . *A61K 9/70* (2013.01); *A61K 38/17* (2013.01); *A61L 27/227* (2013.01); *A61L 27/3608* (2013.01); *A61L 27/3662* (2013.01); *A61L 27/3804* (2013.01); *A61L 27/386* (2013.01); *A61L 27/3821* (2013.01); *A61L 27/3895* (2013.01); *A61L 27/48* (2013.01); *C07K 14/43518* (2013.01); *C12N 5/066* (2013.01); *A61F 2/00* (2013.01); *A61F 2/08* (2013.01); *A61K 35/12* (2013.01); *A61L 2430/10* (2013.01); *C12N 2533/50* (2013.01); *Y10T 428/298* (2015.01)

(58) Field of Classification Search
CPC ......... A61L 27/22; A61L 27/36; A61L 27/38; A61L 27/60; A61L 9/70; A61L 38/17; A61L 27/227; A61L 27/3608; A61L 27/3662; A61L 27/3804; A61L 27/3821; A61L 27/386; A61L 27/3895; A61L 27/48; C12N 5/00; C12N 5/08; C12N 5/066; A61K 9/70; A61K 38/17; C07K 14/3518
See application file for complete search history.

(56) References Cited

U.S. PATENT DOCUMENTS

| | | |
|---|---|---|
| 848,605 A | 3/1907 | Schmic |
| 1,709,662 A | 4/1929 | Ellis |
| 1,815,279 A | 7/1931 | Tkamine, Jr. |
| 1,828,736 A | 10/1931 | Harvey, Jr. |
| 1,896,494 A | 2/1933 | Myers et al. |
| 1,921,022 A | 9/1933 | Fink et al. |
| 1,990,588 A | 2/1935 | Bueno |
| 2,040,949 A | 5/1936 | Olpin et al. |
| 3,595,276 A | 7/1971 | Wrzesien |
| 4,118,842 A | 10/1978 | Norris et al. |
| 4,141,207 A | 2/1979 | Mizushima et al. |
| 4,792,336 A | 12/1988 | Hlavacek et al. |
| 4,865,031 A | 9/1989 | O'Keefe |
| 4,942,875 A | 7/1990 | Hlavacek et al. |

(Continued)

FOREIGN PATENT DOCUMENTS

| | | |
|---|---|---|
| EP | 0889156 | 12/1996 |
| EP | 1241178 | 9/2002 |

(Continued)

OTHER PUBLICATIONS

Goes et al. The Surgery of the Breast, Principles and Art, Lippincott Williams & Wilkins, 2nd Edition, Chapter 52, pp. 786-793, 2006.
Minoura et al. Journal of Biomedical Materials Research 29(10):1215-1221, 1995.
Sofia et al. Journal of Biomedical Materials Research 54(1):139-148, 2001.
Altman et al., Silk based biomaterials, Biomaterials (2003) 24:401-416.
Cappello et al., In-situ self-assembling protein polymer gel systems for administration, delivery, and release of drugs, USA Journal of controlled release: official journal of the Controlled Release Society (Apr. 30, 1998), 53 (1-3):105-17, San Diego, CA 92121.

(Continued)

*Primary Examiner* — Blaine Lankford
*Assistant Examiner* — Charles Zoltan Constantine
(74) *Attorney, Agent, or Firm* — Linda Allyson Nassif

(57) ABSTRACT

Silk is purified to eliminate immunogenic components (particularly sericin) and is used to form fabric that is used to form tissue-supporting prosthetic devices for implantation. The fabrics can carry functional groups, drugs, and other biological reagents. Applications include hernia repair, tissue wall reconstruction, and organ support, such as bladder slings. The silk fibers are arranged in parallel and, optionally, intertwined (e.g., twisted) to form a construct; sericin may be extracted at any point during the formation of the fabric, leaving a construct of silk fibroin fibers having excellent tensile strength and other mechanical properties.

6 Claims, 23 Drawing Sheets

(56) References Cited

U.S. PATENT DOCUMENTS

| | | | |
|---|---|---|---|
| 5,120,829 A | 6/1992 | Pierschbacher et al. |
| 5,171,505 A | 12/1992 | Lock |
| 5,250,077 A | 10/1993 | Fuse et al. |
| 5,252,285 A | 10/1993 | Lock |
| 5,385,836 A | 1/1995 | Kimura et al. |
| 5,456,697 A | 10/1995 | Chesterfield et al. |
| 5,569,273 A | 10/1996 | Titone et al. |
| 5,587,456 A | 12/1996 | Pierschbacher et al. |
| 5,591,822 A | 1/1997 | Pierschbacher et al. |
| 5,598,615 A | 2/1997 | Takada |
| 5,606,019 A | 2/1997 | Cappello |
| 5,643,043 A | 7/1997 | Pflum |
| 5,700,559 A | 12/1997 | Sheu et al. |
| 5,736,399 A | 4/1998 | Takezawa et al. |
| 5,760,176 A | 6/1998 | Pierschbacher et al. |
| 5,771,716 A | 6/1998 | Schlussel |
| 5,849,040 A | 12/1998 | Kanehisa |
| 5,919,232 A | 7/1999 | Chaffringeon et al. |
| 5,951,506 A | 9/1999 | Tsubouchi |
| 5,990,378 A | 11/1999 | Ellis |
| 5,994,099 A | 11/1999 | Lewis et al. |
| 6,042,592 A | 3/2000 | Schmitt |
| 6,080,689 A | 6/2000 | Kanehisa |
| 6,090,116 A | 7/2000 | D'Aversa et al. |
| 6,110,590 A | 8/2000 | Zarkoob et al. |
| 6,136,022 A | 10/2000 | Nunez et al. |
| 6,146,418 A | 11/2000 | Berman |
| 6,175,053 B1 | 1/2001 | Tsubouchi |
| 6,228,132 B1 | 5/2001 | Prince et al. |
| 6,287,316 B1 | 9/2001 | Agarwal et al. |
| 6,287,340 B1 | 9/2001 | Altman et al. |
| 6,302,922 B1 | 10/2001 | Kanehisa |
| 6,303,136 B1 | 10/2001 | Li et al. |
| 6,408,656 B1 | 6/2002 | Ory et al. |
| 6,427,933 B1 | 8/2002 | Tsubouchi |
| 6,440,740 B1 | 8/2002 | Tsubouchi et al. |
| 6,443,964 B1 | 9/2002 | Ory et al. |
| 6,506,394 B1 | 1/2003 | Yahiaoui et al. |
| 6,544,287 B1 | 4/2003 | Johnson et al. |
| 6,627,422 B1 | 9/2003 | Li et al. |
| 6,638,284 B1 | 10/2003 | Rousseau et al. |
| 6,645,041 B2 | 11/2003 | Sorensen |
| 6,729,356 B1 | 5/2004 | Baker et al. |
| 6,730,016 B1 | 5/2004 | Cox et al. |
| 6,737,371 B1 | 5/2004 | Planck et al. |
| 6,773,459 B2 | 8/2004 | Dauner et al. |
| 6,783,554 B2 | 8/2004 | Amara et al. |
| 6,827,743 B2 | 12/2004 | Eisermann et al. |
| 6,848,281 B2 | 2/2005 | Ishihara et al. |
| 6,866,681 B2 | 3/2005 | Laboureau et al. |
| 6,902,932 B2 | 6/2005 | Altman et al. |
| 6,946,003 B1 | 9/2005 | Wolowacz et al. |
| 6,966,918 B1 | 11/2005 | Schuldt-Hempe et al. |
| 6,971,252 B2 | 12/2005 | Therin et al. |
| 7,021,086 B2 | 4/2006 | Ory et al. |
| 7,115,388 B2 | 10/2006 | Tsubouchi |
| 7,156,858 B2 | 1/2007 | Schuldt-Hempe et al. |
| 7,166,570 B2 | 1/2007 | Hunter et al. |
| 7,285,637 B2 | 10/2007 | Armato et al. |
| 7,293,433 B1 | 11/2007 | McMurray |
| 7,338,531 B2 | 3/2008 | Ellis et al. |
| 7,341,601 B2 | 3/2008 | Eisermann et al. |
| 7,429,206 B2 | 9/2008 | Perry |
| 7,476,249 B2 | 1/2009 | Frank |
| 7,614,258 B2 | 11/2009 | Cherok et al. |
| 7,824,701 B2 | 11/2010 | Binette et al. |
| 7,828,855 B2 | 11/2010 | Ellis et al. |
| 7,842,098 B2 | 11/2010 | Kaplan et al. |
| 7,875,074 B2 | 1/2011 | Chen et al. |
| 7,900,484 B2 | 3/2011 | Cherok et al. |
| 8,007,531 B2 | 8/2011 | Frank |
| 8,197,542 B2 | 6/2012 | Becker |
| 8,202,317 B2 | 6/2012 | Becker |
| 2002/0156437 A1 | 10/2002 | McDevitt et al. |
| 2003/0087433 A1 | 5/2003 | Tsubouchi et al. |
| 2003/0165548 A1 | 9/2003 | Tsubouchi et al. |
| 2003/0183978 A1 | 10/2003 | Asakura |
| 2004/0005363 A1 | 1/2004 | Tsukada et al. |
| 2004/0170827 A1 | 9/2004 | Crighton |
| 2004/0219630 A1 | 11/2004 | Tsubouchi |
| 2004/0224406 A1 | 11/2004 | Altman et al. |
| 2005/0089552 A1 | 4/2005 | Altman et al. |
| 2005/0260706 A1 | 11/2005 | Kaplan et al. |
| 2006/0030939 A1 | 2/2006 | Frank |
| 2007/0088434 A1 | 4/2007 | Frank et al. |
| 2008/0038236 A1 | 2/2008 | Gimble et al. |
| 2008/0131509 A1 | 6/2008 | Hossainy et al. |
| 2008/0176960 A1 | 7/2008 | Tsukada et al. |
| 2008/0206302 A1 | 8/2008 | Sittinger et al. |
| 2008/0300683 A1 | 12/2008 | Altman et al. |
| 2009/0024162 A1 | 1/2009 | Shalaby et al. |
| 2009/0030454 A1 | 1/2009 | Knight et al. |
| 2009/0214649 A1 | 8/2009 | Gazit et al. |
| 2010/0023029 A1 | 1/2010 | Young et al. |
| 2010/0145367 A1 | 6/2010 | Ratcliffe |
| 2010/0209405 A1 | 8/2010 | Altman et al. |
| 2010/0249924 A1 | 9/2010 | Powell et al. |
| 2010/0256756 A1 | 10/2010 | Altman et al. |
| 2011/0009960 A1 | 1/2011 | Altman et al. |
| 2011/0022171 A1 | 1/2011 | Richter et al. |
| 2011/0054604 A1 | 3/2011 | Becker et al. |
| 2011/0054605 A1 | 3/2011 | Becker et al. |
| 2011/0106249 A1 | 5/2011 | Becker et al. |
| 2011/0167602 A1 | 7/2011 | Altman et al. |
| 2011/0171453 A1 | 7/2011 | Altman et al. |
| 2011/0184227 A1 | 7/2011 | Altman et al. |
| 2011/0189773 A1 | 8/2011 | Altman et al. |
| 2011/0190795 A1 | 8/2011 | Hotter et al. |
| 2011/0224703 A1 | 9/2011 | Mortarino et al. |
| 2011/0257665 A1 | 10/2011 | Mortarino et al. |
| 2011/0257761 A1 | 10/2011 | Mortarino et al. |
| 2011/0282365 A1 | 11/2011 | Hadba et al. |
| 2011/0301717 A1 | 12/2011 | Becker |
| 2012/0053690 A1 | 3/2012 | Frank |
| 2012/0165957 A1 | 6/2012 | Everland et al. |
| 2012/0184974 A1 | 7/2012 | Becker |
| 2012/0226352 A1 | 9/2012 | Becker |
| 2012/0244143 A1 | 9/2012 | Lo et al. |

FOREIGN PATENT DOCUMENTS

| | | |
|---|---|---|
| EP | 2210971 | 7/2010 |
| EP | 2068766 | 10/2011 |
| JP | 06-245989 | 9/1994 |
| WO | 0072782 | 12/2000 |
| WO | 0229141 | 4/2002 |
| WO | 2004062697 | 7/2004 |
| WO | 2004080346 | 9/2004 |
| WO | 2005123114 | 12/2005 |
| WO | 2006102477 | 9/2006 |
| WO | 2008016919 | 2/2008 |
| WO | 2008042992 | 4/2008 |
| WO | 2008116127 | 9/2008 |
| WO | 2009023615 | 2/2009 |
| WO | 2010074827 | 7/2010 |
| WO | 2010141133 | 12/2010 |
| WO | 2011031854 | 3/2011 |

OTHER PUBLICATIONS

Horan et al., In vitro degradation of silk fibroin, USA Biomaterials (Jun. 2005), 26(17):3385-93.

Horan, et al., Biological and biomechanical assessment of a long-term bioresorbable silk-derived surgical mesh in an abdominal body wall defect model, Hernia (2009) 13(2):189-99.

Kardestuncer et al., RGD-tethered silk substrate stimulates the differentiation of human tendon cells, Clinical Orthopaedics and Related Research (2006), No. 448:pp. 234-239.

Kundu et al., Natural protective glue protein, sericin bioengineered by silkworms: Potential for biomedical and biotechnological applications, Progress in Polymer Science (2008) 33:998-1012.

Panilaitis et al., Macrophage responses to silk, Biomaterials (2003) 24(18):3079-3085.

(56) References Cited

OTHER PUBLICATIONS

Tamada, Y., Symposium Preprints, The Society of Fiber Science and Technology (1998) p. S-51.

Tsukada, Preparation and application of porous silk fibroin materials, Journal of Applied Polymer Science (1994).

Yanagisawa et al., Improving cell-adhesive properties of recombinant *Bombyx mori* silk by incorporation of collagen or fibronectin derived peptides produced by transgenic silkworms, Biomacromolecules (2007), 8 (11):3487-3492.

Zhu et al., Preparation and Characterization of Regenerated *Bombyx mori* silk fibroin fiber containing recombinant cell-adhesive proteins; nonwoven fiber and monofilament, Journal of Applied Polymer Science (2008), vol. 109:2956-2963.

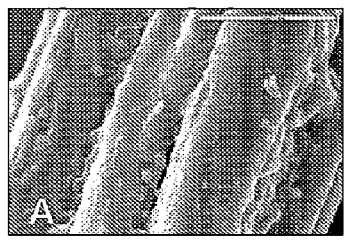 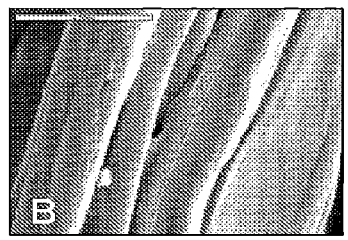 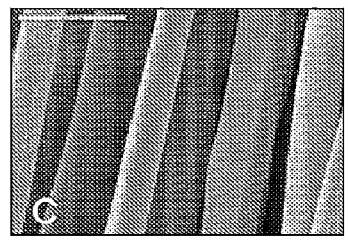
*FIG. 1A*     *FIG. 1B*     *FIG. 1C*
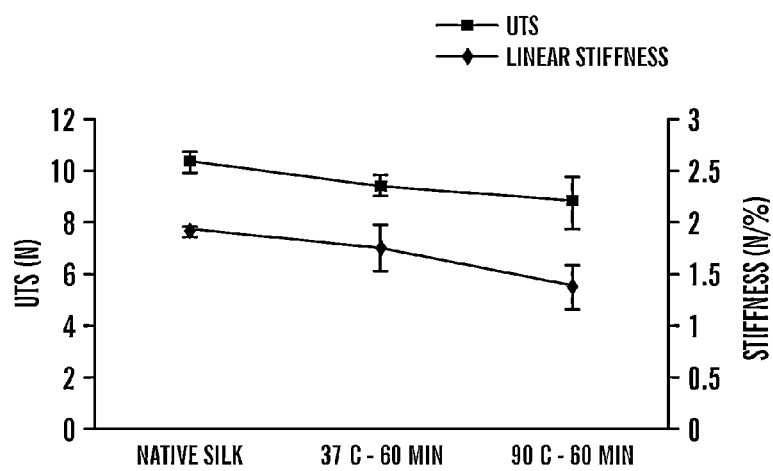
*FIG. 1D*

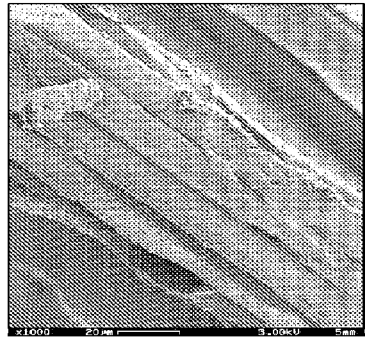 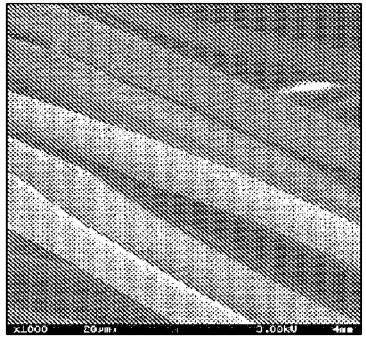 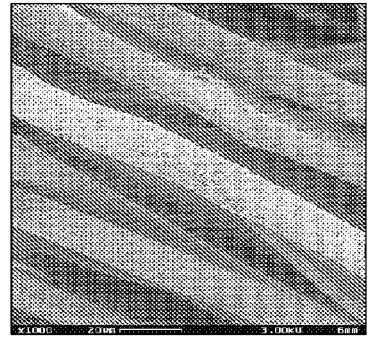
RAW SILK
FIG. 1E
1x WASHED SILK
FIG. 1F
2x WASHED SILK
FIG. 1G
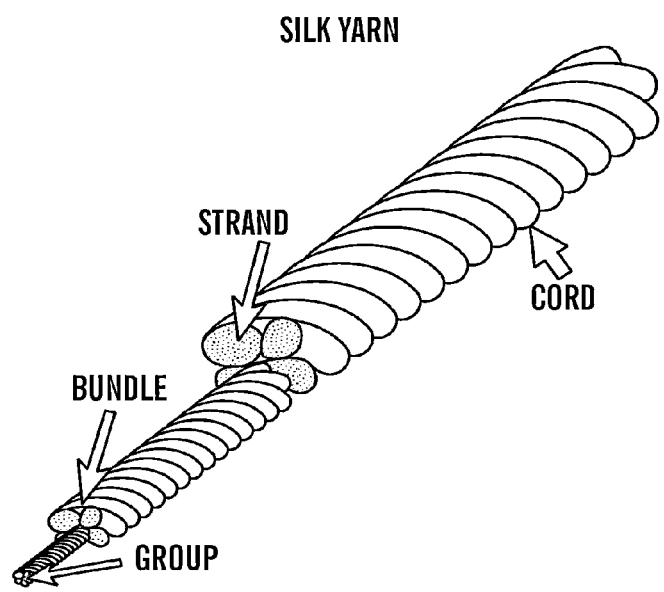
FIG. 2A

(ALL DONE ON 12(0) x 3(8), EXTRACTED AND WET)

| STRAIN RATE (mm/min) | UTS (N) | stdev (N) | STIFFNESS (N/mm) | stdev (N/mm) |
|---|---|---|---|---|
| 3050 | 24.9 | 0.60 | 3.70 | 1.04 |
| 2700 | 25.0 | 0.86 | 3.47 | 0.40 |
| 900 | 24.3 | 0.50 | 3.02 | 0.12 |
| 36 | 22.5 | 0.70 | 2.74 | 0.08 |

| SURFACE TREATMENT | SILK CROSS-SECTIONAL AREA (mm$^2$) | | CHANGE FROM DAY 10 TO DAY 90 (%) |
|---|---|---|---|
| | 10 DAYS | 90 DAYS | |
| NON-TREATED | 0.000118 | 0.000115 | 2.5 |
| N$_2$ PLASMA | 0.000129 | 0.000096 | 25.6 |
| RGD | 0.000129 | 0.000082 | 36.4 |

*FIG. 13E*

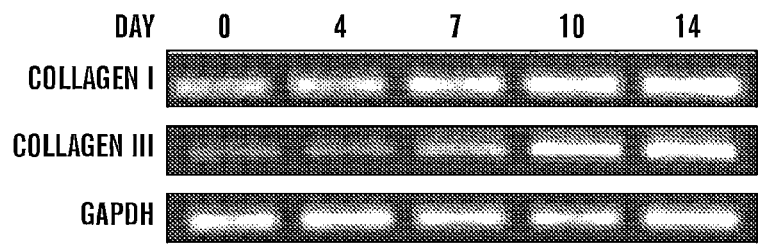
FIG. 14
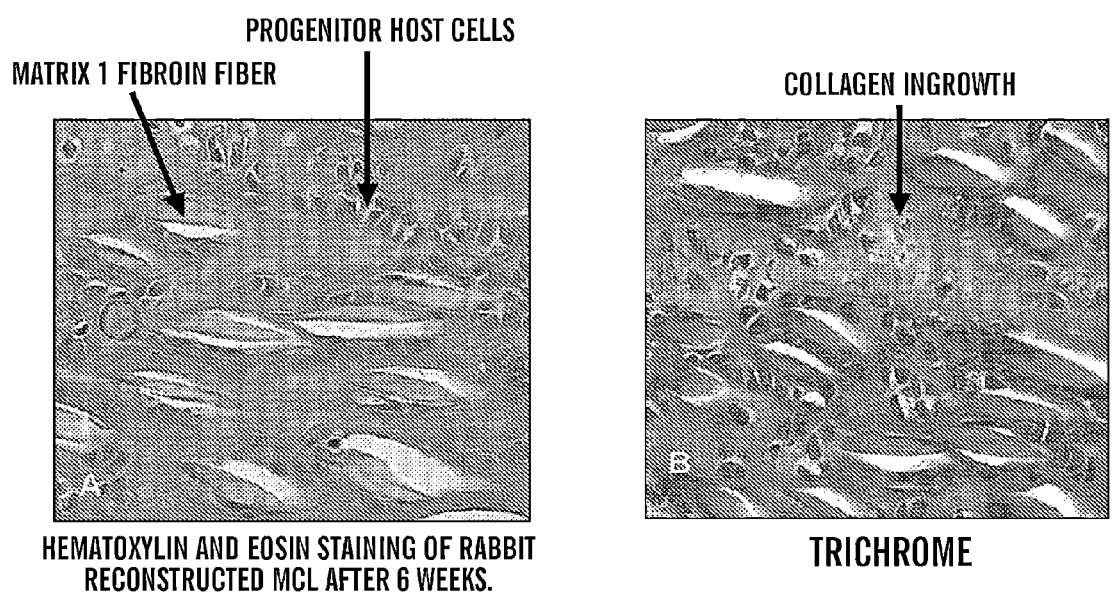
FIG. 15A  FIG. 15B

SILK SUTURE

RGD SURFACE MODIFIED SILK

CELL SEEDED SILK 40X
19C

19D 128X
4x3x3

12x3

SERICIN EXTRACTED FABRICS

CROSS REFERENCE TO RELATED APPLICATIONS

This application is a continuation of U.S. patent application Ser. No. 13/561,808, filed Jul. 30, 2012, which is a divisional of U.S. patent application Ser. No. 12/770,588, filed Apr. 29, 2010, which is a continuation of U.S. patent application Ser. No. 10/800,134, filed Mar. 11, 2004, which claims the benefit under 35 U.S.C. §119(e) to U.S. Provisional Application No. 60/453,584, filed Mar. 11, 2003, and is a continuation-in-part of U.S. patent application Ser. No. 10/008,924, filed Nov. 16, 2001, now U.S. Pat. No. 6,902,932, each of which are incorporated herein by reference in their entirety.

BACKGROUND

Disease, aging, trauma or chronic wear often lead to tissue or organ failure. In treating such failures, the goal of many clinical procedure is restoration of function. A patient often requires additional support, beyond the body's own means of healing, such as surgery or the implantation of a medical device. Such procedures are often needed to combat permanent disability and even death. The fields of biomaterials and tissue engineering are providing new options to gradually restore native tissue and organ function through the research and development of temporary scaffolds, matrices, and constructs (i.e., devices) that initially support a disabled tissue or organ, but eventually allow for the development and remodeling of the body's own biologically and mechanically functional tissue.

The responsibilities or design requirements of such a scaffold include: (i) the ability to provide immediate mechanical stabilization to the damaged or diseased tissue, (ii) support cell and tissue ingrowth into the device, (iii) communicate the mechanical environment of the body to the developing tissue; such is achieved through the proper mechanical and biological design of the device, (iv) degrade at such a rate that the ingrowing cells and tissue have sufficient time to remodel, thus creating new autologous function tissue that can survive the life of the patient. In certain instances, the device should mimic the correct three-dimensional structure (e.g., a bone scaffold) of the tissue it is attempting to support. In other instances, the device may serve as a temporary ligature (e.g., a flat mesh for hernia repair or a hemostat for bleeding) to a three-dimensional tissue (abdominal wall muscle in the case of hernia). Regardless of application, the present direction of the medical device field is the complete restoration of bodily function through the support of autologous tissue development.

Unfortunately, most biomaterials available today do not possess the mechanical integrity of high load demand applications (e.g., bone, ligaments, tendons, muscle) or the appropriate biological functionality; most biomaterials either degrade too rapidly (e.g., collagen, PLA, PGA, or related copolymers) or are non-degradable (e.g., polyesters, metal), where in either case, functional autologous tissue fails to develop and the patient suffers disability. In certain instances a biomaterial may misdirect tissue differentiation and development (e.g., spontaneous bone formation, tumors) because it lacks biocompatibility with surrounding cells and tissue. As well, a biomaterial that fails to degrade typically is associated with chronic inflammation, where such a response is actually detrimental to (i.e., weakens) surrounding tissue.

If properly designed, silk may offer new clinical options for the design of a new class of medical devices, scaffolds and matrices. Silk has been shown to have the highest strength of any natural fiber, and rivals the mechanical properties of synthetic high performance fibers. Silks are also stable at high physiological temperatures and in a wide range of pH, and are insoluble in most aqueous and organic solvents. Silk is a protein, rather than a synthetic polymer, and degradation products (e.g., peptides, amino acids) are biocompatible. Silk is non-mammalian derived and carries far less bioburden than other comparable natural biomaterials (e.g., bovine or porcine derived collagen).

Silk, as the term is generally known in the art, means a filamentous fiber product secreted by an organism such as a silkworm or spider. Silks produced from insects, namely (i) *Bombyx mori* silkworms, and (ii) the glands of spiders, typically *Nephila clavipes*, are the most often studied forms of the material; however, hundreds to thousands of natural variants of silk exist in nature. Fibroin is produced and secreted by a silkworm's two silk glands. As fibroin leaves the glands, it is coated with sericin, a glue-like substance. However, spider silk is valued (and differentiated from silkworm silk) as it is produced as a single filament lacking any immunogenic contaminates, such as sericin.

Unfortunately, spider silk can not be mass produced due to the inability to domesticate spiders; however, spider silk, as well as other silks can be cloned and recombinantly produced, but with extremely varying results. Often, these processes introduce bioburdens, are costly, cannot yield material in significant quantities, result in highly variable material properties, and are neither tightly controlled nor reproducible.

As a result, only silkworm silk has been used in biomedical applications for over 1,000 years. The *Bombyx mori* specie of silkworm produces a silk fiber (known as a "bave") and uses the fiber to build its cocoon. The bave, as produced, includes two fibroin filaments or "broins", which are surrounded with a coating of gum, known as sericin—the silk fibroin filament possesses significant mechanical integrity. When silk fibers are harvested for producing yarns or textiles, including sutures, a plurality of fibers can be aligned together, and the sericin is partially dissolved and then resolidified to create a larger silk fiber structure having more than two broins mutually embedded in a sericin coating.

As used herein, "fibroin" includes silkworm fibroin (i.e. from *Bombyx mori*) and fibroin-like fibers obtained from spiders (i.e. from *Nephila clavipes*). Alternatively, silk protein suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

Silkworm silk fibers, traditionally available on the commercial market for textile and suture applications are often "degummed" and consist of multiple broins plied together to form a larger single multi-filament fiber. Degumming here refers to the loosening of the sericin coat surrounding the two broins through washing or extraction in hot soapy water. Such loosening allows for the plying of broins to create larger multifilament single fibers. However, complete extraction is often neither attained nor desired. Degummed silk often contains or is recoated with sericin and/or sericin impurities are introduced during plying in order to congeal the multifilament single fiber. The sericin coat protects the frail fibroin filaments (only ~5 microns in diameter) from fraying during traditional textile applications where high-through-put processing is required. Therefore, degummed silk, unless explicitly stated as sericin-free, typically contain 10-26% (by weight) sericin (see Tables 1 & 2).

When typically referring to "silk" in the literature, it is inferred that the remarks are focused to the naturally-occurring and only available "silk" (i.e., sericin-coated fibroin fibers) which have been used for centuries in textiles and medicine. Medical grade silkworm silk is traditionally used in only two forms: (i) as virgin silk suture, where the sericin has not been removed, and (ii) the traditional more popular silk suture, or commonly referred to as black braided silk suture, where the sericin has been completely removed, but replaced with a wax or silicone coating to provide a barrier between the silk fibroin and the body tissue and cells. Presently, the only medical application for which silk is still used is in suture ligation, particularly because silk is still valued for it mechanical properties in surgery (e.g., knot strength and handlability).

Despite virgin silk's use as a suture material for thousands of years, the advent of new biomaterials (collagen, synthetics) have allowed for comparisons between materials and have identified problems with sericin. Silk, or more clearly defined as *Bombyx mori* silkworm silk, is non-biocompatible. Sericin is antigenic and elicits a strong immune, allergic or hyper-T-cell type (versus the normal mild "foreign body" response) response. Sericin may be removed (washed/extracted) from silk fibroin; however, removal of sericin from silk changes the ultrastructure of the fibroin fibers, exposing them, and results in loss of mechanical strength, leading to a fragile structure.

Extracted silk structures (i.e., yarns, matrices) are especially susceptible to fraying and mechanical failure during standard textile procedures due to the multifilament nature of the smaller diameter (~5 um) fibroin filaments. The extracted fibroin's fragility is the reason that when using silk in the design and development of medical devices, following extraction, it is typically taught (Perez-Rigueiro, J. Appl. Polymer Science, 70, 2439-2447, 1998) that you must dissolve and reconstitute silk using standard methods (U.S. Pat. No. 5,252,285) to gain a workable biomaterial. The inability to handle extracted silk fibroin with present-day textile methods and machinery has prevented the use of non-dissolved sericin-free fibroin from being explored as a medical device.

Additional limitations of silk fibroin, whether extracted from silkworm silk, dissolved and reconstituted, or produced from spiders or insects other than silkworms include (i) the hydrophobic nature of silk, a direct result of the beta-sheet crystal conformation of the core fibroin protein which gives silk its strength, (ii) the lack of cell binding domains typically found in mammalian extracellular matrix proteins (e.g., the peptide sequence RGD), and (iii) silk fibroin's smooth surface. As a result, cells (e.g., macrophages, neutrophils) associated with an inflammatory and host tissue response are unable to recognize the silk fibroin as a material capable of degradation. These cells thus opt to encapsulate and wall off the foreign body (see FIG. 18A) thereby limiting (i) silk fibroin degradation, (ii) tissue ingrowth, and (iii) tissue remodeling. Thus, silk fibroin filaments frequently induce a strong foreign body response (FBR) that is associated with chronic inflammation, a peripheral granuloma and scar encapsulation (FIG. 18A).

In addition to the biological disadvantages of silk, the multifilament nature of silk (e.g., as sutures) as well as the small size of the fibroin filaments can lead to a tightly packed structure. As such, silk may degrade too rapidly. Proteases (enzymes) produced from the stimulated cells found within the peripheral encapsulation can penetrate the implanted structure (see FIG. 11A and FIG. 11B), but cells depositing new tissue (e.g., fibroblasts) which may reinforce the device (in this case a black braided suture) during normal tissue remodeling cannot. Therefore, the interior of non-treated or non-modified fibroin devices does not come in contact with the host foreign body response and tissue (led and produced by fibroblasts) and as a result, the capacity of the device to direct tissue remodeling is limited. Host cell and tissue growth is limited and degradation is not normally possible.

In the case of sutures, it is thought that these problems can be managed by treating fibroin sutures with cross-linking agents or by coating the sutures with wax, silicone or synthetic polymers, thereby shielding the material from the body. Coatings, such as sericin, wax or silicone, designed to add mechanical stability to the fibroin (combating its fragility while providing a barrier between the body and the fibroin), limits cell attachment, recognition and infiltration and tissue ingrowth and fibroin degradation. As a result, silk is traditionally thought of as a non-degradable material.

Classification as a non-degradable may be desirable when silk is intended for use as a traditional suture ligation device, i.e., cell and tissue ingrowth into the device are not desirable. Therefore, cell attachment and ingrowth (which lead to matrix degradation and active tissue remodeling) is traditionally prevented by both the biological nature of silk and the structure's mechanical design. In fact, a general belief that silk must be shielded from the immune system and the perception that silk is non-biodegradable have limited silk's use in surgery. Even in the field of sutures, silk has been displaced in most applications by synthetic materials, whether biodegradable or permanent.

Therefore, there exists a need to generate sericin-extracted silkworm fibroin fibers that are biocompatible, promote ingrowth of cells, and are biodegradable.

SUMMARY

Natural silk fibroin fiber constructs, disclosed herein, offer a combination of high strength, extended fatigue life, and stiffness and elongation at break properties that closely match those of biological tissues. The fibers in the construct are non-randomly aligned into one or more yarns. The fiber constructs are biocompatible (due to the extraction of sericin from the silkworm silk fibers) and substantially free of sericin. The fiber constructs are further non-immunogenic; i.e., they do not elicit a substantial allergic, antigenic, or hyper T-cell response from the host, diminishing the injurious effect on surrounding biological tissues, such as those that can accompany immune-system responses in other contexts. In addition, the fiber constructs promote the ingrowth of cells around said fibroin fibers and are biodegradable.

Indications that the fiber construct is "substantially free" of sericin mean that sericin comprises less than 20% sericin by weight. Preferably, sericin comprises less than 10% sericin by weight. Most preferably, sericin comprises less than 1% sericin by weight (see Table 2). Furthermore, "substantially free" of sericin can be functionally defined as a sericin content that does not elicit a substantial allergic, antigenic, or hyper T-cell response from the host. Likewise, indication that there is less than a 3% change in mass after a second extraction would imply that the first extraction "substantially removed" sericin from the construct and that the resulting construct was "substantially free" of sericin following the first extraction (see Table 2 and FIG. 1F).

Methods of this disclosure extract sericin from the construct much more thoroughly than do the typical "degumming" procedures that characterize traditional processing practices for the production of silk textiles for non-surgical applications (see above for definition). FIG. 1A shows an image of a degummed fiber where fibroin filaments were plied together forming a larger fiber re-encased with sericin. This "degummed" fiber contains ~26%, by weight, sericin. In a preferred embodiment, the sericin-extracted silkworm fibroin fibers retain their native protein structure and have not been dissolved and reconstituted.

"Natural" silk fibroin fibers are produced by an insect, such as a silkworm or a spider and possess their native, as formed, protein structure. Preferably, the silk fibroin fiber constructs are non-recombinant (i.e., not genetically engineered) and have not been dissolved and reconstituted. In a preferred embodiment, the sericin-extracted fibroin fibers comprised fibroin fibers obtained from Bombyx mori silkworm. Further, the term, "biodegradable," is used herein to mean that the fibers are degraded within one year when in continuous contact with a bodily tissue. In addition, our data suggests (FIG. 13 A-E, FIG. 18 A-C & FIG. 19 A-D) that the rate of degradation can be influenced and enhanced by surface modification of the fibroin (FIG. 13 A-D & FIG. 18 A-C) as well as the geometric configuration of the yarn and/or fabric (FIG. 19A-D). In one embodiment, silk fibroin yarn lost 50% of its ultimate tensile strength within two weeks following implantation in vivo (FIG. 12) and 50% of its mass within approximately 30 to 90 days in vivo, depending on implantation sight (FIG. 13 A-D). The choice of implantation site in vivo (e.g., intra-muscular versus subcutaneous) was shown to significantly influence the rate of degradation (FIG. 13 A-D).

Textile-grade silk" is naturally occurring silk that includes a sericin coating of greater than 19%-28% by weight of the fiber. "Suture silk" is silk that either contains sericin ("virgin silk suture") or is coated with a hydrophobic composition, such as bee's wax, paraffin wax, silicon, or a synthetic polymeric coating ("black braided silk suture"). The hydrophobic composition repels cells or inhibits cells from attaching to the coated fiber. Black braided silk is a suture silk in which sericin has been extracted and replaced with additional coating. Suture silk is typically non-biodegradable.

Due to the absence of a protective wax or other hydrophobic coating on the fibers the silk fibroin constructs described are biologically (coupling of cell binding domains) and/or mechanically (increase silk surface area and decrease packing density) designed to promote increased cell infiltration compared to textile-grade silk or suture silk when implanted in bodily tissue. As a result, the silk fibroin constructs support cell ingrowth/infiltration and improved cell attachment and spreading, which leads to the degradation of the silk fibroin construct thereby essentially creating a new biodegradable biomaterial for use in medical device and tissue engineering applications. The ability of the fiber construct to support cell attachment and cell and tissue ingrowth/infiltration into the construct, which in return supports degradation, may be further enhanced through fibroin surface modification (peptide coupling using RGD, chemical species modification and increasing hydrophilicity through gas plasma treatment) and/or the mechanical design of the construct thereby increasing material surface area thus increasing its susceptibility to those cells and enzymes that possess the ability to degrade silk. The silk fibers are optionally coated with a hydrophilic composition, e.g., collagen or a peptide composition, or mechanically combined with a biomaterial that supports cell and tissue ingrowth to form a composite structure. The choice of biomaterial, amount and mechanical interaction (e.g., wrapped or braided about a core of silk fibroin) can be used to alter and/or improve rates of cell ingrowth and construct degradation.

Fibers in the construct are non-randomly aligned with one another into one or more yarns. Such a structure can be in a parallel, braided, textured, or helically-organized (twisted, cabled (e.g., a wire-rope)) arrangement to form a yarn. A yarn may be defined as consisting of at least one fibroin fiber. Preferably, a yarn consists of at least three aligned fibroin fibers. A yarn is an assembly of fibers twisted or otherwise held together in a continuous strand. An almost infinite number of yarns may be generated through the various means of producing and combining fibers. A silk fiber is described above; however, the term fiber is a generic term indicating that the structure has a length 100 times greater than its diameter.

When the fibers are twisted or otherwise intertwined to form a yarn, they are twisted/intertwined enough to essentially lock in the relative fiber positions and remove slack but not so much as to plastically deform the fibers (i.e., does not exceed the material's yield point), which compromises their fatigue life (i.e., reduces the number of stress cycles before failure). The sericin-free fibroin fiber constructs can have a dry ultimate tensile strength (UTS) of at least 0.52 N/fiber (Table 1, 4), and a stiffness between about 0.27 and about 0.5 N/mm per fiber. Depending on fiber organization and hierarchy, we have shown that fibroin construct UTSs can range from 0.52 N/fiber to about 0.9N/fiber. Fibroin constructs described here retained about 80% of their dry UTS and about 38% of their dry stiffness, when tested wet (Table 5). Elongations at break between about 10% and about 50% were typical for fibroin constructs tested in both dry and wet states. Fibroin constructs typically yielded at about 40 to 50% of their UTS and had a fatigue life of at least 1 million cycles at a load of about 20% of the yarns ultimate tensile strength.

In one embodiment of the present invention, the aligned sericin-extracted silkworm fibroin fibers are twisted about each other at 0 to 11.8 twists per cm (see Table 6 & 7).

The number of hierarchies in the geometrical structure of the fiber construct as well as the number of fibers/groups/bundles/strands/cords within a hierarchical level, the manner of intertwining at the different levels, the number of levels and the number of fibers in each level can all be varied to change the mechanical properties of the fiber construct (i.e., yarn) and therefore, fabric (Table 4 & 8). In one embodiment of the present invention, the fiber construct (i.e. yarn) is organized in a single-level hierarchical organization, said single-level hierarchical organization comprising a group of parallel or intertwined yarns. Alternatively, the fiber construct (i.e. yarn) organized in a two-level hierarchical organization, said two-level hierarchical organization comprising a bundle of intertwined groups. In another embodiment of the present invention, the fiber construct (i.e. yarn) is organized into a three-level hierarchical organization, said three-level hierarchical organization comprising a strand of intertwined bundles. Finally, another embodiment of the present invention, the fiber construct (i.e. yarn) is organized into a four-level hierarchical organization, said four-level hierarchical organization comprising a cord of intertwined strands.

The sericin can be removed from the fibroin fibers before the alignment into a yarn or at a higher level in the hierarchical geometry of the fiber construct. The yarn is handled at low tension (i.e., the force applied to the construct will never exceed the material's yield point during any processing step) and with general care and gentleness after the sericin is removed. Processing equipment is likewise configured to reduce abrasiveness and sharp angles in the guide fixtures that contact and direct the yarn during processing to protect the fragile fibroin fibers from damage; extraction residence times of 1 hour are sufficient to extract sericin but slow enough as not to damage the exposed filaments. Interestingly, when a silk fiber construct consisting of multiple fibers organized in parallel has been extracted under these conditions, a "single"

larger sericin free yarn resulted (i.e., individual fibers cannot be separated back out of the construct due to the mechanical interaction between the smaller fibroin filaments once exposed during extraction). Furthermore, as a result of the mechanical interplay between the sericin-free micro filaments, extraction of twisted or cabled yarns has typically resulted in less "lively" yarns and structures. As a result of this phenomenon, a greater degree of flexibility existed in the design of the yarns and resulting fabrics; for example, higher twist per inch (TPI) levels can be used, which would normally create lively yarns that would be difficult to form into fabrics. The added benefit of higher TPIs was the reduction in yarn and fabric stiffness (i.e. matrix elasticity can be increased) (Tables 6 and 7; FIG. 6A and FIG. 6B).

A plurality of yarns are intertwined to form a fabric. Fabrics are generated through the uniting of one or more individual yarns whereby the individual yarns are transformed into textile and medical device fabrics. In one embodiment of the present invention, the yarn is twisted at or below 30 twists per inch. Fabrics are produced or formed by non-randomly combining yarns: weaving, knitting, or stitch bonding to produce completed fabrics. In one embodiment, this combining of yarns to form a fabric is done on a machine. However, it is very important to note that the end fabric product is distinct based on the yarn type used to make it thus providing tremendous power through yarn design to meet clinical needs. A fabric can be, but is not limited to, woven, knit, warp-knit, bonded, coated, dobby, laminated, mesh, or combinations thereof.

Of note, the textile methods of braiding, in addition to making yarns, can also be used to make fabrics, such as a flat braided fabric or a larger circular braid (FIG. 4A). Inversely, weaving and knitting, two fabric forming methods, although not commonly used, can also be used to make yarns. In such instances, the differentiation between a "yarn" and a "fabric" is not entirely apparent, and the homogeneity should be used to make clear distinctions, i.e., a yarn is typically more homogeneous in composition and structure than a fabric.

In one embodiment of the present invention, multiple silkworm silk fibers may be organized helically (e.g., twisted or cabled) or in parallel, in a single hierarchical level or in multiple levels, extracted, and used to create a braided suture for tissue ligation. In another embodiment, the mechanical interaction of extracted fibroin filaments in a twisted or cabled configuration following extraction can be used as a medical suture.

Non-woven fabrics may be formed by randomly organizing a plurality of yarns, or a single yarn cut into many small length pieces. Non-limiting examples include a fabric for hemostat or bone scaffold. All fabrics can either derive from a single yarn construct (homogenous) or multiple yarns constructs (heterogeneous). The ability to design for a variety of silk fibroin yarn structures, as described in detail below, dramatically increases fabric design potential when considering a heterogeneous fabric structure.

In one embodiment of the present invention, the fabric is a composite of the sericin-extracted fibroin fibers or yarns and one or more degradable polymers selected from the group consisting of Collagens, Polylactic acid or its copolymers, Polyglycolic acid or its copolymers, Polyanhydrides, Elastin, Glycosamino glycans, and Polysaccharides. Furthermore, the fabric of the present invention may be modified to comprise a drug associated or a cell-attachment factor associated with fabric (i.e. RGD). In one embodiment of the present invention, the fabric is treated with gas plasma or seeded with biological cells.

Additional aspects of this disclosure relate to the repair of specific bodily tissues, such as hernia repair, urinary bladder tissues and slings, pelvic floor reconstruction, peritoneal wall tissues, vessels (e.g., arteries), muscle tissue (abdominal smooth muscle, cardiac), hemostats, and ligaments and tendons of the knee and/or shoulder as well as other frequently damaged structures due to trauma or chronic wear. Examples of ligaments or tendons that can be produced include anterior cruciate ligaments, posterior cruciate ligaments, rotator cuff tendons, medial collateral ligaments of the elbow and knee, flexor tendons of the hand, lateral ligaments of the ankle and tendons and ligaments of the jaw or temporomandibular joint. Other tissues that may be produced by methods of this disclosure include cartilage (both articular and meniscal), bone, skin, blood vessels, stents for vessel support and/or repair, and general soft connective tissue.

In other aspects, silkworm fibroin fibers, in the form of a yarn or of a larger construct of yarns, now termed a device, is stripped of sericin, and made (e.g., woven, knitted, non-woven wet laid, braided, stitch bonded, etc.) into a fabric, sterilized and used as an implantable supporting or repair material that offers a controllable lifetime (i.e., degradation rate) and a controllable degree of collagen and/or extracellular matrix deposition. The support or repair material can be used for any such purpose in the body, and in particular can be used for hernia repair, reconstruction of body walls, particularly in the thorax and abdominal cavity, and support, positioning or immobilization of internal organs, including, without limitation, the bladder, the uterus, the intestines, the urethra, and ureters. Alternatively, silkworm fibroin fibers may be stripped of sericin and organized into a non-woven fabric. Such non-woven fabric can be used as an implantable supporting or repair material as above, but more specifically for applications where a sponge formation would be useful.

The purified silk can be purified by any of a variety of treatments that remove the sericin proteins found in the native fibrils. Sericin has been removed sufficiently when implants of purified silk elicit only a mild, transient foreign body reaction in the absence of an antigenic (B-cell, T-cell) response, i.e., are biocompatible. A foreign body reaction is characterized by an inner layer of macrophages and/or giant cells with a secondary zone of fibroblasts and connective tissue. The degree of foreign body response has been shown to be controllable through fibroin modification (FIG. 13 A-D & FIG. 18 A-C) and yarn design (FIG. 19 A-D). Sericin can be removed from individual silkworm fibroin fibers, a group of silkworm fibroin fibers (i.e. a yarn), having an organized orientation (e.g., parallel or twisted), or form a fabric or other construct comprising a plurality of yarns. The construct can then be sterilized and implanted in an organism as a medical device.

Other features and advantages of the invention will be apparent from the following description of preferred embodiments thereof.

BRIEF DESCRIPTION OF THE FIGURES

FIG. 1A is a scanning electron microscopy (SEM) image of a single native degummed and plied 20/22 denier silk fiber having a sericin coating.

FIG. 1B illustrates SEM of the silk fiber of FIG. 1A extracted for 60 min at 37° C.

FIG. 1C illustrates SEM of the silk fiber of FIG. 1A extracted for 60 min at 90° C. and illustrating complete removal of the sericin coating.

FIG. 1D is a chart showing ultimate tensile strength (UTS) and stiffness (N/mm for a 3 cm length matrix) as a function of extraction conditions.

FIG. 1E illustrates SEM of a raw silk fibroin. FIG. 1F illustrates a first extraction at 90° C. for 60 min. FIG. 1G illustrates a second extraction under identical conditions. These figures show mechanical damage to the filaments that results in a typical 3% mass loss following the second extraction. Therefore, as long as the % mass loss does not change more than 3% from the first to the second extraction (90° C., 1 hr, standard detergent and salt), it is assumed that complete extraction has been achieved. The utility of a 3% loss in total mass loss reflects the variability in the measurements, assays and mechanical damage resulting in mass loss of the yarn following the second extraction.

FIG. 2A is a representative 3-D model of a (cable or twisted) yarn depicting its 5 levels of hierarchy (single fiber level not shown). Depending on the number of fibers used in each level, the cord could serve as either a yarn for knitting a hernia repair mesh or as a cord to be used in parallel with other cords to form an ACL matrix.

FIG. 13E is a numerical representation of mass loss in vivo from the two different modification groups compared to non-treated controls. RGD modification, followed by gas plasma modification significantly ($p<0.05$) increased the extent of degradation after 90 days of intra-muscular implantation. However, it appears degradation was more aggressive in the subcutaneous environment as compared to the intra-muscular environment, as was expected.

FIG. 14 illustrates gel electrophoretic analysis of RT-PCR amplification of selected markers over time. The gel shows upregulation in both collagen types I and III expression levels normalized to the housekeeping gene, GAPDH by bone marrow stromal cell grown on Matrix 2 over 14 days in culture. Collagen type II (as a marker for cartilage) and bone sialoprotein (as a marker of bone tissue formation) were not detected indicating a ligament specific differentiation response by the BMSCs when cultured with Matrix 2.

FIG. 15A and FIG. 15B illustrates a single cord of Matrix 1 (not seeded at the time of implantation) following six weeks of implantation in vivo and used to reconstruct the medial collateral ligament (MCL) in a rabbit model. FIG. 15A shows Matrix 1 fibroin fibers surrounded by progenitor host cells and tissue ingrowth into the matrix and around the individual fibroin fibers visualized by hematoxylin and eosin staining FIG. 15B shows collagenous tissue ingrowth into the matrix and around the individual fibroin fibers visualized by trichrome staining.

FIG. 18A shows a typical and extensive foreign body reaction to commercially available (Ethicon, Inc.) black braided silk suture where no ingrowth or cell infiltration can be observed. FIG. 18B demonstrates the engineered silk's ability to promote cell and tissue ingrowth. FIGS. 18A, 18B and 18C illustrate tissue response to silk fiber constructs that are coated in wax (FIG. 18A), stripped of sericin and coated with RGD (FIG. 18B), and stripped of sericin and seeded with progenitor adult stem cells (FIG. 18C).

DETAILED DESCRIPTION

In methods described in greater detail, below, silk fibroin fibers are aligned in a parallel orientation; the fibers can remain in a strictly parallel orientation, or they can be twisted or otherwise intertwined to form a yarn. The yarn can include any number of hierarchies, beginning at fiber level and expanding through bundle, strand, cord, etc., levels. Intertwining can be provided at each level. Furthermore, sericin is extracted from the silk fibers at any point in the hierarchy up to the point where the number of fibers exceeds that at which the extracting solution can penetrate throughout the yarn. The maximum number of silkworm fibroin fibers (20/22 denier as purchased) that can be combined and successfully extracted is about 50 (Table 4). These yarns can then be used as a fiber construct for, e.g., ligament or tissue reconstruction, or can be incorporated into a fabric for use, e.g., in the generation of soft tissue mesh for repairs such as hernia repair, abdominal floor reconstruction and bladder slings. Formation of fiber constructs will be discussed in the context of exemplary applications, below.

Figure 2B:
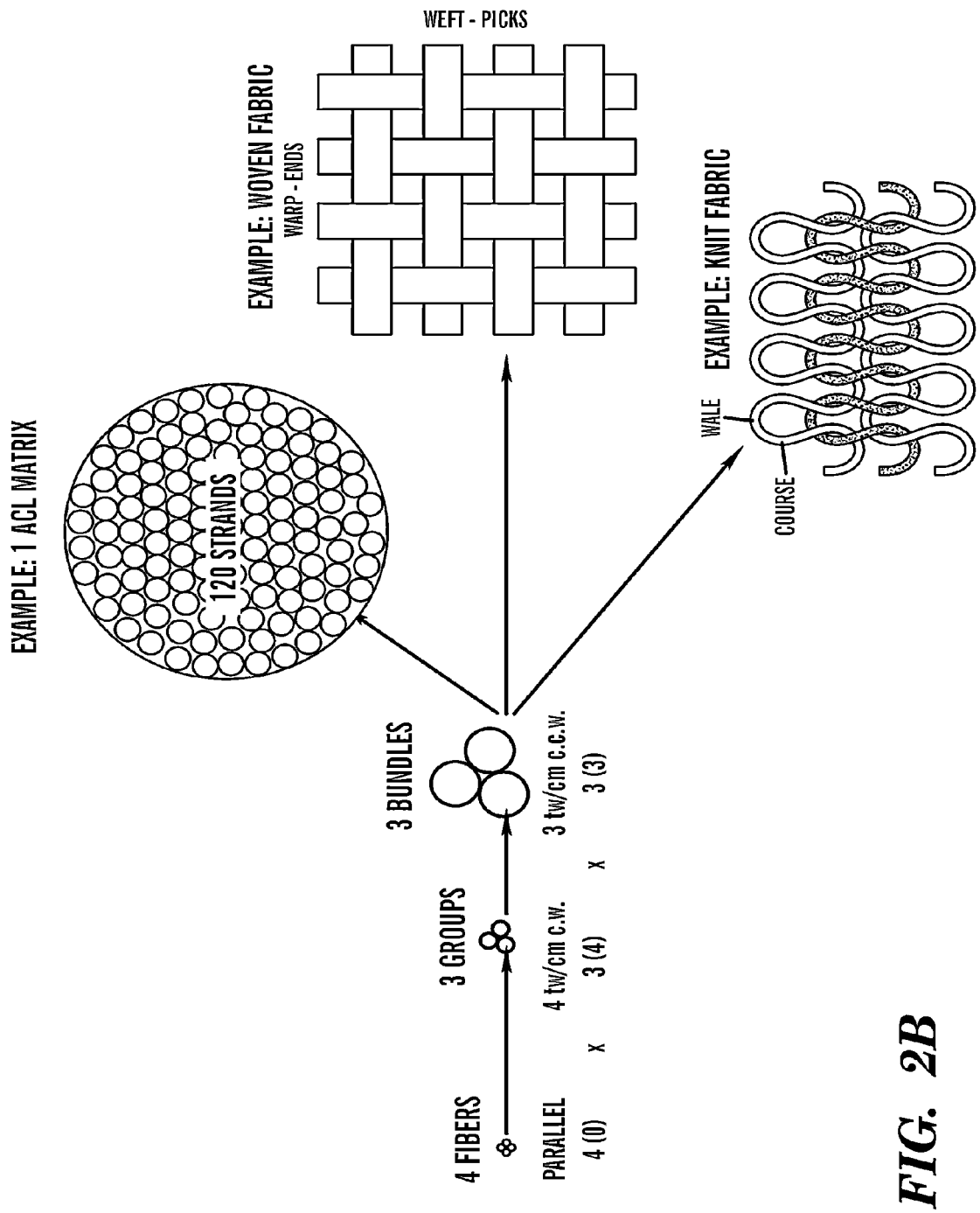
FIG. 2B is a schematic depicting the generation of a two-level hierarchical twisted or cabled yarn containing 36 fibers before being plied in parallel to form an ACL matrix or used to generate a weave or knit fabric for tissue engineering and tissue repair (e.g. hernia mesh). The schematic representations visually define two very popular forms of fabric formations: a "weave" and a "knit."

Although much of the discussion that follows is directed to a silk-fiber-based matrix (i.e. construct, scaffold) for producing an anterior cruciate ligament (ACL), a variety of other tissues, such as other ligaments and tendons, cartilage, muscle, bone, skin and blood vessels, can be formed using a novel silk-fiber based matrix. In the case of the ACL, a large yarn (540-3900 fibers per yarn, before plying in parallel; see Table 8 & 11) with multiple hierarchical levels of intertwining and relevant physiological properties was described. In addition to a silk-fiber-based ACL matrix, multiple smaller yarn configurations (1-50 silk fibers) (Table 1, 4 & 5) with relevant physiological properties after combining either in parallel or into a specific fabric formation, can serve as tissue matrices for guided tissue formation (FIG. 2A-B). In addition to silk matrices for guided tissue formation or engineering, this work is specifically directly to producing a variety of silk-fiber based matrices tissue support structures for guided tissue repair (e.g., hernia repair, bladder slings for urinary stress incontinence) (FIG. 2A-B & FIG. 20A-C).

Constructs (i.e. fabrics or yarns) can be surface modified or seeded with the appropriate cells (FIG. 7A-D, FIG. 8A-B & FIG. 16A-C) and exposed to the appropriate mechanical stimulation, if necessary, for proliferating and differentiating into the desired ligament, tendon or other tissue in accordance with the above-described techniques.

Additionally, the present invention is not limited to using bone marrow stromal cells for seeding on the fiber construct, and other progenitor, pluripotent and stem cells, such as those in bone, muscle and skin for example, may also be used to differentiate into ligaments and other tissues.

Figure 20A:
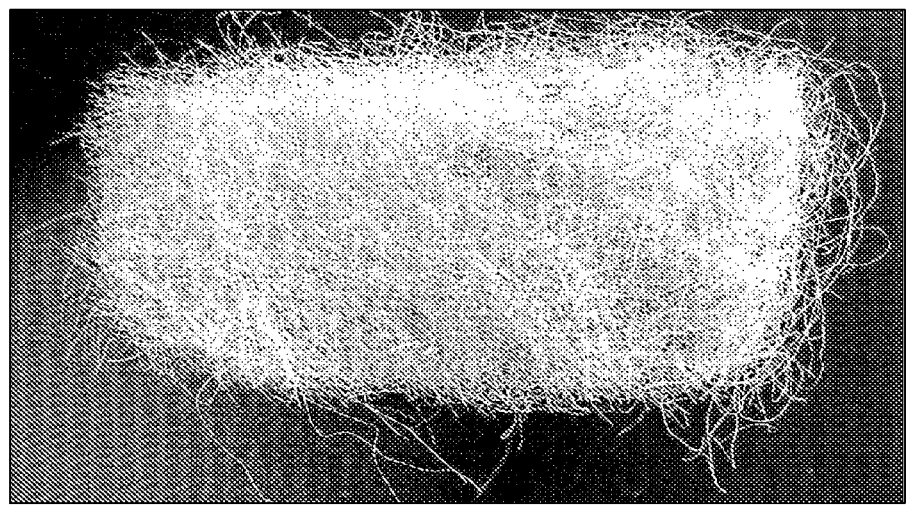
FIGS. 20A, B and C are pictures of (A) single fiber wet laid non-woven fabric extracted post fabric formation (fibers can first be extracted and formed into the non-woven—data not shown), (B) a knit fabric produced from a form of chain stitching using 12-fiber yarn extracted post fabric formation, and (C) a woven fabric produced from pre-extracted 12-fiber yarn with a 36-fiber pre-extracted yarn running in the weft direction.
Figure 20B:
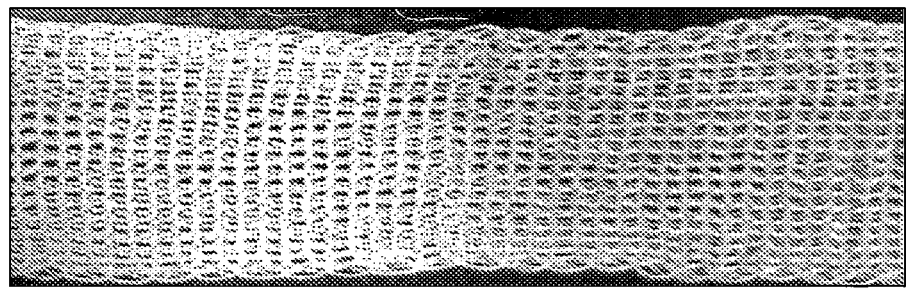

Fabrics can also be formed from similar constructs of purified filaments, and used in various applications. Fabrics can be divided into various classes, including woven, non-woven, knitted fabrics, and stitch-bonded fabrics, each with numerous subtypes. Each of these types may be useful as an implant in particular circumstances. In discussing these silk-based fabrics, we describe the natural silk, e.g., of *Bombyx mori*, as a "fibroin fiber." The fibers should be at least one meter long, and this length should be maintained throughout the process to facilitate their handling during processing and incorporation into a fabric. Given that a yarn may be defined as an assembly of fibers twisted or otherwise held together in a continuous strand and that a single fibroin fiber, as defined above, is comprised of multiple plied broins, sometimes from multiple cocoons, a single fibroin fiber may be termed a "yarn." As well, fibroin fibers are twisted together or otherwise intertwined to form a "yarn." Yarns are used to weave or knit fabrics for use in the invention. In an alternative procedure, silk yarns are disaggregated into shorter (5 mm to 100 mm) lengths or into silk fibroin filaments. These filaments may then be (wet) laid to form a non-woven fabric (FIG. 20A).

Figure 3A:
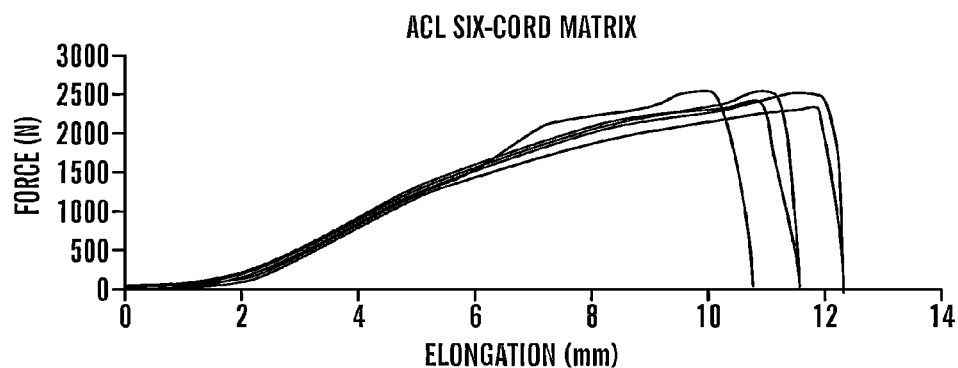
FIG. 3A illustrates load-elongation curves for five samples (n=5) of Matrix 1 formed from six parallel silk fibroin cords illustrated in FIG. 2A.
Figure 3B:
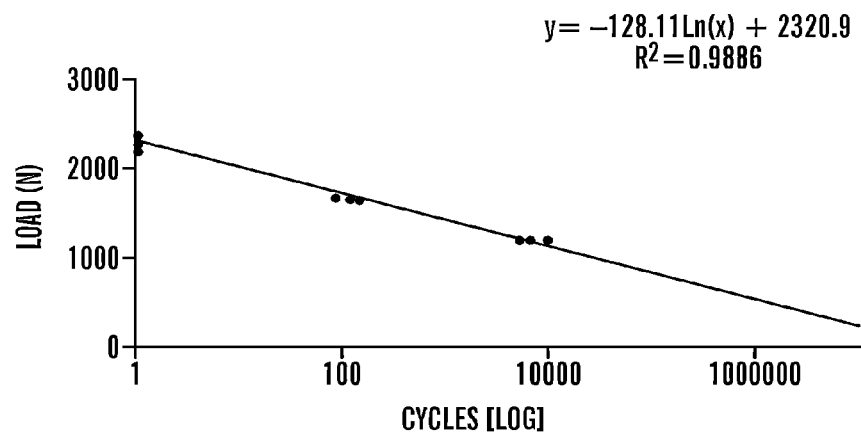
FIG. 3B is a chart of cycles to failure at UTS, 1680 N, and 1200 N loads (n=5 for each load) illustrating Matrix 1 fatigue data. Regression analysis of Matrix 1 fatigue data, when extrapolated to physiological load levels (400 N) to predict number of cycles to failure in vivo, indicates a matrix life of 3.3 million cycles.
Figure 3C:
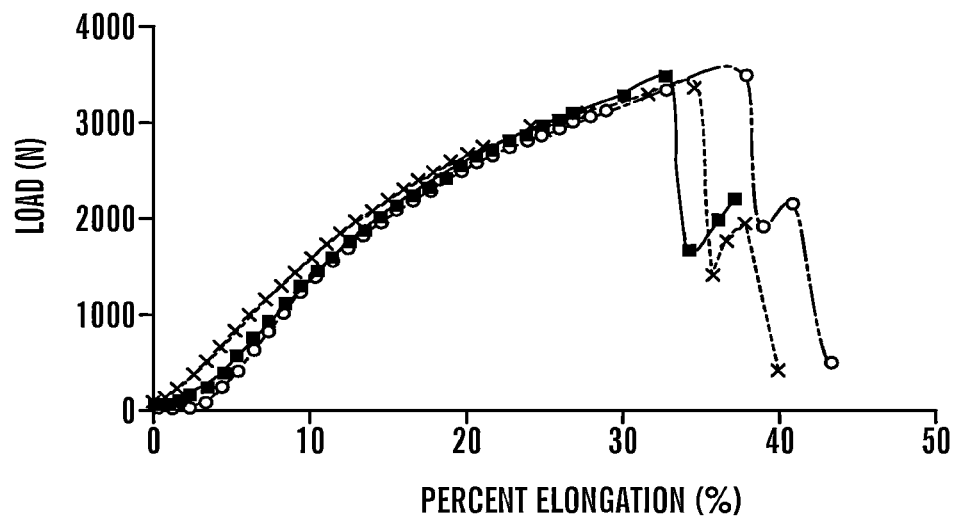
FIG. 3C illustrates load-elongation curves for three samples (n=3) of Matrix 2 (n=3) formed from six parallel silk fibroin cords as illustrated in FIG. 2B.
Figure 3D:
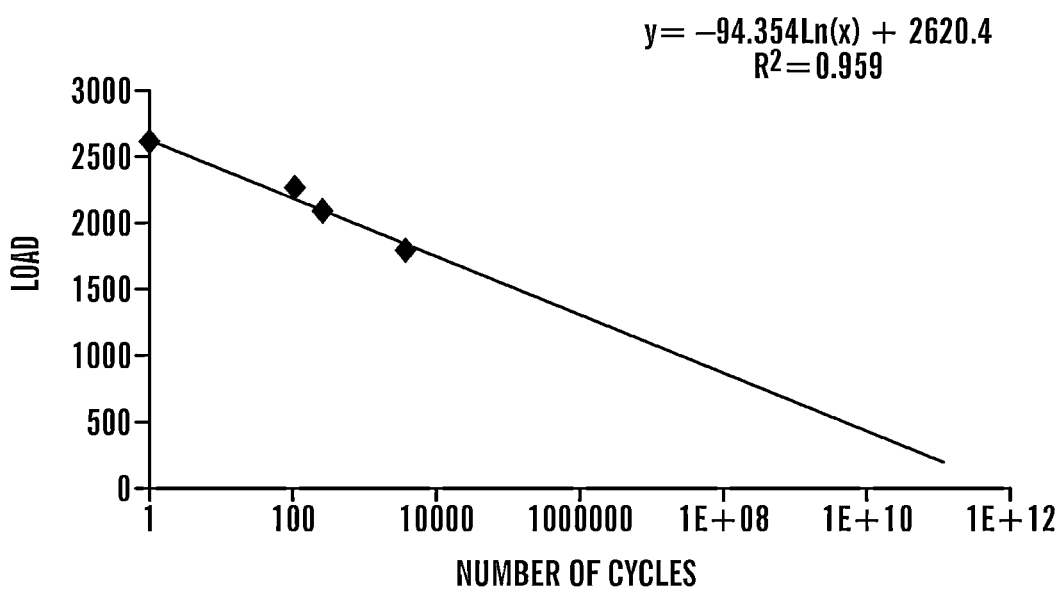
FIG. 3D is a chart of cycles to failure at UTS, 2280 N, 2100 N and 1800 N loads (n=3 for each load) illustrating Matrix 2 fatigue data. Regression analysis of Matrix 2 fatigue data, when extrapolated to physiological load levels (400 N) to predict number of cycles to failure in vivo, indicates a matrix life of greater than 10 million cycles.
Figure 4A:
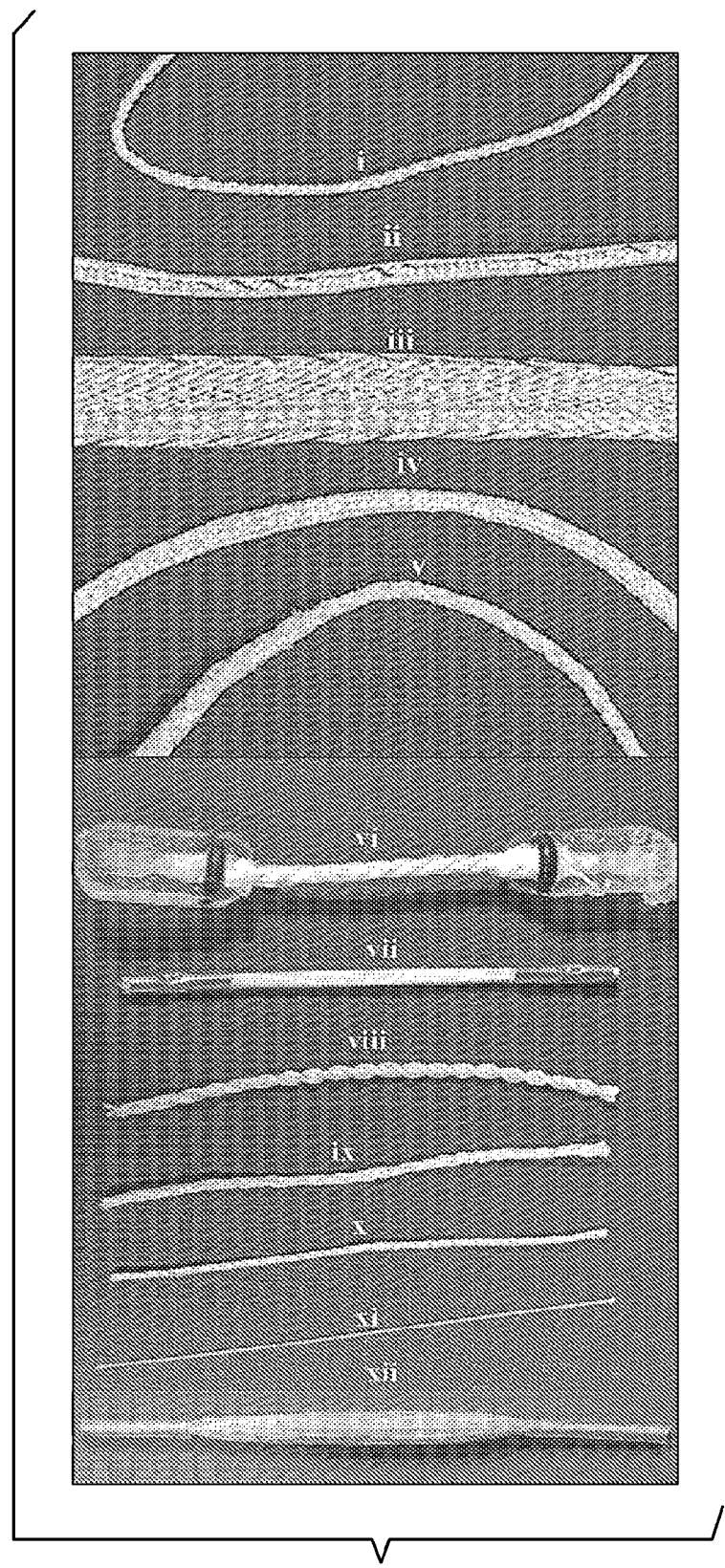
FIG. 4A shows images of multiple yarn and fabric forms generated in our laboratories. Several different yarn structures, including various types of braids (i, ii, iv), a flat braid (iii), a varying diameter or taper braid (v), a larger (~250 fibers) cabled two-level bundle (vi), a parallel plied and bonded (swaged) yarn consisting 24-12-fiber textured yarns (vii), a variety of twisted yarns (viii-xi), and a parallel plied and bonded (swaged) yarn consisting 24-12-fiber two level cabled yarns (xii).
Figure 4B:
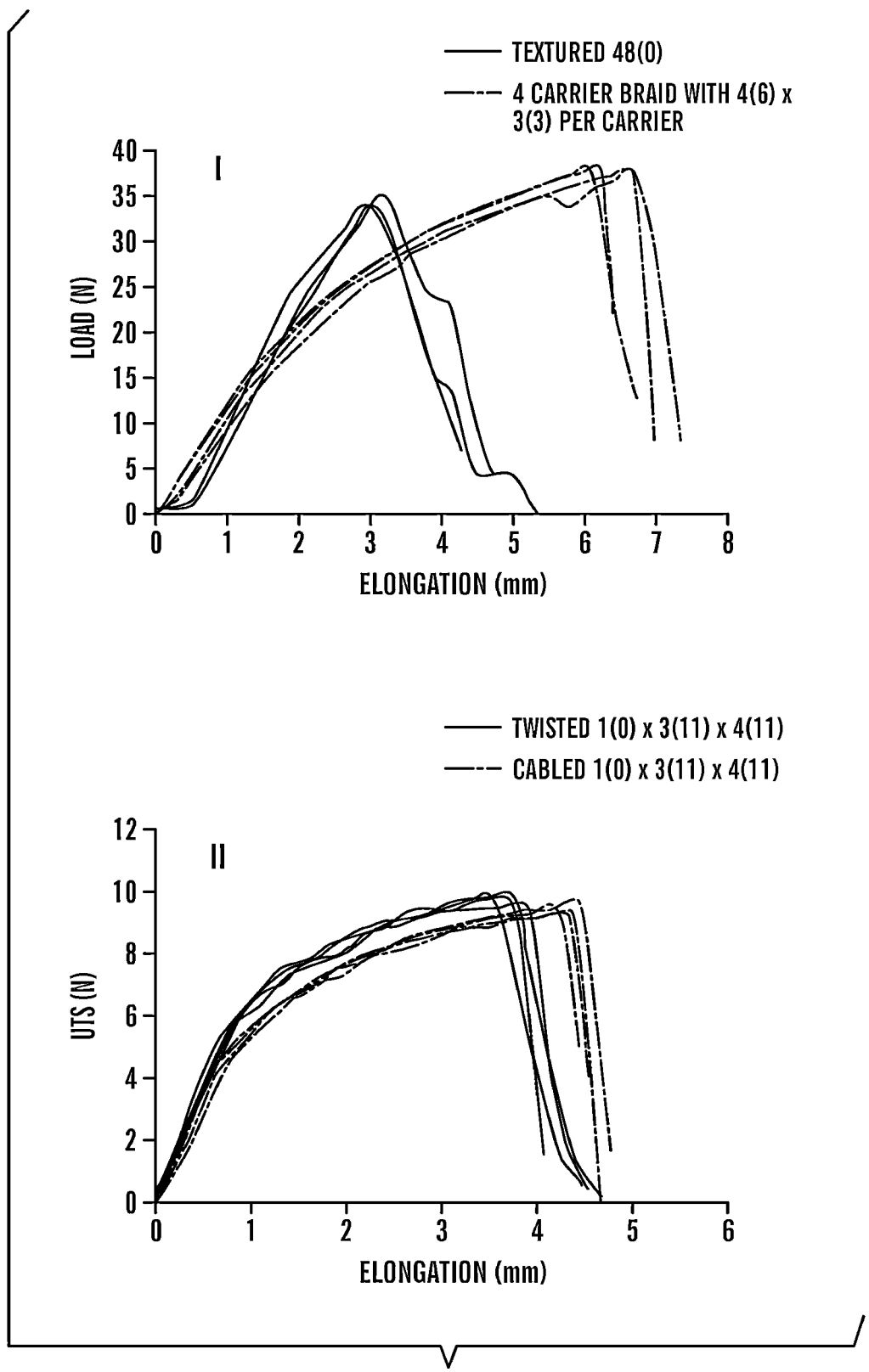
FIG. 4B is a chart of load-elongation curves for (I) a braid (48 fibers, a 4 carrier braider using twisted extracted 12 fiber yarn) and textured yarns (48 fibers total) and (II) twisted compared to cabled yarns, 12 fibers in total—all samples were 3 cm in length.
Figure 4C:
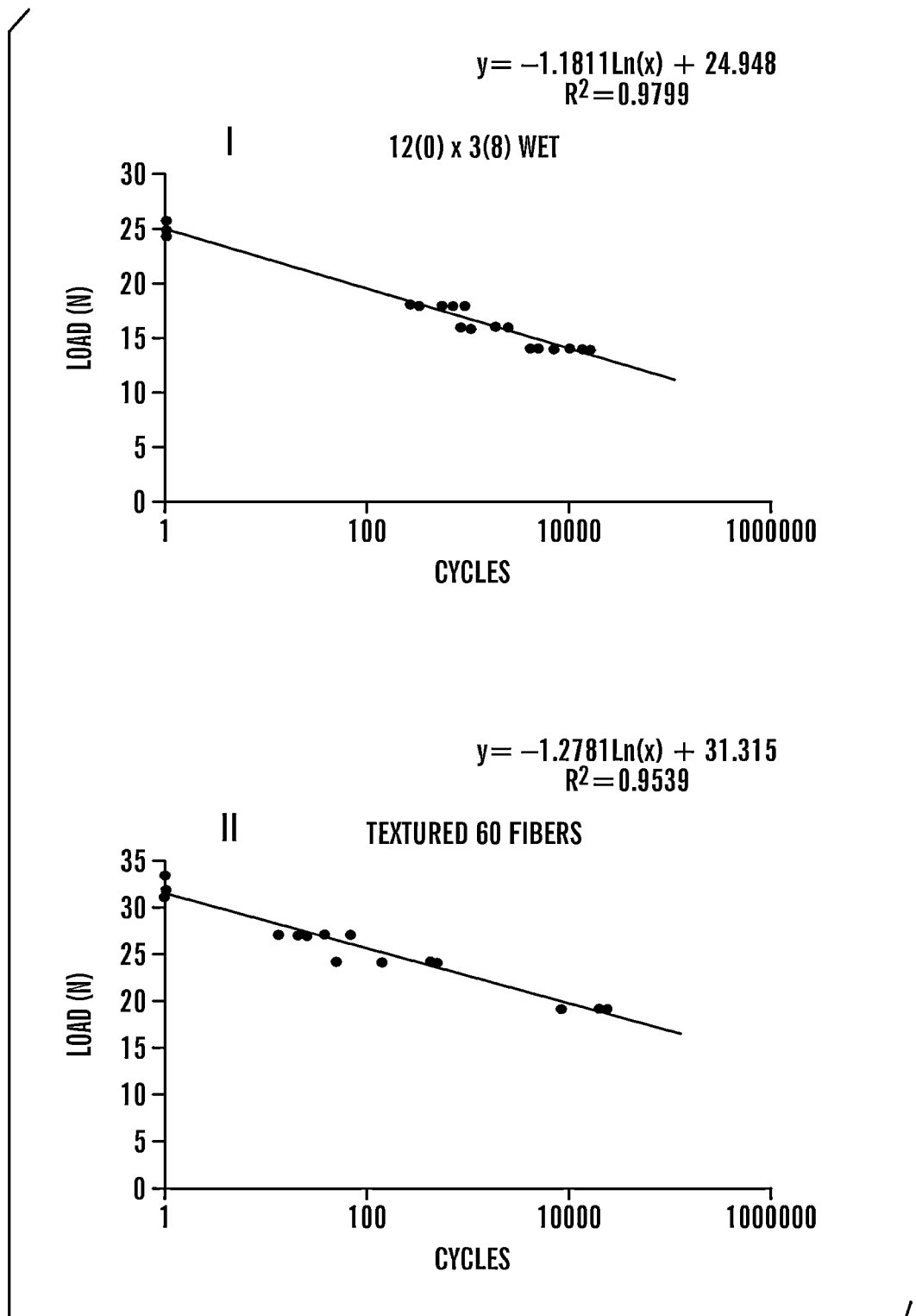
FIG. 4C is a chart of fatigue data for small yarns, 3 cm in length, as compared to 3B and 3D for (I) a small cable of 36 fibers and (II) a small textured yarn of 60 fibers).

When the yarns are formed into a fabric, the tension (force) exerted on the yarns (typically, via machinery) is no greater than the yarn's yield point (FIG. 3A-D). Accordingly, the yarns are handled at lower speeds and under smaller loads than are yarns that are typically used in, e.g., textile manufacturing when forming the fabric so as to preserve the integrity of the exposed fragile fibroin fibers. Likewise, contact points between handling machinery and the yarn are designed to avoid sharp angles and high-friction interactions so as to prevent lousing and fraying of fibers around the perimeter of the yarn (FIG. 4A-C).

Figure 13A:
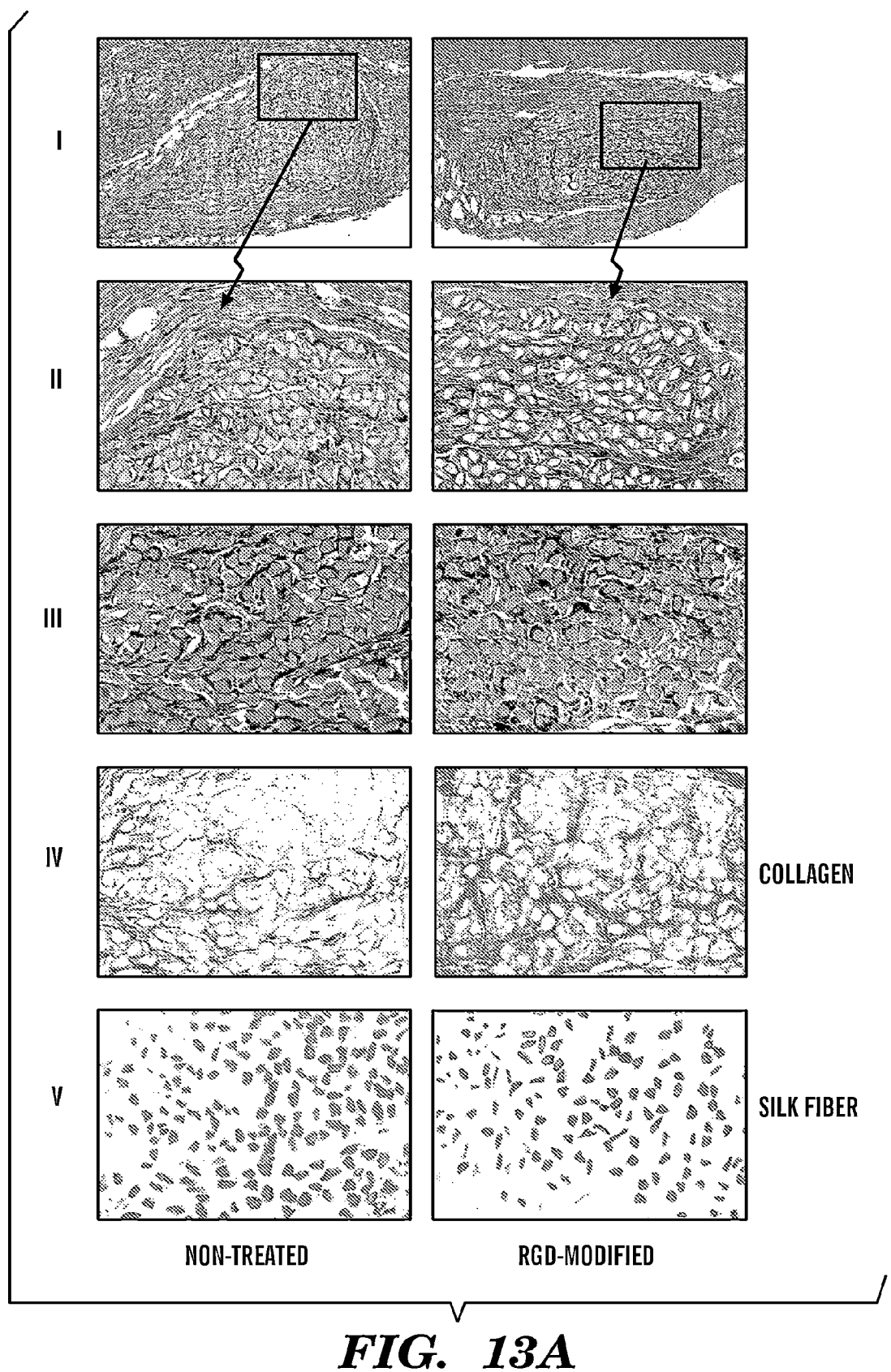
FIG. 13A shows histological sections of 12(0)×3(8) non-modified and RGD-modified sericin-free silk fibroin matrices after 30 days of subcutaneous implantation in a Lewis rat. Row I is H&E staining at 40×, row II is H&E staining at 128×, row III is collagen trichrome staining at 128×, row IV is collagen backed out of the row III images to allow for collagen ingrowth quantification and row V are the pixels associated with the cross-sections of remaining silk fibroins backed out to allow for quantification of degradation. Upon qualitative assessment, in the subcutaneous environment, both the non-treated and modified groups supported cell ingrowth and collagen deposition within the matrix itself with limited peripheral encapsulation.
Figure 13B:
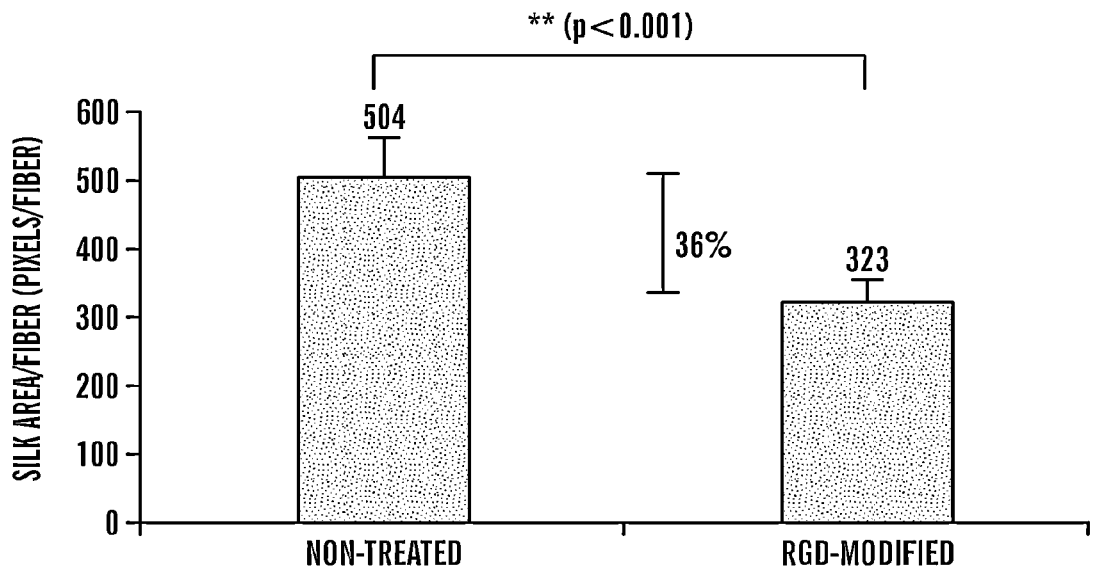
FIG. 13B quantitatively represents a 36% decrease in RGD-modified silk cross-sectional area after 30 days of subcutaneous implantation indicating a significant improvement in the ability of the host to degrade the surface modified silk fibroin matrices compared to non-treated controls.
Figure 13C:
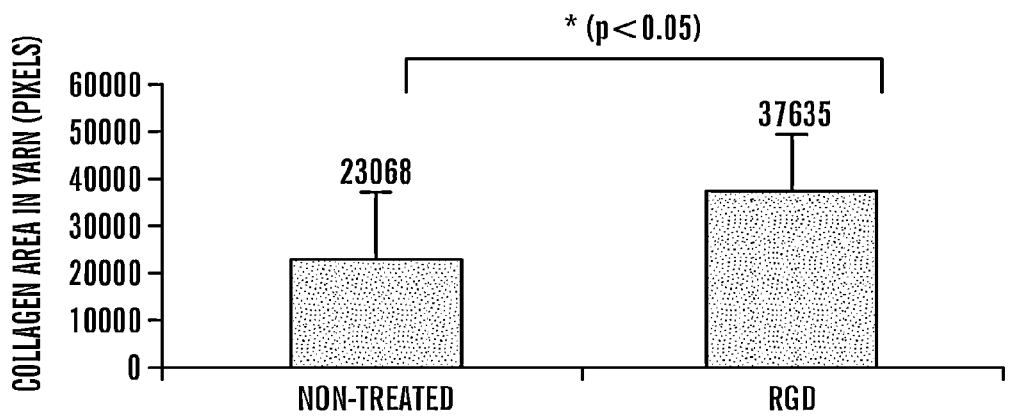
FIG. 13C quantitatively shows a significant 63% increase in collagen deposition within the RGD-modified fibroin matrices as compared to the non-treated controls again demonstrating the ability of the modified silk matrix to support host cell and tissue ingrowth.
Figure 13D:
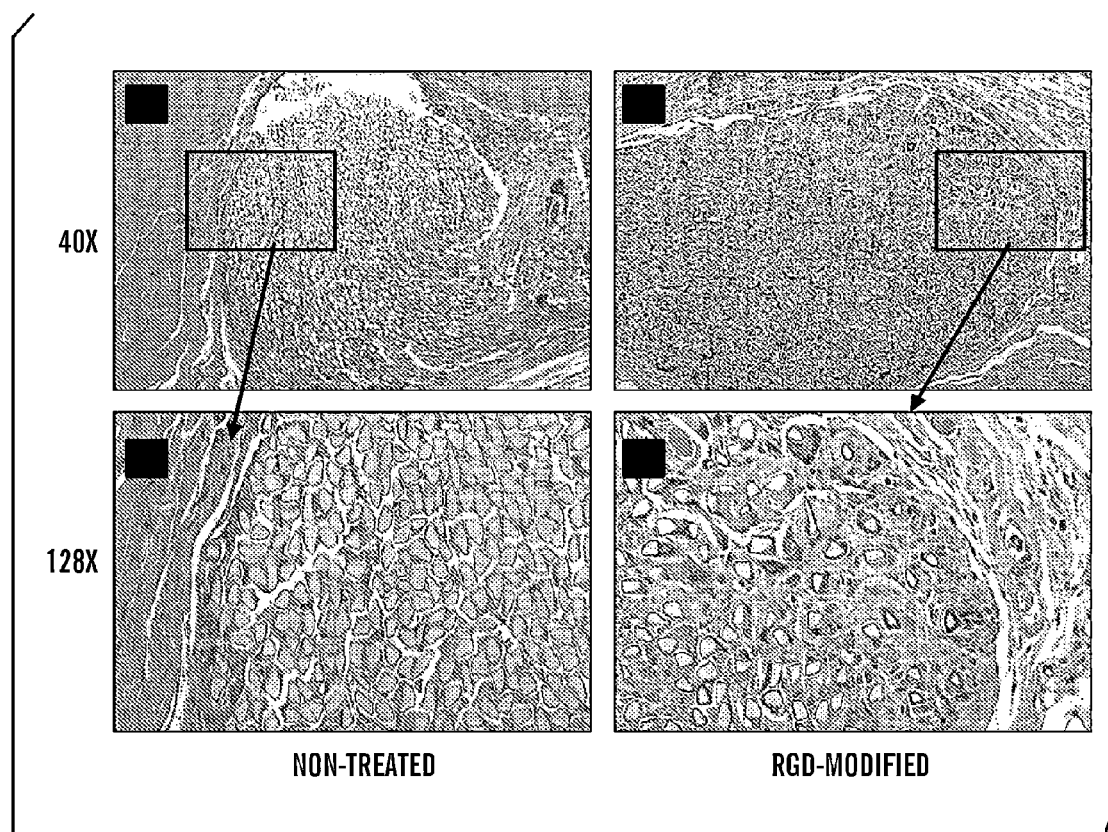
FIG. 13D shows H&E staining of an extracted 36 fiber fibroin yarn implanted intramuscularly in the abdominal was of a Lewis rat. Images are shown at 40× and 128× for both non-modified and RGD-modified matrices. Results show, qualitatively, that RGD-modification dramatically increased cell and tissue infiltration within 30 days in vivo. Unlike black braided silk suture or virgin silk suture, no peripheral encapsulation or plasma cells were observed. Compared to the subcutaneous implants, little to no cell infiltration and collagen deposition was observed in the non-treated controls indicating the effect of implantation site in addition to surface modification.

Numerous applications of fabrics as implants are known in the medical and surgical arts. One example is as a support in hernia repair. For such repair, a fabric, most typically a warp-knit with a desired stitch (e.g., an atlas stitch designed to prevent unraveling of the mesh during cutting), is sewn (or sometimes stapled or glued) or simply laid in place without tensioning, onto the inside of the abdominal wall after it is repaired with conventional sutures. One function of the warp knit fabric is to provide short-term support for the repair. In a preferred embodiment of the present invention, the fibroin fibers within the fabric promote ingrowth of cells and subsequent tissue growth into fabric itself (FIGS. 13A & 13D) as well as through the fabric's interstices formed during knitting and into the region in need of repair. This embodiment aims to permanently strengthen the injured area through functional tissue ingrowth and remodeling as the silk matrix degrades (FIGS. 13A,B & C).

Repair-strengthening fabrics are used in similar situations for repair or support of any part of the abdominal wall, particularly in hernia repair and abdominal floor reconstruction, or in repair or support of other walls and septa in the body, for example of the chest, or of organs such as the heart or the bladder, particularly after surgery or tumor removal. Implantable fabrics can also be used to support bladders or other internal organs (included but not limited to the intestines, the ureters or urethra, and the uterus) to retain them in their normal positions after surgery, damage or natural wear as a result of age or pregnancy, or to position them in an appropriate location. "Organ" here includes both "solid" organs, such as a liver, and tubular organs such as an intestine or a ureter. Fabrics, especially bulky fabrics such as some non-woven types or those that can be created through 3-dimensional knitting or braiding (FIG. 4A-C), can be used to fill cavities left by surgery to provide a fiber construct onto which cells can migrate or to which cells can be pre-attached (e.g. to improve the rate of repair). Usage sites include cavities in both soft tissues and hard tissues such as bone. In other cases, fabrics are used to prevent adhesions, or to prevent the attachment and/or ingrowth of cells; this may be achieved through surface modification of the silk fibroin matrix or through the attachment of a drug or factor to the matrix.

The silk-fibroin-based fabrics of the invention can easily be modified in several ways to enhance healing or repair at the site. These modifications may be used singly or in combination. The silk-fibroin-based fabrics of the invention can be surface modified to support cell attachment and spreading, cell and tissue ingrowth and remodeling, and device biodegradation through the use of RGD peptide coupling or gas plasma irradiation (FIGS. 13A-E). The fabrics can be modified to carry cell-attachment factors, such as the well-known peptide "RGD" (arginine-glycine-aspartic acid) or any of the many natural and synthetic attachment-promoting materials, such as serum, serum factors and proteins including fibronectin, blood, marrow, groups, determinants, etc., known in the literature. Such materials can be in any of the usual biochemical classes of such materials, including without limitation proteins, peptides, carbohydrates, polysaccharides, proteoglycans, nucleic acids, lipids, small (less than about 2000 Daltons) organic molecules and combinations of these. Such plasma modification can improve the fabric's surface functionality and/or charge without affecting the materials bulk mechanical properties. Fabrics can be gas plasma irradiated after sericin extraction without compromising the integrity of the sericin-extracted silk fibroin fibers (Table 9).

Additionally, the fabric can be treated so that it delivers a drug. Attachment of the drug to the fabric can be covalent, or covalent via degradable bonds, or by any sort of binding (e.g., charge attraction) or absorption. Any drug can be potentially used; non-limiting examples of drugs include antibiotics, growth factors such as bone morphogenic proteins (BMPs) or growth differentiation factors (GDFs), growth inhibitors, chemo-attractants, and nucleic acids for transformation, with or without encapsulating materials.

Figure 9A:
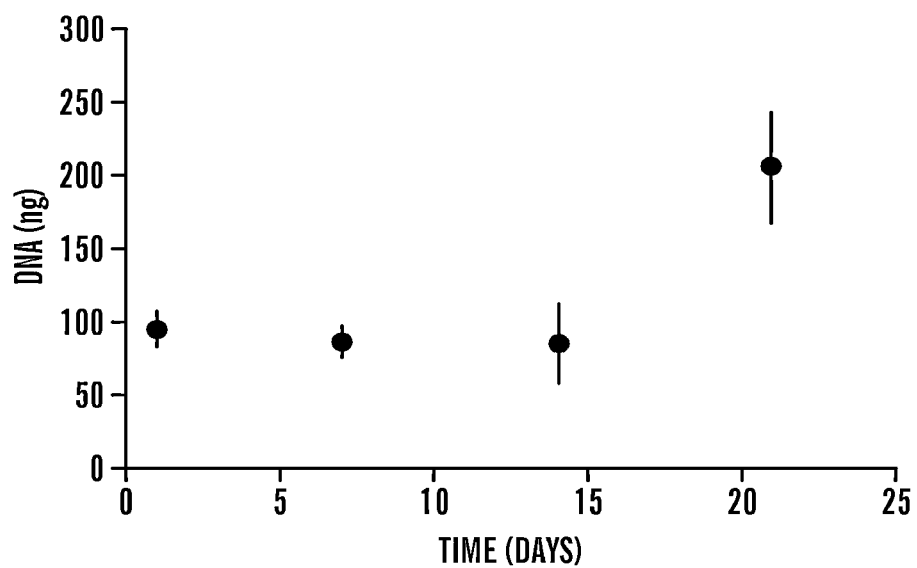
FIG. 9A is a chart illustrating bone marrow stromal cell proliferation on silk fibroin Matrix 1 determined by total cellular DNA over 21 day culture period indicating a significant increase in cell proliferation after 21 days of culture.
Figure 9B:
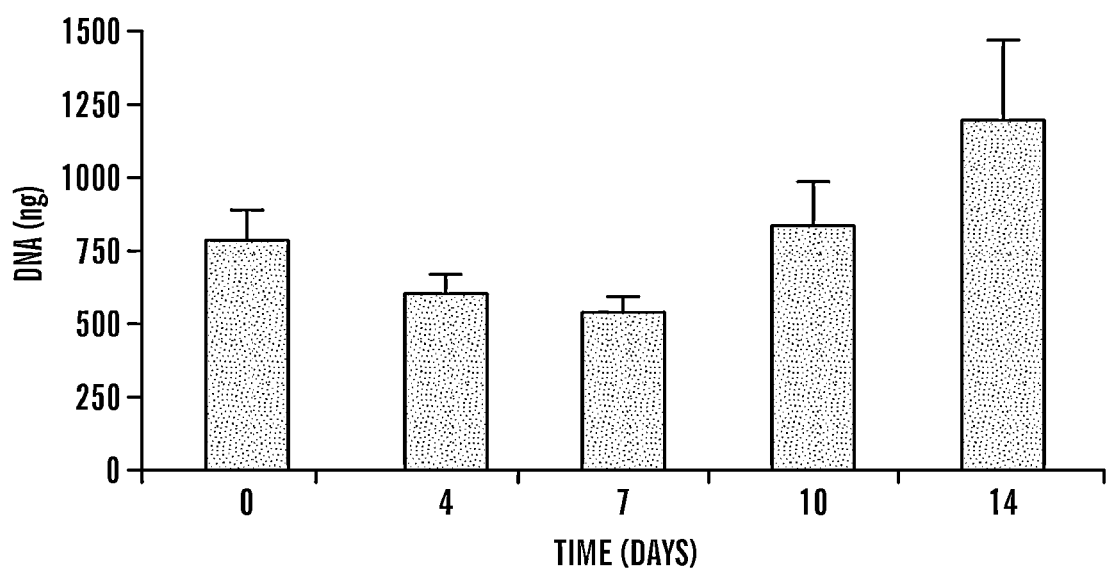
FIG. 9B is a bar graph illustrating bone marrow stromal cell proliferation on silk fibroin Matrix 2 determined by total cellular DNA over 14 day culture period indicating a significant increase in cell proliferation after 14 days of culture.

In another modification, cells can be added to the fabric before its implantation (FIG. 7A-D, FIG. 8A-B, and FIG. 9A-B). Cells can be seeded/absorbed on or into the fabric. Cells can also or in addition be cultivated on the fabric, as a first step towards tissue replacement or enhancement. The cells may be of any type, but allogenous cells, preferably of the "immune protected," immune privileged," or stem cell types are preferred, and autologous cells are particularly preferred. The cells are selected to be able to proliferate into required cell types on or in the fiber construct (FIG. 9A-B).

Figure 16A:
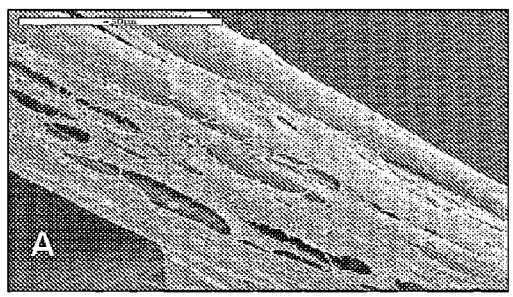
FIGS. 16A, 16B and 16C illustrate bone marrow stromal cells seeded and grown on collagen fibers for 1 day (FIG. 16A) and 21 days (FIG. 16B); RT-PCR (FIG. 16C) and gel electrophoretic analysis of collagen I and III expression vs. the housekeeping gene GAPDH: a=Collagen I, day 14; b=Collagen I, day 18; c=Collagen III, day 14; d=Collagen III, day 18; e=GAPDH, day 14; f=GAPDH, day 18. Collagen type II (as a marker for cartilage) and bone sialoprotein (as a marker of bone tissue formation) were not detected indicating a ligament specific differentiation response.
Figure 16B:
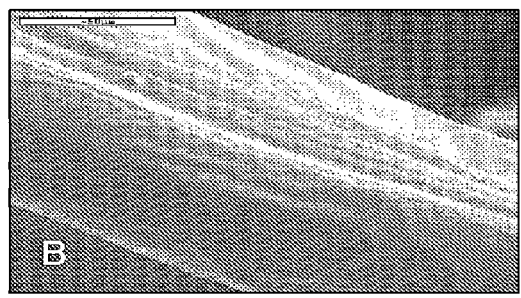
Figure 16C:
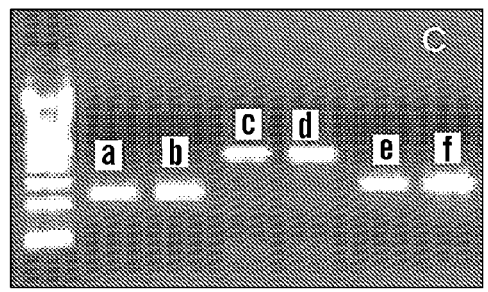

Another class of modification is incorporation of other polymers (e.g. in fiber or gel form) into the fabric, to provide specific structural properties or to modify the native surfaces of the silk fibroin and its biological characteristics (see FIG. 16A-C: seeding of collagen fibers with BMSCs). In one type of incorporation, fibers or yarns of silk and of another material are blended in the process of making the fabric. In another type, the silk-based fibers, yarns or fabrics are coated or over-wrapped with a solution or with fibers of another polymer. Blending may be performed (i) randomly, for example by plying (1 or multiple fibers of) both silk and the polymer together in parallel before twisting or (ii) in an organized fashion such as in braiding where fibers or yarns being input into the larger yarn or fabric can alternate machine feed positions creating a predicable outcome. Coating or wrapping may be performed by braiding or cabling over a central core, where the core can be the polymer, the silk fibroin or a composite of both, depending on the desired effect. Alternatively, one yarn can be wrapped in a controlled fashion over the other polymer, where the wrapping yarn can be used to stabilize the structure. Any biocompatible polymer is potentially usable. Examples of suitable polymers include proteins, particularly structural proteins such as collagen and fibrin, and strength-providing degradable synthetic polymers, such as polymers comprising anhydrides, hydroxy acids, and/or carbonates. Coatings may be provided as gels, particularly degradable gels, formed of natural polymers or of degradable synthetic polymers. Gels comprising fibrin, collagen, and/or basement membrane proteins can be used. The gels can be used to deliver cells or nutrients, or to shield the surface from cell attachment. Further, proteins or peptides can be covalently attached to the fibers or the fibers can be plasma modified in a charged gas (e.g., nitrogen) to deposit amine groups; each of these coatings supports cell attachment and ingrowth, as silk is normally hydrophobic, and these coatings make the fibers more hydrophilic.

Non-limiting examples of some of these embodiments are described in examples, below.

Wet laydown was selected for a prototype of fabric formation because it is the simplest procedure. The non-woven product (FIG. 20A) was created from a single silk fibroin fiber prior to extraction at the fabric level. The product is correspondingly a relatively inexpensive material, and can be used in applications where its low tensile strength would be satisfactory. When more tensile strength is needed, a non-woven material could be bonded together, as is well known for fabrics and paper or mineralized for bone repair. Alternatively, silk yarn material produced by extraction of the sericin can be formed into a variety of more complex yarns, as described above. The size and design of the yarn can be used to control porosity, independent of non-woven machine capabilities. The yarns can also be knit (FIG. 20B) or woven (FIG. 20C) into a fabric. One type of fabric of interest is a simple mesh, similar to gauze, which can be used by itself (e.g. as a hemostat), or to deliver cells or drugs (e.g. a clotting factor) to a site, in a situation where flexibility is important.

When strength is important, a warp knit fabric (FIG. 20B), including the familiar tricots and jerseys, having an elasticity that can be controlled through the helical design of the yarn used in the fabric, and typically substantial tensile strength, can be very useful for applications (e.g., hernia repair, bladder slings, pelvic floor reconstructions, etc.) requiring provision of mechanical support for a significant length of time, such as months.

Figure 20C:
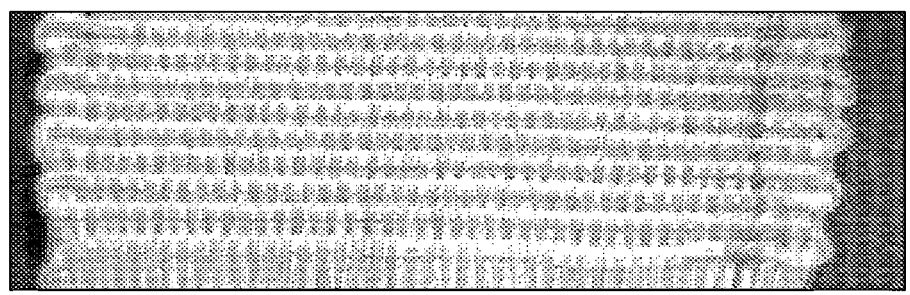

In other applications, the material should have little elasticity and great strength. For such fabrics, a dense weave of thick yarns is appropriate, producing a material similar to standard woven fabrics (FIG. 20C). Such a material can optionally be supplemented by a coating treatment or a heat treatment to bond the crossovers of the yarn segments, thereby preventing both raveling and stretching. Heat treatment must not entirely denature the silk protein. The fabric can optionally be sewn, glued or stapled into place, as is currently done with polypropylene mesh. The implant, like any of the other types discussed, can be coated with various materials to enhance the local healing and tissue ingrowth process, and/or with a coating to prevent adhesion of the repair site to the viscera.

Figure 21:
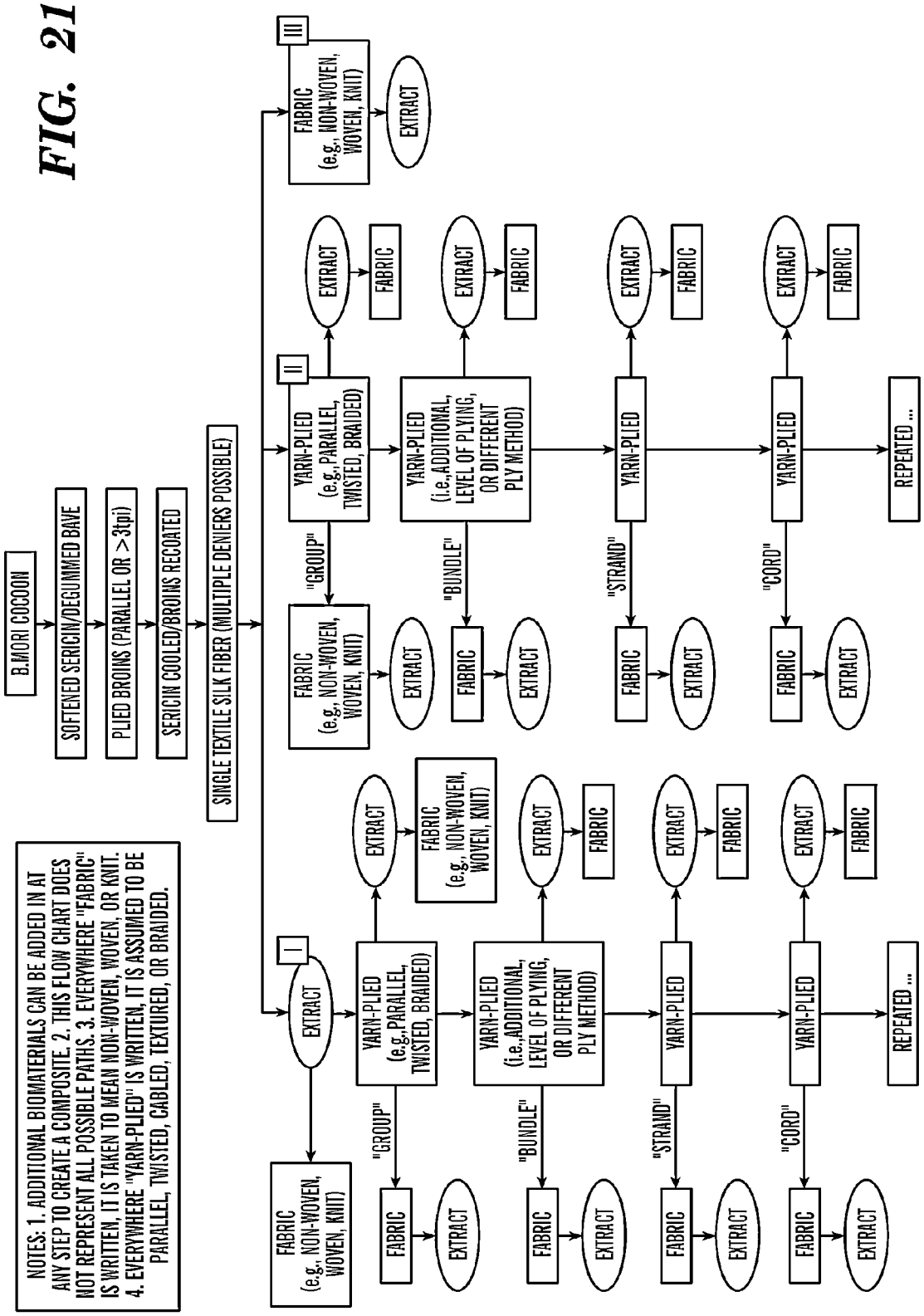
FIG. 21 is a schematic flow chart of the various methods and sequences that can be employed to create a biocompatible and biodegradable silk fibroin matrix. For example, extract single fiber, twist into yarns and knit into fabrics OR ply yarns, twist plied yarns, form fabric and then extract. An almost infinite number of combination exists, but all will be dependent on the hierarchy of the yarn, the number of fibers per level and the TPI per level as shown in Tables 4, 6, 7, and 8.

In another alternative, the fabric, mesh, non-woven, knit or other repair material can be made of unextracted silk, and then the finished fabric can be extracted as described herein (FIG. 21) (for example, with alkaline soap solution at elevated temperature) to remove the immunomodulatory sericins from the material. As a further alternative, the extraction of the sericin can take place at an intermediate stage, such as extraction of the formed yarn, bundle, or strand, in so far as the number of fibers does not exceed that at which the extracting solution can penetrate throughout the fibers (see FIG. 21 for non-limiting options).

The above discussion has described making fabrics composed of yarns, where the most typical form of yarn in the fabric formations discussed about would derive from twisting silkworm fibroin fibers together in an organized manner and extracting sericin. Many yarn geometries and methods of yarn formation may also be used as described (Tables 4, 5, 6, 7 & 8). Such methods may include the formation of non-twisted bundles of fibroin fibers, bound together by wrapping the bundles with silk or another material as discussed above. Any of these yarns could, as described above, be formed by blending silk fibers with other materials. Further still, the fibers can be intertwined, e.g., cabled, twisted, braided, meshed, knitted, etc. (see FIGS. 2A&B and 21). The term, "intertwined," is used herein to indicate an organized (i.e., non-random) repeating structure in terms of how the fibers contact and bind one another.

Figure 11A:
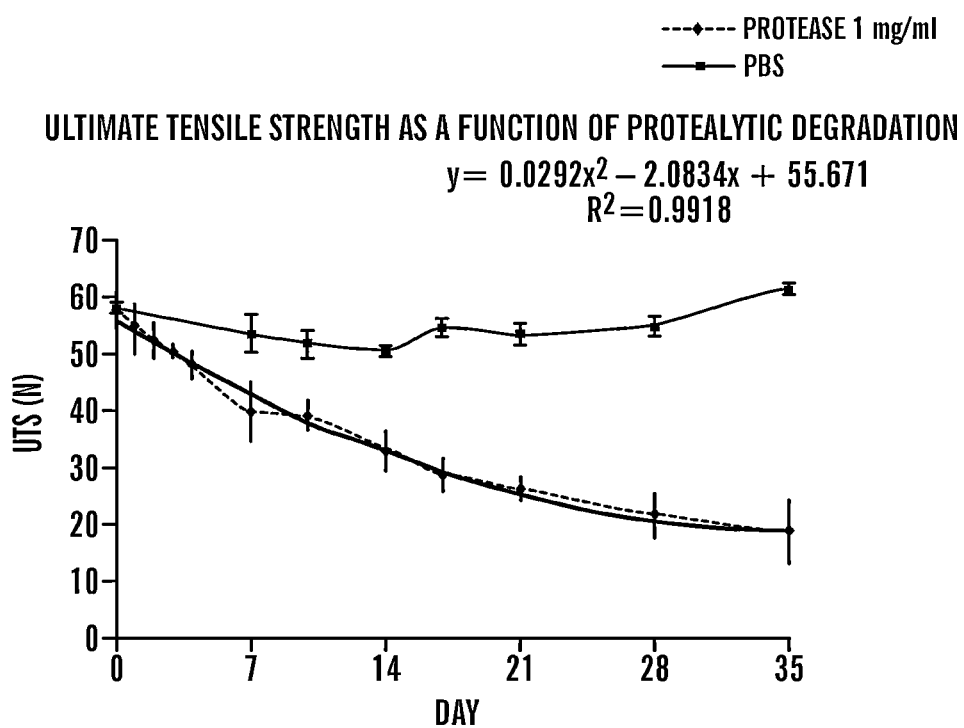
FIG. 11A is a chart of UTS as a function of in vitro enzymatic degradation; no strength loss was observed in the negative control, PBS. Silk lost 50% of its strength after 21 days in culture. A 1 mg/ml solution of Protease XIV from Sigma was used.
Figure 11B:
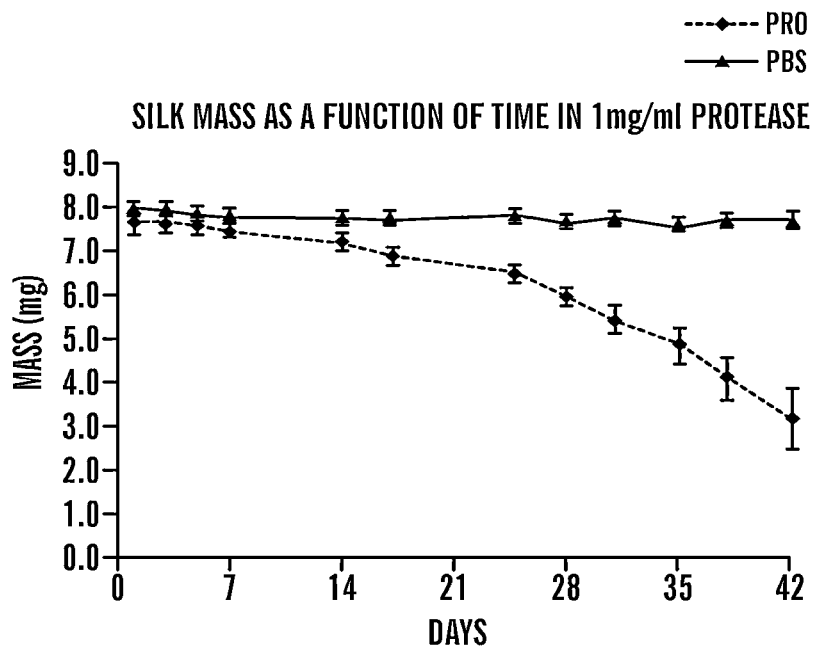
FIG. 11B is a chart of mass loss as a function of in vitro enzymatic degradation; no strength loss was observed in the negative control, PBS. 50% mass loss was observed after 41 days in culture.
Figure 12:
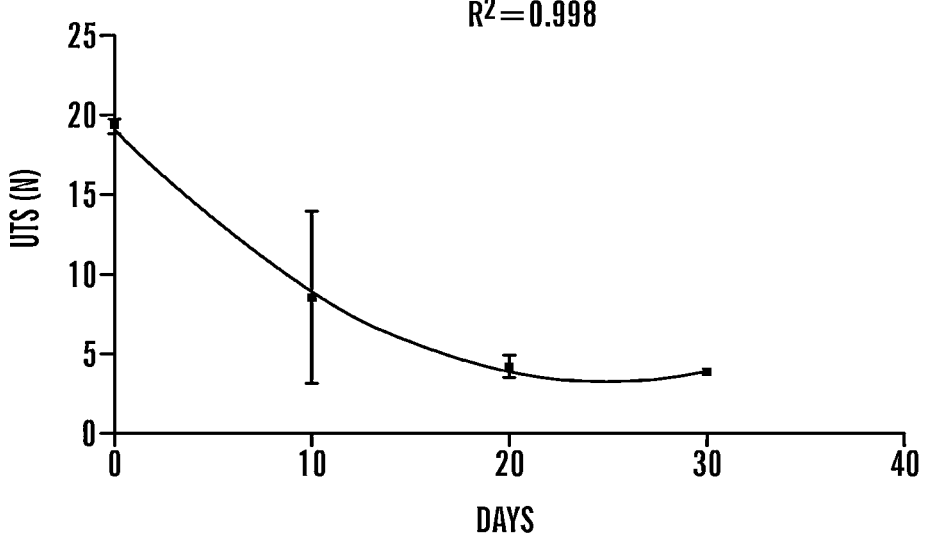
FIG. 12 is a chart of UTS loss as function of in vivo degradation following RGD-modified matrix implantation into a non-loaded subcutaneous rat model for 10, 20 and 30 days. 50% strength loss was observed after ~10 days in vivo in a non-loaded environment.

Blending could also be done at higher levels of organization, such as the use of filaments of different materials to form a thicker yarn, or using yarns of differing materials in weaving or knitting. In each case, the final material would include purified, essentially sericin-free silk as a significant component, used for one or all of its strength and biocompatibility and (e.g., long-term) degradation characteristics (FIG. 11A-B). The other polymer or polymers are selected for their biocompatibility, support (or inhibition through rapid tissue formation at desired locals) of cell attachment or infiltration (FIG. 16A-C), degradation profile in vivo, and mechanical properties. Biodegradable polymers include any of the known biodegradable polymers, including natural products such as proteins, polysaccharides, glycosaminoglycans, and derivatized natural polymers, e.g., celluloses; and biodegradable synthetic polymers and copolymers including polyhydroxy acids, polycarbonates, polyanhydrides, some polyamides, and copolymers and blends thereof. In particular, collagen and elastin are suitable proteins.

Silk-containing fabric constructs/matrices used for tissue repair may be treated so that they contain cells at the time of implantation (FIG. 7A-D, FIG. 8A-B, FIG. 9A-B, & FIG. 18C) to improve tissue outcomes in vivo. The cells may be xenogenic, more preferably allogenic, and most preferably autologous. Any type of cell is potentially of use, depending on the location and the intended function of the implant. Pluripotent cells are preferred when the appropriate differentiation cues are present or provided in the environment. Other cell types include osteogenic cells, fibroblasts, and cells of the tissue type of the implantation site.

Figure 18A:
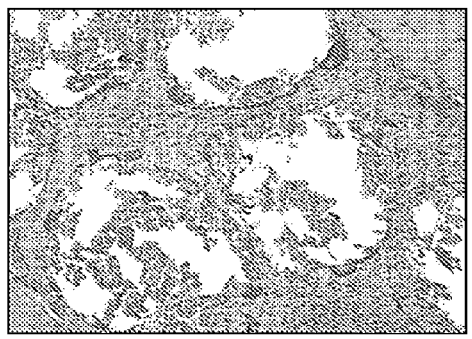
FIG. 18A and FIG. 18B are H&E stained cross-sections of 6 bundles of (A) 2-0 black braided silk suture and (B) RGD-surfaced modified silk (36 fibers/bundle), respectively, 30 days following intra-muscular implantation. 18C is RGD-modified silk pre-seeded with BMSCs for 4 weeks prior to implantation.
Figure 18B:
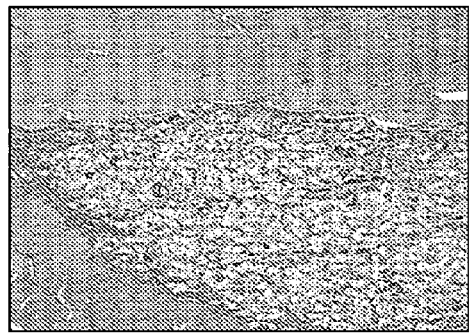

While silk from *Bombyx mori* and other conventional silkworms has been described, any source of silk or silk-derived proteins can be used in the invention, as long as it provokes no more than a mild foreign body reaction on implantation (i.e., is biocompatible) (see FIGS. 18B &C). These include without limitation silks from silkworms, spiders, and cultured cells, particularly genetically engineered cells, and transgenic plants and animals. Silk produced by cloning may be from full or partial sequences of native silk-line genes, or from synthetic genes encoding silk-like sequences.

While in many cases only a single fabric type will be used in formation of a medical device or prosthesis, it may be useful in some cases to use two or more types of fabric in a single device. For example, in hernia repair, it is desirable to have the tissue-facing side of the repair fabric attract cells, while the peritoneal face should repel cells, to prevent adhesions. This effect can be achieved by having one layer of silk that does not attract cells, and another layer that does (for example, an untreated layer and an RGD-containing layer, as in the example, below). Another example includes formation of a bladder sling. The basic sling should be conforming and somewhat elastic, and have a long projected lifetime. However, the face of the sling closest to the bladder should have as little texture as feasible. This can be accomplished by placing a layer of thin but tightly woven, non-woven or knitted fabric, fabricated from a yarn having a small diameter (e.g., a single fiber), of the invention in the sling where it will contact the bladder. The non-woven fabric should be of as small a gauge (denier) as feasible. Numerous other situations needing two or more types of fabric are possible.

Examples of the above-described structures were fabricated and evaluated in a series of tests. In a first example, a fabric was formed from purified silk fibrils. First, raw silk was processed into purified fibroin fibrils. Raw silkworm fibers were extracted in an aqueous solution of 0.02 M $Na_2CO_3$ and 0.3% w/v IVORY soap solution for 60 minutes at 90 degrees C. The extracted fibers were rinsed with water to complete the extraction of the glue-like sericin protein. The resulting suspension of fibrils was wet-laid on a screen, needle-punched, and dried (FIG. 20A). The resulting fleecy material felt somewhat like wool to the touch, and was very porous. It was sufficiently interbonded by entanglement and needling that it was easily handled and cut to a desired shape.

Figure 18C:
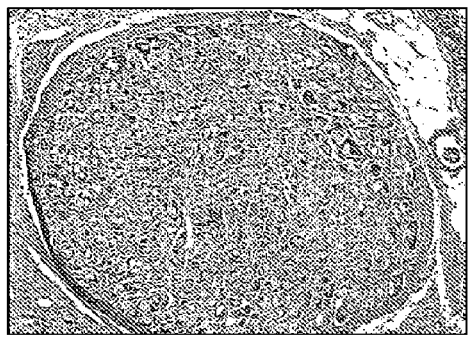
Figure 19A:
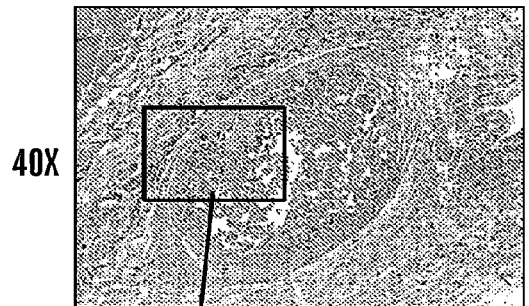
FIGS. 19A-D shows H&E stained cross sectional images at 40× (top row, FIG. 19A & FIG. 19B) and 128× (bottom row, FIGS. 19C and 19D) of two yarns (4×3×3 and 12×3), each containing the same number of fibers, but organized differently with specific hierarchies following implantation in a rat model for 30 days. Results indication that yarn design and structure can influence the extent of cell and tissue ingrowth as the 12×3 yarn construct allowed for ingrowth, while it appears the 4×3×3 thwarted it.
Figure 19B:
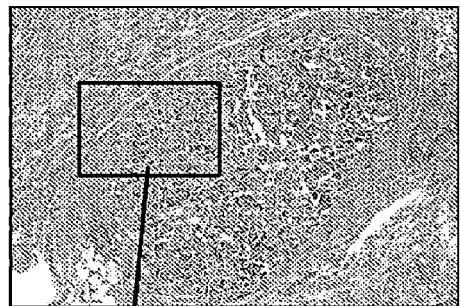
Figure 19C:
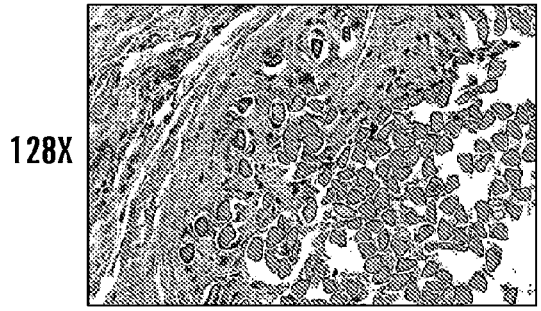
Figure 19D:
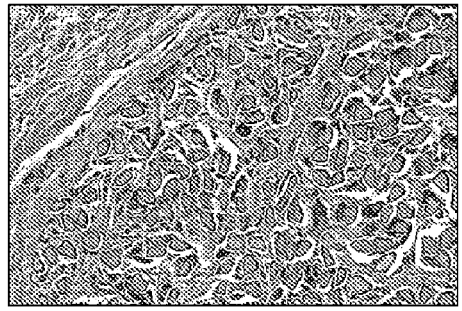

In another example, the purified silk fibroin fibrils were treated with cell attracting agents (Table 9). First, yarns were made by twisting purified fibers of silk fibroin together. Some yarns were made of filaments that were derivatized with the peptide RGD to attract cells, using procedures described in Sofia et al, J. Biomed. Mater. Res. 54: 139-148, 2001. Sections of treated and untreated (black braided silk suture) yarns were implanted in the abdominal wall of rats (FIG. 18A-C). After 30 days of implantation, the black braided sutures contained compact fibril bundles, with cell infiltration between fibril bundles but not within them. In contrast, the RGD treated fibril bundles were extensively invaded by host cells, and were expanded and non-compact (FIG. 13A-E, 18B), but were not yet significantly degraded (FIG. 13A-E).

This example illustrates the use of derivatization to control the rate of degradation of implanted silk fibroin fibrils, as well as demonstrating the ability of derivatized fibrils to recruit cells to a fabric-like structure. Clearly, greater specificity of recruitment can be obtained by using a more specific attractant. Similar techniques (chemical derivatization) or simpler methods such as absorption, adsorption, coating, and imbibement, can be used to provide other materials to the implantation site.

Each of the samples reported in the Tables below, was prepared in accordance with the above description, wherein sericin was removed over 60 minutes at a temperature of 90°+/−2° C. Using a temperature in this range for a sufficient period of time has been found to produce fibers from which sericin is substantially removed (FIG. 1A-C, Table 1, 2, 3) (to produce a fiber construct that is substantially free of sericin so as not to produce a significant immunological response and not to significantly impede the biodegradability of the fiber) while substantially preserving the mechanical integrity of the fibroin (Table 1). Note that when temperatures reach 94° C. (Table 1), UTS was not dramatically affected; however, stiffness significantly declined indicating a silk thermo sensitive at temperatures of 94° C. and above. The fibers in each group were manually straightened (i.e., made parallel) by pulling the ends of the fibers; alternatively, straightening could easily have been performed via an automated process. The force applied was marginally greater than what was required to straighten the group.

The sample geometry designations in all Tables reflect the following constructs: # of fibers (tpi at fiber level in S direction)×# of groups (tpi at group level in Z direction)×# of bundles (tpi at bundle level in S direction)×# of strand (tpi at stand level in Z direction)×etc., wherein the samples are twisted between levels unless otherwise indicated. The twist-per-inch designation, such as 10s×9z tpi, reflects (the number of twists of the fibers/inch within the group)×(the number of twists of the groups/inch within the bundle). In each sample, the pitch of the twist is substantially higher than is ordinarily found in conventional yarns that are twisted at a low pitch intended merely to hold the fibers together. Increasing the pitch of the twists (i.e., increasing the twists per inch) decreases the tensile strength, but also further decreases the stiffness and increases the elongation at break of the construct.

Figures 5A, 5B:
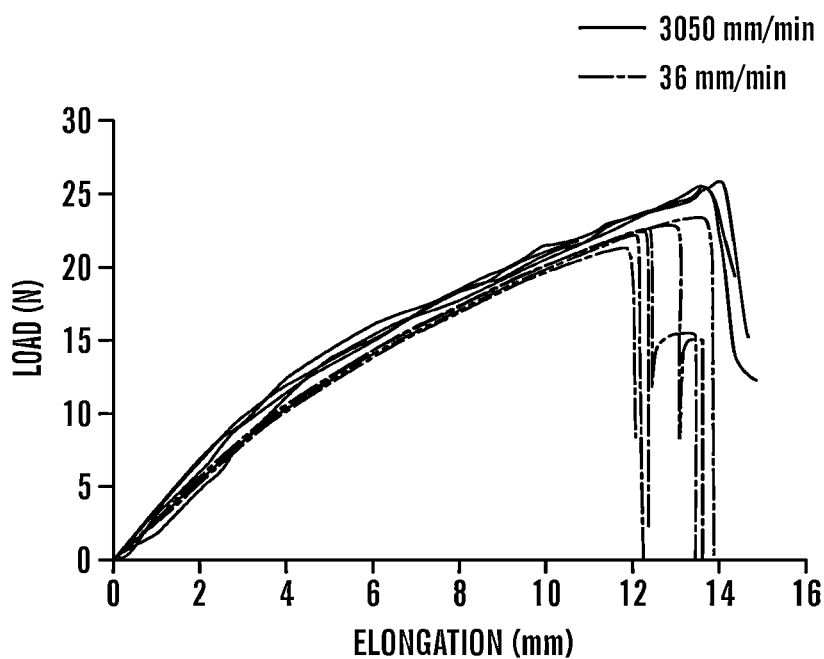
FIG. 5A provides strength and stiffness data for a 36 fiber yarn as a function of 6 different strain rates at which they were tested (N=5 per group).
FIG. 5B shows load-elongation curves for a 36-fiber yarn, 3 cm long, tested at 2 of the 6 different strain rates. The data represents the effect of the testing procedures (here, specifically strain rate) on the reported mechanical properties (e.g. UTS) of the yarn structure.
Figure 6A:
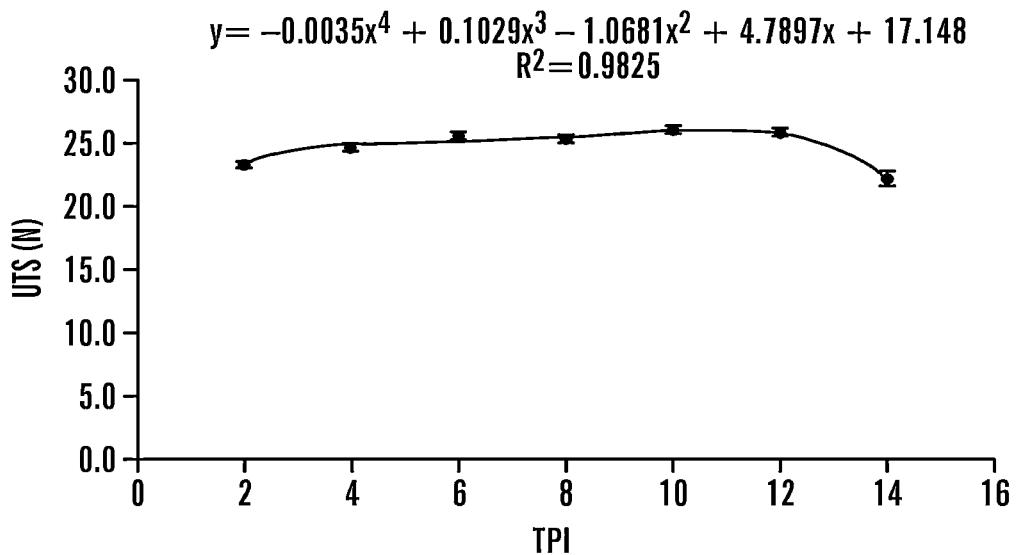
FIG. 6A is a chart of UTS as a function of twists per inch (TPI); trend lines were generated to extrapolate data to a $4^{th}$ order polynomial—TPIs from 0-15 are shown. A maximum was observed indicating an ordered structure where individual filaments are working in unison.
Figure 6B:
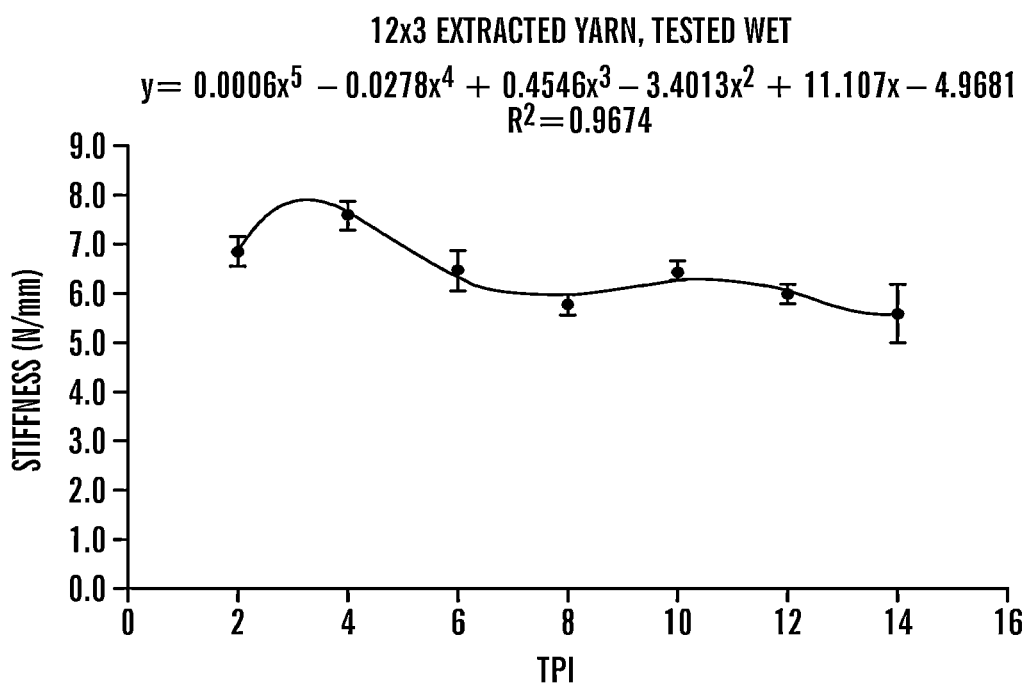
FIG. 6B is a chart of stiffness (for a 3 cm length sample) as a function of twists per inch (TPI); trend lines were generated to extrapolate data to a $5^{th}$ order polynomial—TPIs from 0-15 are shown. A maximum was observed indicating that TPI could be used as a tool to design for a specific UTS or stiffness.

The ultimate tensile strength (UTS), percent elongation at break (% Elong), and stiffness were all measured using an INSTRON 8511 servohydraulic material testing machine with FAST-TRACK software, which strained the sample at the high rate of ~100% sample length per second in a pull-to-failure analysis. In other words, up to the point of failure, the sample is stretched to double its length every second, which greatly restricts the capacity of the sample to relax and rebound before failure. However, FIG. 5A-B demonstrates the effect of strain rate can have on observed mechanical properties as well as wet or dry testing conditions which were shown (FIG. 6A-B) to have a dramatic effect on silk matrix UTS and stiffness. Consistency is needed if comparisons are to be made between data sets. The resulting data was analyzed using Instron Series IX software. Ultimate tensile strength is the peak stress of the resulting stress/strain curve, and stiffness is the slope of the stress/strain plot up to the yield point. Unless specified, at least an N=5 was used for all tested groups to generate averages and standard deviations. Standard statistical methods were employed to determine if statistically significant differences existed between groups, e.g., Student's t-test, one-way ANOVA.

The fibroin fibers in the samples in all of the above Tables and Figures (and throughout this disclosure) are native (i.e., the fibers are not dissolved and reformed); dissolution and reformulation of the fibers results in a different fiber structure with different mechanical properties after reforming. Surprisingly, these samples demonstrate that yarns of silk fibroin fibers, from which sericin has been completely or nearly completely removed, can possess high strengths and other mechanical properties that render the yarns suitable for various biomedical applications (Table 4, FIG. 2A-D & FIG. 20A-C), such as for forming a fiber construct or support for ligament replacement, hernia repair or pelvic floor reconstruction. Previously, it was believed that fibroin needed to be dissolved and extruded into a reformulated fiber to provide desired mechanical properties. Fatigue strength has generally been found to suffer in such reformed fibroin fibers. The methods of the present invention, allow for sericin removal without a significant loss of strength (Tables 1 & 4; FIGS. 3A-D & 4A-B).

In Table 8, samples 1 and 2 compare the properties of a 3-fiber group (sample 1) with those of a 4-fiber group (sample 2). Sample 2 had a square configuration of fibers, while the fibers of sample 1 had a triangular configuration. As shown in the Table, the addition of the extra fiber in sample 2 lowered the per-fiber stiffness of the sample demonstrating the ability to control yarn and fabric properties through hierarchical design.

Table 4 illustrates the effects of different configurations of cabled-fiber constructs and a twisted-fiber geometry. Note, in particular, samples 7 and 8 include the same number of fibers and the same number of geometrical levels. The twisted-fiber geometry of sample 8 offers greater UTS and greater stiffness, while the cabled geometry of sample 7 has lower strength and lower stiffness. Of samples 7-9, the cabled geometry of sample 7 has the highest strength-to-stiffness ratio; for use as an ACL fiber construct, a high strength-to-stiffness ratio is desired (i.e., possessing a high strength and low stiffness).

Tables 1 and 4 demonstrate the effect of sericin extraction on the fibers. All samples were immersed in an extraction solution, as described in Table 1. Samples 1-5 were immersed in a bath at room temperature, at 33° C. and 37° C. These temperatures are believed to be too low to provide significant sericin extraction. Samples 6-9 were extracted at 90° C., where complete sericin extraction is believed to be attainable, but for varying times. Similarly sample 10 was extracted at the slightly higher temperature of 94° C. The data suggests that 30 to 60 min at 90° C. is sufficient to significantly remove sericin (see Tables 2&3) and that 94° C. may be damaging the protein structure of silk as shown by a dramatic decrease in stiffness.

Finally, samples 11 to 16 have comparable cabled geometries; the fibers of samples 12, 14, and 16 were extracted, whereas the fibers of samples 11, 13, and 15 were not. As can be seen in the Table, the extraction appears to have had little effect on (high) ultimate tensile strengths per fiber.

The fibers of sample 10 of Table 4 were subject to a curl-shrinking procedure, wherein the fibers were twisted in one direction and then in the opposite direction, rapidly; the fibers where then heated to lock in the twist structure and tested non-extracted. The strength and stiffness of the resulting yarn were comparatively lower than most of the other non-extracted yarns tested. However, Tables 6&7 show the fibroins remarkable ability, post extraction, to withstand up to 30 TPI. Table 6 shows the ordering effect TRI has on silk matrices likely due to the ordering of the multifilament structure following extraction.

Figure 10:
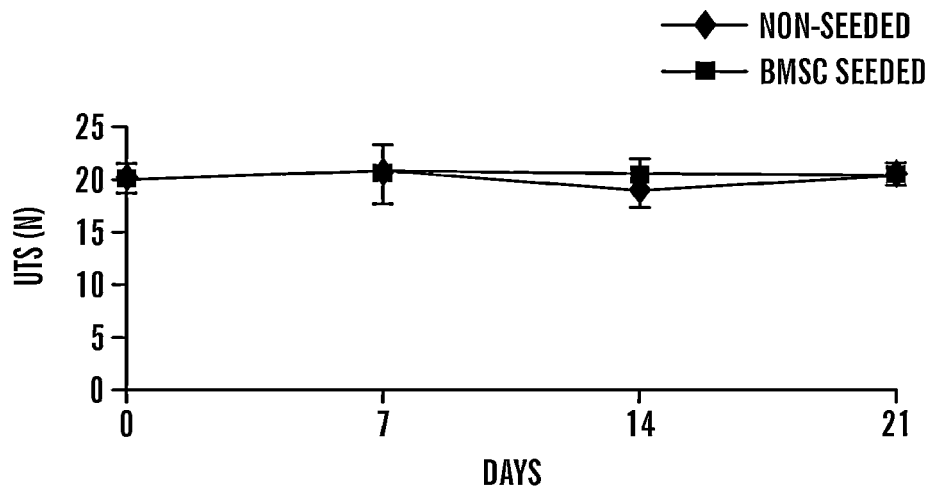
FIG. 10 illustrates the ultimate tensile strength of a 30 silk fiber extracted construct that is either seeded with bone marrow stromal cells or non-seeded over 21 days of culture in physiological growth conditions.

FIG. 10 demonstrates the properties of a group of 30 parallel fibroin fibers seeded and non-seeded in culture conditions for 21 days. These three samples exhibited very similar mechanical properties, thereby reflecting little if any degradation of silk matrices due to cell growth thereon or due to time in vitro. Stiffness values are likely much lower in this experiment in comparison with the other samples as a result of the 21 day wet incubation prior to mechanical testing (see Table 5).

Table 4, samples 14-16 are all braided samples. The fibers of sample 14 were braided from eight carriers, with a spool mounted on each carrier, wherein two fibers were drawn from each spool. The fibers of sample 15 were drawn from 16 carriers, with a spool mounted on each carrier; again, two fibers were drawn from each spool. Finally, sample 16 was formed from 4 yarns, each yarn comprising 3 twisted groups of four fibers (providing a total of 12 fibers per yarn); each of the yarns was drawn from a separate spool and carrier.

Table 9 demonstrates the effect of surface modification. The designation, "PBS," reflects that the samples were immersed in a phosphate-buffered saline solution for about 24 hours before testing. The effect of exposing the samples to the saline solution was measured and provided an indication that the fiber construct can maintain its mechanical properties and substantially preserve the inherent protein structure in a saline environment (e.g., inside a human body). The "RGD" designation reflects that the samples were immersed in an arg-gly-asp (RGD) saline solution for about 24 hours before testing. RGD can be applied to the construct to attract cells to the construct and thereby promote cell growth thereon. Accordingly, any effect of RGD on the mechanical properties of the construct is also of interest, though no significant degradation of the construct was apparent. Accordingly, these samples offer evidence that prolonged exposure to a saline solution or gas ethylene oxide sterilization or to an RGD solution results in little, if any, degradation of the material properties of the fiber constructs. Though, the data associated with samples 28 and 29, wherein the geometrical hierarchy was extended to a higher level, reveal that the UTS/fiber drops as higher levels (and increased overall fiber count) are reached. This is an effect of hierarchical design (Table 8) rather than surface modification.

Table 4, samples 18 through 23 were tensioned under 6 pounds of constant force for 1, 2, 3, 4, 5 and 6 days, respectively, before testing to evaluate the effect of tension on the mechanical properties over time. From the data, there does not appear to be much if any change in the material properties of the construct as the pretension procedure is extended over longer periods of time. Sample 25 was also "pre-tensioned" (after twisting) at 6 pounds force for a day before testing; for comparison, sample 24, which had an identical geometrical configuration was not pre-tensioned. Samples 24 and 25 accordingly reveal the effect of pre-tensioning the construct to remove the slack in the structure, which results in a slight reduction in both the construct's UTS and its elongation at break.

The silk-fiber-based construct serves as a matrix for infiltrating cells or already infiltrated or seeded with cells, such as progenitor, ligament or tendon fibroblasts or muscle cells, which can proliferate and/or differentiate to form an anterior cruciate ligament (ACL) or other desired tissue type. The novel silk-fiber-based construct is designed having fibers in any of a variety of yarn geometries, such as a cable, or in an intertwined structure, such as twisted yarn, braid, mesh-like yarn or knit-like yarn. The yarn exhibits mechanical properties that are identical or nearly identical to those of a natural tissue, such as an anterior cruciate ligament (see Table 4, 1, infra); and simple variations in fiber construct organization and geometry can result in the formation of any desired tissue type (see Table 10, infra). Alternatively, a plurality of yarns can be formed into a fabric or other construct that is implanted to position or support an organ. Additionally, the construct can be used to fill internal cavities after surgery or to prevent tissue adhesions or promote the attachment or ingrowth of cells.

Pluripotent bone marrow stromal cells (BMSCs) that are isolated and cultured as described in the following example can be seeded on the silk-fiber construct and cultured in a bioreactor under static conditions. The cells seeded onto the fiber construct, if properly directed, will undergo ligament and tendon specific differentiation forming viable and functional tissue. Moreover, the histomorphological properties of a bioengineered tissue produced in vitro generated from pluripotent cells within a fiber construct are affected by the direct application of mechanical force to the fiber construct during tissue generation. This discovery provides important new insights into the relationship between mechanical stress, biochemical and cell immobilization methods and cell differentiation, and has applications in producing a wide variety of ligaments, tendons and tissues in vitro from pluripotent cells.

Figure 2C:
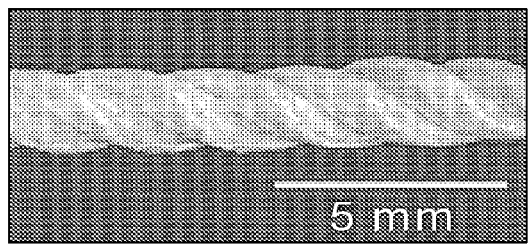
FIG. 2C illustrates a single cord of yarn having a geometry that is helically organized about a central axis and composed of two levels of twisting hierarchy. When six cords are used in parallel (e.g., Matrix 1), the yarn has mechanical properties similar to a native ligament.
Figure 2D:
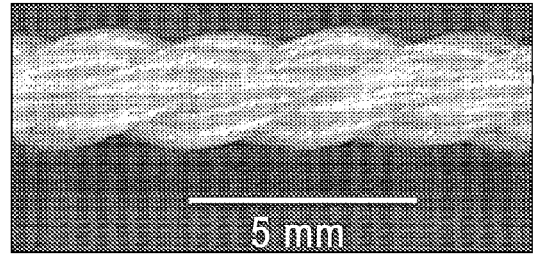
FIG. 2D illustrates a single cord of yarn having a geometry that is helically organized about a central axis and composed of three levels of twisting hierarchy. When six cords are used in parallel (e.g., Matrix 2), the matrix has mechanical properties similar to a native ligament.

A fiber construct comprising silk fibers having a cable geometry, is illustrated in FIGS. 2C and 2D. The fiber construct comprises a hierarchy in terms of the way that fibers are grouped in parallel and twisted and how the resultant group is grouped and twisted, etc., across a plurality of levels in the hierarchy, as is further explained, below. The silk fibers are first tensioned in parallel using, for example, a rack having spring-loaded clamps that serve as anchors for the fibers. The rack can be immersed in the sericin-extraction solution so that the clamps can maintain a constant tension on the fibers through extraction, rinsing and drying.

The extraction solution can be an alkaline soap solution or detergent and is maintained at about 90° C. The rack is immersed in the solution for a period of time (e.g., at least 0.5 to 1 hr, depending on solution flow and mixing conditions) that is sufficient to remove all (+/−0.4% remaining, by weight) or substantially all sericin (allowing for possible trace residue) from the fibers. Following extraction, the rack is removed from the solution and the fibers are rinsed and dried. Computer-controlled twisting machines, each of which mounts the fibers or constructs of fibers about a perimeter of a disc and rotates the disc about a central axis to twist the fibers (i.e. cabling) or constructs of fibers twisted about each other according to standard processes used in the textile industry, though at a higher pitch rate for the twists (e.g., between about 0 and about 11.8 twists per cm) than is typically produced in traditional yarns. The cabling or twist rate, however, should not be so high as to cause plastic deformation of the fibers as a result of the balloon tension created as the yarn is let-off from the feed spool prior to twisting or cabling.

Extraction can be performed at any level of the construct provided that the solution can penetrate through the construct to remove the sericin from all fibers. It is believed that the upper limit for the number of fibers in a compact arrangement that can still be fully permeated with the solution is about 20-50 fibers. Though, of course, those fibers can be arranged as one group of 20 parallel fibers or, for example, as 4 groups of 5 parallel fibers, wherein the groups may be twisted, or even a construct comprising a still higher level such as 2 bundles of 2 groups of 5 fibers, wherein the groups and bundles may be twisted. Increasing the number of hierarchical levels in the structure can also increase the void space, thereby potentially increasing the maximum number of fibers from which sericin can be fully extracted from 20 to 50 fibers.

Because the sericin, in some cases, is removed from the construct after fibers are grouped or after a higher-level construct is formed, there is no need to apply wax or any other type of mechanically protective coating on the fibers or in order to also form a barrier to prevent contact with sericin on the fibers; and the construct can be free of coatings, altogether (particularly being free of coatings that are not fully degraded by the body or cause an inflammatory response).

As described in the examples below, mechanical properties of the silk fibroin (as illustrated in FIGS. 1A, 1B and 1C) were characterized, and geometries for forming applicable matrices for ACL engineering were derived using a theoretical computational model (see FIG. 1D). A six-cord construct was chosen for use as an ACL replacement to increase matrix surface area and to enhance support for tissue in-growth. Two construct geometrical hierarchies for ACL repair comprise the following:

Matrix 1:1 ACL yarn=6 parallel cords; 1 cord=3 twisted strands (3 twists/cm); 1 strand=6 twisted bundles (3 twists/cm); 1 bundle=30 parallel washed fibers; and Matrix 2: 1 ACL yarn=6 parallel cords; 1 cord=3 twisted strands (2 twists/cm); 1 strand=3 twisted bundles (2.5 twists/cm); 1 bundle=3 groups (3 twists/cm); 1 group=15 parallel extracted silk fibroin fibers.

The number of fibers and geometries for Matrix 1 and Matrix 2 were selected such that the silk prostheses are similar to the ACL biomechanical properties in ultimate tensile strength, linear stiffness, yield point and % elongation at break, serving as a solid starting point for the development of a tissue engineered ACL. The effects of increasing number of fibers, number of levels, and amount of twisting on each of these biomechanical properties are shown in Table 8 and Tables 6&7, respectively.

The ability to generate two matrices with differing geometries both resulting in mechanical properties that mimic properties of the ACL indicates that a wide variety of geometrical configurations exist to achieve the desired mechanical properties. Alternative geometries for any desired ligament or tendon tissue may comprise any number, combination or organization of cords, strands, bundles, groups and fibers (see Table 10, infra) that result in a fiber construct with applicable mechanical properties that mimic those of the ligament or tendon desired. For example, one (1) ACL prosthesis may have any number of cords in parallel provided there is a mean for anchoring the final fiber construct in vitro or in vivo. Further, various numbers of twisting levels (where a single level is defined as a group, bundle, strand or cord) for a given geometry can be employed provided the fiber construct results in the desired mechanical properties. Furthermore, there is a large degree of freedom in designing the fiber construct geometry and organization in engineering an ACL prosthesis; accordingly, the developed theoretical computational model can be used to predict the fiber construct design of a desired ligament or tendon tissue (see the example, below). For example when multiple smaller matrix bundles are desired (e.g., 36 fibers total) with only two levels of hierarchy to promote ingrowth, a TPI of 8-11 or ~3-4 twists per cm is required and can be predicted by the model without the need for empirical work.

Consequently, a variation in geometry (i.e., the number of cords used to make a prosthesis or the number of fibers in a group) can be used to generate matrices applicable to most ligaments and tendons. For example, for smaller ligaments or tendons of the hand, the geometry and organization used to generate a single cord of Matrix 1 (or two cords or three cords, etc.) may be appropriate given the fiber construct's organization results in mechanical properties suitable for the particular physiological environment. Specifically, to accommodate a smaller ligament or tendon compared to Matrix 1 or Matrix 2, less fibers per level would be used to generate smaller bundles or strands. Multiple bundles could then be used in parallel. In the case of a larger ligament such as the ACL, it might be desirable to have more smaller bundles twisted at higher TPIs to reduce stiffness and promote ingrowth then to have fewer larger bundles where ingrowth cannot occur thereby limited degradation of the matrix.

The invention is not, however, limited with respect to the cable geometry as described, and any geometry or combination of geometries (e.g., parallel, twisted, braided, mesh-like) can be used that results in fiber construct mechanical properties similar to the ACL (i.e., greater than 2000 N ultimate tensile strength, between 100-600 N/mm linear stiffness for a native ACL or commonly used replacement graft such as the patellar tendon with length between 26-30 mm) or to the desired ligament and tendon that is to be produced. The number of fibers and the geometry of both Matrix 1 and Matrix 2 were selected to generate mechanically appropriate ACL matrices, or other desired ligament or tendon matrices [e.g., posterior cruciate ligament (PCL)]. For example, a single cord of the six-cord Matrix 1 construct was used to reconstruct the medial collateral ligament (MC) in a rabbit (see FIG. 15A and FIG. 15B). The mechanical properties of the silk six-cord constructs of Matrix 1 and Matrix 2 are described in Table 10 and in FIGS. 3A-3D, as is further described in the example, infra. Additional geometries and their relating mechanical properties are listed in Table 11 as an example of the large degree of design freedom that would result in a fiber construct applicable in ACL tissue engineering in accordance with methods described herein.

Advantageously, the silk-fiber based fiber construct can consist solely of silk. Types and sources of silk include the following: silks from silkworms, such as *Bombyx mori* and related species; silks from spiders, such as *Nephila clavipes*; silks from genetically engineered bacteria, yeast mammalian cells, insect cells, and transgenic plants and animals; silks obtained from cultured cells from silkworms or spiders; native silks; cloned full or partial sequences of native silks; and silks obtained from synthetic genes encoding silk or silk-like sequences. In their raw form, the native silk fibroins obtained from the *Bombyx mori* silkworms are coated with a glue-like protein called sericin, which is completely or essentially completely extracted from the fibers before the fibers that make up the fiber construct are seeded with cells.

The fiber construct can comprise a composite of: (1) silk and collagen fibers; (2) silk and collagen foams, meshes, or sponges; (3) silk fibroin fibers and silk foams, meshes, or sponges; (4) silk and biodegradable polymers [e.g., cellulose, cotton, gelatin, poly lactide, poly glycolic, poly(lactide-co-glycolide), poly caprolactone, polyamides, polyanhydrides, polyaminoacids, polyortho esters, poly acetals, proteins, degradable polyurethanes, polysaccharides, polycyanoacrylates, Glycosamino glycans (e.g., chondroitin sulfate, heparin, etc.), Polysaccharides (native, reprocessed or genetically engineered versions: e.g., hyaluronic acid, alginates, xanthans, pectin, chitosan, chitin, and the like), elastin (native, reprocessed or genetically engineered and chemical versions), and collagens (native, reprocessed or genetically engineered versions], or (5) silk and non-biodegradable polymers (e.g., polyamide, polyester, polystyrene, polypropylene, polyacrylate, polyvinyl, polycarbonate, polytetrafluorethylene, or nitrocellulose material. The composite generally enhances fiber construct properties such as porosity, degradability, and also enhances cell seeding, proliferation, differentiation or tissue development. FIGS. 16A, 16B and 16C illustrate the ability of collagen fibers to support BMSC growth and ligament specific differentiation.

The fiber construct can also be treated to enhance cell proliferation and/or tissue differentiation thereon. Exemplary fiber construct treatments for enhancing cell proliferation and tissue differentiation include, but are not limited to, metals, irradiation, crosslinking, chemical surface modifications [e.g., RGD (arg-gly-asp) peptide coating, fibronectin coating, coupling growth factors], and physical surface modifications.

A second aspect of this disclosure relates to a mechanically and biologically functional ACL formed from a novel silk-fiber-based fiber construct and autologous or allogenic (depending on the recipient of the tissue) bone marrow stromal cells (BMSCs) seeded on the fiber construct. The silk-fiber-based fiber construct induces stromal cell differentiation towards ligament lineage without the need for any mechanical stimulation during bioreactor cultivation. BMSCs seeded on the silk-fiber-based fiber construct and grown in a petri dish begin to attach and spread (see FIGS. 7A-D); the cells proliferate to cover the fiber construct (see FIGS. 8A-B, FIG. 9A and FIG. 9B) and differentiate, as shown by the expression of ligament specific markers (see FIG. 14). Markers for cartilage (collagen type II) and for bone (bone sialoprotein) were not expressed (see FIG. 14). Data illustrating the expression of ligament specific markers is set forth in an example, below.

Another aspect of this disclosure relates to a method for producing an ACL ex vivo. Cells capable of differentiating into ligament cells are grown under conditions that simulate the movements and forces experienced by an ACL in vivo through the course of embryonic development into mature ligament function. Specifically, under sterile conditions, pluripotent cells are seeded within a three-dimensional silk-fiber-based fiber construct to which cells can adhere and which is advantageously of cylindrical shape. The three-dimensional silk-fiber-based fiber construct used in the method serves as a preliminary fiber construct, which is supplemented and possibly even replaced by extracellular fiber construct components produced by the differentiating cells. Use of the novel silk-fiber-based fiber construct may enhance or accelerate the development of the ACL. For instance, the novel silk-fiber-based fiber construct can be designed to possess specific mechanical properties (e.g., increased tensile strength) so that it can withstand strong forces prior to reinforcement from extracellular (e.g., collagen and tenascin) fiber construct components. Other advantageous properties of the novel silk-fiber based preliminary fiber construct include, without limitation, biocompatibility and susceptibility to biodegradation.

The pluripotent cells may be seeded within the preliminary fiber construct either pre- or post-fiber construct formation, depending upon the particular fiber construct used and upon the method of fiber construct formation. Uniform seeding is usually preferable. In theory, the number of cells seeded does not limit the final ligament produced; however, optimal seeding may increase the rate of generation. Optimal seeding amounts will depend on the specific culture conditions. The fiber construct can be seeded with from about 0.05 to 5 times the physiological cell density of a native ligament.

One or more types of pluripotent cells are used in the method. Such cells have the ability to differentiate into a wide variety of cell types in response to the proper differentiation signals and to express ligament specific markers. More specifically, the method uses cells, such as bone marrow stromal cells, that have the ability to differentiate into cells of ligament and tendon tissue. If the resulting bioengineered ligament is to be transplanted into a patient, the cells should be derived from a source that is compatible with the intended recipient. Although the recipient will generally be a human, applications in veterinary medicine also exist. The cells can be obtained from the recipient (autologous), although compatible donor cells may also be used to make allogenic ligaments. For example, when making allogenic ligaments (e.g., using cells from another human such as bone marrow stromal cells isolated from donated bone marrow or ACL fibroblasts isolated from donated ACL tissue), human anterior cruciate ligament fibroblast cells isolated from intact donor ACL tissue (e.g., cadaveric or from total knee transplantations), ruptured ACL tissue (e.g., harvested at the time of surgery from a patient undergoing ACL reconstruction) or bone marrow stromal cells may be used. The determination of compatibility is within the means of the skilled practitioner.

Ligaments or tendons including, but not limited to, the posterior cruciate ligament, rotator cuff tendons, medial collateral ligament of the elbow and knee, flexor tendons of the hand, lateral ligaments of the ankle and tendons and ligaments of the jaw or temporomandibular joint other than ACL, cartilage, bone and other tissues may be engineered with the fiber construct in accordance with methods of this disclosure. In this manner, the cells to be seeded on the fiber construct are selected in accordance with the tissue to be produced (e.g., pluripotent or of the desired tissue type). Cells seeded on the fiber construct, as described herein, can be autologous or allogenic. The use of autologous cells effectively creates an allograft or autograft for implantation in a recipient.

As recited, to form an ACL, cells, such as bone marrow stromal cells, are seeded on the fiber construct. Bone marrow stromal cells are a type of pluripotent cell and are also referred to in the art as mesenchymal stem cells or simply as stromal cells. As recited, the source of these cells can be autologous or allogenic. Additionally, adult or embryonic stem or pluripotent cells can be used if the proper environment (either in vivo or in vitro), seeded on the silk-fiber based fiber construct, can recapitulate an ACL or any other desired ligament or tissue in extracellular fiber construct composition (e.g., protein, glycoprotein content), organization, structure or function.

Fibroblast cells can also be seeded on the inventive fiber construct. Since fibroblast cells are often not referred to as pluripotent cells, fibroblasts are intended to include mature human ACL fibroblasts (autologous or allogenic) isolated from ACL tissue, fibroblasts from other ligament tissue, fibroblasts from tendon tissue, from neonatal foreskin, from umbilical cord blood, or from any cell, whether mature or pluripotent, mature dedifferentiated, or genetically engineered, such that when cultured in the proper environment (either in vivo or in vitro), and seeded on the silk-fiber based fiber construct, can recapitulate an ACL or any other desired ligament or tissue in extracellular fiber construct composition (e.g., protein, glycoprotein content), organization, structure or function.

The faces of the fiber construct cylinder are each attached to anchors, through which a range of forces is to be applied to the fiber construct. To facilitate force delivery to the fiber construct, the entire surface of each respective face of the fiber construct can contact the face of the respective anchors. Anchors with a shape that reflects the site of attachment (e.g., cylindrical) are best suited for use in this method. Once assembled, the cells in the anchored fiber construct are cultured under conditions appropriate for cell growth and regeneration. The fiber construct is subjected to one or more mechanical forces applied through the attached anchors (e.g., via movement of one or both of the attached anchors) during the course of culture. The mechanical forces are applied over the period of culture to mimic conditions experienced by the native ACL or other tissues in vivo.

The anchors must be made of a material suitable for fiber construct attachment, and the resulting attachment should be strong enough to endure the stress of the mechanical forces applied. In addition, the anchors can be of a material that is suitable for the attachment of extracellular fiber construct that is produced by the differentiating cells. The anchors support bony tissue in-growth (either in vitro or in vivo) while anchoring the developing ligament. Some examples of suitable anchor material include, without limitation, hydroxyapatite, *Goniopora* coral, demineralized bone, bone (allogenic or autologous). Anchor materials may also include titanium, stainless steel, high density polyethylene, DACRON and TEFLON.

Alternatively, anchor material may be created or further enhanced by infusing a selected material with a factor that promotes either ligament fiber construct binding or bone fiber construct binding or both. The term infuse is considered to include any method of application that appropriately distributes the factor onto the anchor (e.g., coating, permeating, contacting). Examples of such factors include without limitation, laminin, fibronectin, any extracellular fiber construct protein that promotes adhesion, silk, factors that contain arginine-glycine-aspartate (RGD) peptide binding regions or the RGD peptides themselves. Growth factors or bone morphogenic protein can also be used to enhance anchor attachment. In addition, anchors may be pre-seeded with cells (e.g., stem cells, ligament cells, osteoblasts, osteogenic progenitor cells) that adhere to the anchors and bind the fiber construct, to produce enhanced fiber construct attachment both in vitro and in vivo.

An exemplary anchor system is disclosed in applicant's co-pending application U.S. Ser. No. 09/950,561, which is incorporated herein by reference in its entirety. The fiber construct is attached to the anchors via contact with the anchor face or alternatively by actual penetration of the fiber construct material through the anchor material. Because the force applied to the fiber construct via the anchors dictates the final ligament produced, the size of the final ligament produced is, in part, dictated by the size of the attachment site of the anchor. An anchor of appropriate size to the desired final ligament should be used. An example of an anchor shape for the formation of an ACL is a cylinder. However, other anchor shapes and sizes will also function adequately. For example, anchors can have a size and composition appropriate for direct insertion into bone tunnels in the femur and tibia of a recipient of the bioengineered ligament.

Alternatively, anchors can be used only temporarily during in vitro culture, and then removed when the fiber construct alone is implanted in vivo.

Further still, the novel silk-fiber-based fiber construct can be seeded with BMSCs and cultured in a bioreactor. Two types of growth environments currently exist that may be used in accordance with methods of this disclosure: (1) the in vitro bioreactor apparatus system, and (2) the in vivo knee joint, which serves as a "bioreactor" as it provides the physiologic environment including progenitor cells and stimuli (both chemical and physical) necessary for the development of a viable ACL given a fiber construct with proper biocompatible and mechanical properties. The bioreactor apparatus provides optimal culture conditions for the formation of a ligament in terms of differentiation and extracellular fiber construct (ECM) production, and which thus provides the ligament with optimal mechanical and biological properties prior to implantation in a recipient. Additionally, when the silk-fiber based fiber construct is seeded and cultured with cells in vitro, a petri dish may be considered to be the bioreactor within which conditions appropriate for cell growth and regeneration exist, i.e., a static environment.

Cells can also be cultured on the fiber construct fiber construct without the application of any mechanical forces, i.e., in a static environment. For example, the silk-fiber based fiber construct alone, with no in vitro applied mechanical forces or stimulation, when seeded and cultured with BMSCs, induces the cells to proliferate and express ligament and tendon specific markers (see the examples, described herein). The knee joint may serve as a physiological growth and development environment that can provide the cells and the correct environmental signals (chemical and physical) to the fiber construct fiber construct such that an ACL technically develops. Therefore, the knee joint (as its own form of bioreactor) plus the fiber construct (either non-seeded, seeded and not differentiated in vitro, or seeded and differentiated in vitro prior to implantation) will result in the development of an ACL, or other desired tissue depending upon the cell type seeded on the fiber construct and the anatomical location of fiber construct implantation. FIG. 15 A-B illustrates the effects of the medial collateral knee joint environment on medial collateral ligament (MCL) development when only a non-seeded silk-based fiber construct with appropriate MCL mechanical properties is implanted for 6 weeks in vivo. Whether the cells are cultured in a static environment with no mechanical stimulation applied, or in a dynamic environment, such as in a bioreactor apparatus, conditions appropriate for cell growth and regeneration are advantageously present for the engineering of the desired ligament or tissue.

In experiments described in the examples, below, the applied mechanical stimulation was shown to influence the morphology, and cellular organization of the progenitor cells within the resulting tissue. The extracellular fiber construct components secreted by the cells and the organization of the extracellular fiber construct throughout the tissue was also significantly influenced by the forces applied to the fiber construct during tissue generation. During in vitro tissue generation, the cells and extracellular fiber construct aligned along the axis of load, reflecting the in vivo organization of a native ACL that is also along the various load axes produced from natural knee joint movement and function. These results suggest that the physical stimuli experienced in nature by cells of developing tissue, such as the ACL, play a significant role in progenitor cell differentiation and tissue formation. They further indicate that this role can be effectively duplicated in vitro by mechanical manipulation to produce a similar tissue. The more closely the forces produced by mechanical manipulation resemble the forces experienced by an ACL in vivo, the more closely the resultant tissue will resemble a native ACL.

When mechanical stimulation is applied in vitro to the fiber construct via a bioreactor, there exists independent but concurrent control over both cyclic and rotation strains as applied to one anchor with respect to the other anchor. Alternatively, the fiber construct alone may be implanted in vivo, seeded with ACL cells from the patient and exposed in vivo to mechanical signaling via the patient.

When the fiber construct is seeded with cells prior to implantation, the cells are cultured within the fiber construct under conditions appropriate for cell growth and differentiation. During the culture process, the fiber construct may be subjected to one or more mechanical forces via movement of one or both of the attached anchors. The mechanical forces of tension, compression, torsion and shear, and combinations thereof, are applied in the appropriate combinations, magnitudes, and frequencies to mimic the mechanical stimuli experienced by an ACL in vivo.

Various factors will influence the amount of force that can be tolerated by the fiber construct (e.g., fiber construct composition, cell density). Fiber construct strength is expected to change through the course of tissue development. Therefore, applied mechanical forces or strains will increase, decrease or remain constant in magnitude, duration, frequency and variety over the period of ligament generation, to appropriately correspond to fiber construct strength at the time of application.

When producing an ACL, the more accurate the intensity and combination of stimuli applied to the fiber construct during tissue development, the more the resulting ligament will resemble a native ACL. Two issues must be considered regarding the natural function of the ACL when devising the in vitro mechanical force regimen that closely mimics the in vivo environment: (1) the different types of motion experienced by the ACL and the responses of the ACL to knee joint movements and (2) the extent of the mechanical stresses experienced by the ligament. Specific combinations of mechanical stimuli are generated from the natural motions of the knee structure and transmitted to the native ACL.

To briefly describe the motions of the knee, the connection of the tibia and femur by the ACL provides six degrees of freedom when considering the motions of the two bones relative to each other. The tibia can move in three directions and can rotate relative to the axes for each of these three directions. The knee is restricted from achieving the full ranges of these six degrees of freedom due to the presence of ligaments and capsular fibers and the knee surfaces themselves (Biden et al., "Experimental Methods Used to Evaluate Knee Ligament Function," Knee Ligaments Structure, Function, Injury and Repair, Ed. D. Daniel et al., Raven Press, pp. 135-151, 1990). Small translational movements are also possible. The attachment sites of the ACL are responsible for its stabilizing roles in the knee joint. The ACL functions as a primary stabilizer of anterior-tibial translation, and as a secondary stabilizer of valgus-varus angulation, and tibial rotation (Shoemaker et al., "The Limits of Knee Motion," Knee Ligaments: Structure, Function, Injury and Repair, Ed. D. Daniel et al., Raven Press, pp. 1534-161, 1990). Therefore, the ACL is responsible for stabilizing the knee in three of the six possible degrees of freedom. As a result, the ACL has developed a specific fiber organization and overall structure to perform these stabilizing functions. These conditions are simulated in vitro to produce a tissue with similar structure and fiber organization.

The extent of mechanical stresses experienced by the ACL can be similarly summarized. The ACL undergoes cyclic loads of about 400 N between one and two million cycles per year (Chen et al., J. Biomed. Mat. Res. 14: 567-586, 1980). Also considered are linear stiffness (~182 N/mm), ultimate deformation (100% of ACL) and energy absorbed at failure (12.8 N-m) (Woo et al., The tensile properties of human anterior cruciate ligament (ACL) and ACL graft tissues, Knee Ligaments: Structure, Function, Injury and Repair, Ed. D. Daniel et al. Raven Press, pp. 279-289, 1990) when developing an ACL surgical replacement.

The examples section, below, details the production of a prototype bioengineered anterior cruciate ligament (ACL) ex vivo. Mechanical forces mimicking a subset of the mechanical stimuli experienced by a native ACL in vivo (rotational deformation and linear deformation) were applied in combination, and the resulting ligament that was formed was studied to determine the effects of the applied forces on tissue development. Exposure of the developing ligament to physiological loading during in vitro formation induced the cells to adopt a defined orientation along the axes of load, and to generate extracellular matrices along the axes as well. These results indicate that the incorporation of complex multi-dimensional mechanical forces into the regime to produce a more complex network of load axes that mimics the environment of the native ACL will produce a bioengineered ligament that more closely resembles a native ACL.

The different mechanical forces that may be applied include, without limitation, tension, compression, torsion, and shear. These forces are applied in combinations that simulate forces experienced by an ACL in the course of natural knee joint movements and function. These movements include, without limitation, knee joint extension and flexion as defined in the coronal and sagittal planes, and knee joint flexion. Optimally, the combination of forces applied mimics the mechanical stimuli experienced by an anterior cruciate ligament in vivo as accurately as is experimentally possible. Varying the specific regimen of force application through the course of ligament generation is expected to influence the rate and outcome of tissue development, with optimal conditions to be determined empirically. Potential variables in the regimen include, without limitation: (1) strain rate, (2) percent strain, (3) type of strain (e.g., translation and rotation), (4) frequency, (5) number of cycles within a given regime, (6) number of different regimes, (7) duration at extreme points of ligament deformation, (8) force levels, and (9) different force combinations. A wide variety of variations exist. The regimen of mechanical forces applied can produce helically organized fibers similar to those of the native ligament, described below.

The fiber bundles of a native ligament are arranged into a helical organization. The mode of attachment and the need for the knee joint to rotate ~140° of flexion has resulted in the native ACL inheriting a 90° twist and with the peripheral fiber bundles developing a helical organization. This unique biomechanical feature allows the ACL to sustain extremely high loading. In the functional ACL, this helical organization of fibers allows anterior-posterior and posterior-anterior fibers to remain relatively isometric in respect to one another for all degrees of flexion, thus load can be equally distributed to all fiber bundles at any degree of knee joint flexion, stabilizing the knee throughout all ranges of joint motion. Mechanical forces that simulate a combination of knee joint flexion and knee joint extension can be applied to the developing ligament to produce an engineered ACL that possesses this same helical organization. The mechanical apparatus used in the experiments presented in the examples, below, provides control over strain and strain rates (both translational and rotational). The mechanical apparatus will monitor the actual load experienced by the growing ligaments, serving to 'teach' the ligaments over time through monitoring and increasing the loading regimes.

Another aspect of this disclosure relates to the bioengineered anterior cruciate ligament produced by the above-described methods. The bioengineered ligament produced by these methods is characterized by cellular orientation and/or a fiber construct crimp pattern in the direction of the mechanical forces applied during generation. The ligament is also characterized by the production/presence of extracellular fiber construct components (e.g., collagen type I and type III, fibronectin, and tenascin-C proteins) along the axis of mechanical load experienced during culture. The ligament fiber bundles can be arranged into a helical organization, as discussed above.

The above methods using the novel silk-fiber-based fiber construct are not limited to the production of an ACL, but can also be used to produce other ligaments and tendons found in the knee (e.g., posterior cruciate ligament) or other parts of the body (e.g., hand, wrist, ankle, elbow, jaw and shoulder), such as for example, but not limited to posterior cruciate ligament, rotator cuff tendons, medial collateral ligament of the elbow and knee, flexor tendons of the hand, lateral ligaments of the ankle and tendons and ligaments of the jaw or temporomandibular joint. All moveable joints in a human body have specialized ligaments that connect the articular extremities of the bones in the joint. Each ligament in the body has a specific structure and organization that is dictated by its function and environment. The various ligaments of the body, their locations and functions are listed in Anatomy, Descriptive and Surgical (Gray, H., Eds. Pick, T. P., Howden, R., Bounty Books, New York, 1977), the pertinent contents of which are incorporated herein by reference. By determining the physical stimuli experienced by a given ligament or tendon, and incorporating forces which mimic these stimuli, the above-described method for producing an ACL ex vivo can be adapted to produce bioengineered ligaments and tendons ex vivo that simulates any ligament or tendon in the body.

The specific type of ligament or tendon to be produced is predetermined prior to tissue generation since several aspects of the method vary with the specific conditions experienced in vivo by the native ligament or tendon. The mechanical forces to which the developing ligament or tendon is subjected during cell culture are determined for the particular ligament or tendon type being cultivated. The specific conditions can be determined by studying the native ligament or tendon and its environment and function. One or more mechanical forces experienced by the ligament or tendon in vivo are applied to the fiber construct during culture of the cells in the fiber construct. The skilled practitioner will recognize that a ligament or tendon that is superior to those currently available can be produced by the application of a subset of forces experienced by the native ligament or tendon. However, optimally, the full range of in vivo forces will be applied to the fiber construct in the appropriate magnitudes and combinations to produce a final product that most closely resembles the native ligament or tendon. These forces include, without limitation, the forces described above for the production of an ACL. Because the mechanical forces applied vary with ligament or tendon type, and the final size of the ligament or tendon will be influenced by the anchors used, optimal anchor composition, size and fiber construct attachment sites are to be determined for each type of ligament or tendon by the skilled practitioner. The type of cells seeded on the fiber construct is obviously determined based on the type of ligament or tendon to be produced.

Other tissue types can be produced ex vivo using methods similar to those described above for the generation of ligaments or tendons ex vivo. The above-described methods can also be applied to produce a range of engineered tissue products that involve mechanical deformation as a major part of their function, such as muscle (e.g., smooth muscle, skeletal muscle, cardiac muscle), bone, cartilage, vertebral discs, and some types of blood vessels. Bone marrow stromal cells possess the ability to differentiate into these as well as other tissues. The geometry of the silk-based fiber construct or composite fiber construct can easily be adapted to the correct anatomical geometrical configuration of the desired tissue type. For example, silk fibroin fibers can be reformed in a cylindrical tube to recreate arteries.

The results presented in the examples, below, indicate that growth in an environment that mimics the specific mechanical environment of a given tissue type will induce the appropriate cell differentiation to produce a bioengineered tissue that significantly resembles native tissue. The ranges and types of mechanical deformation of the fiber construct can be extended to produce a wide range of tissue structural organization. The cell culture environment can reflect the in vivo environment experienced by the native tissue and the cells it contains, throughout the course of embryonic development to mature function of the cells within the native tissue, as accurately as possible. Factors to consider when designing specific culture conditions to produce a given tissue include, without limitation, the fiber construct composition, the method of cell immobilization, the anchoring method of the fiber construct or tissue, the specific forces applied, and the cell culture medium. The specific regimen of mechanical stimulation depends upon the tissue type to be produced, and is established by varying the application of mechanical forces (e.g., tension only, torsion only, combination of tension and torsion, with and without shear, etc.), the force amplitude (e.g., angle or elongation), the frequency and duration of the application, and the duration of the periods of stimulation and rest.

The method for producing the specific tissue type ex vivo is an adaptation of the above-described method for producing an ACL. Components involved include pluripotent cells, a three-dimensional fiber construct to which cells can adhere, and a plurality of anchors that have a face suitable for fiber construct attachment. The pluripotent cells (such as bone marrow stromal cells) are seeded in the three dimensional fiber construct by means to uniformly immobilize the cells within the fiber construct. The number of cells seeded is also not viewed as limiting, however, seeding the fiber construct with a high density of cells may accelerate tissue generation.

The specific forces applied are to be determined for each tissue type produced through examination of native tissue and the mechanical stimuli experienced in vivo. A given tissue type experiences characteristic forces that are dictated by location and function of the tissue within the body. For instance, cartilage is known to experience a combination of shear and compression/tension in vivo; bone experiences compression.

Additional stimuli (e.g., chemical stimuli, electro-magnetic stimuli) can also be incorporated into the above-described methods for producing bioengineered ligaments, tendons and other tissues. Cell differentiation is known to be influenced by chemical stimuli from the environment, often produced by surrounding cells, such as secreted growth or differentiation factors, cell-cell contact, chemical gradients, and specific pH levels, to name a few. Other more unique stimuli are experienced by more specialized types of tissues (e.g., the electrical stimulation of cardiac muscle). The application of such tissue specific stimuli (e.g., 1-10 ng/ml transforming growth factor beta-1 (TGF-β1) independently or in concert with the appropriate mechanical forces is expected to facilitate differentiation of the cells into a tissue that more closely approximates the specific natural tissue.

Tissues produced by the above-described methods provide an unlimited pool of tissue equivalents for surgical implantation into a compatible recipient, particularly for replacement or repair of damaged tissue. Engineered tissues may also be utilized for in vitro studies of normal or pathological tissue function, e.g., for in vitro testing of cell- and tissue-level responses to molecular, mechanical, or genetic manipulations. For example, tissues based on normal or transfected cells can be used to assess tissue responses to biochemical or mechanical stimuli, identify the functions of specific genes or gene products that can be either over-expressed or knocked-out, or to study the effects of pharmacological agents. Such studies will likely provide more insight into ligament, tendon and tissue development, normal and pathological function, and eventually lead toward fully functional tissue engineered replacements, based in part on already established tissue engineering approaches, new insights into cell differentiation and tissue development, and the use of mechanical regulatory signals in conjunction with cell-derived and exogenous biochemical factors to improve structural and functional tissue properties.

The production of engineered tissues, such as ligaments and tendons, also has the potential for applications such as harvesting bone marrow stromal cells from individuals at high risk for tissue injury (e.g., ACL rupture) prior to injury. These cells could be either stored until needed or seeded into the appropriate fiber construct and cultured and differentiated in vitro under mechanical stimuli to produce a variety of bioengineered prosthetic tissues to be held in reserve until needed by the donor. The use of bioengineered living tissue prosthetics that better match the biological environment in vivo and that provide the required physiological loading to sustain, for example, the dynamic equilibrium of a normal, fully functional ligament should reduce rehabilitation time for a recipient of a prosthesis from months to weeks, particularly if the tissue is pre-grown and stored. Benefits include a more rapid regain of functional activity, shorter hospital stays, and fewer problems with tissue rejections and failures.

Additional aspects of this invention are further exemplified in the following examples. It will be apparent to those skilled in the art that many modifications, both to the materials and methods, may be practiced without departing from the invention.

In a first example, raw *Bombyx mori* silkworm fibers, shown in FIG. 1A, were extracted to remove sericin, the glue-like protein coating the native silk fibroin (see FIGS. 1A-C). The appropriate number of fibers per group were arranged in parallel and extracted in an aqueous solution of 0.02 M $Na_2CO_3$ and 0.3% (w/v) IVORY soap solution for 60 minutes at 90° C., then rinsed thoroughly with water to extract the glue-like sericin proteins.

Costello's equation for a three-strand, helical rope geometry was derived to predict mechanical properties of the silk-fiber-based construct. The derived model is a series of equations that when combined, take into account extracted silk fiber material properties and desired fiber construct geometrical hierarchy to compute the overall strength and stiffness of the fiber construct as a function of pitch angle for a given level of geometrical hierarchy.

The material properties of a single silk fiber include fiber diameter, modulus of elasticity, Poisson's ratio, and the ultimate tensile strength (UTS). Geometrical hierarchy may be defined as the number of twisting levels in a given fiber construct level. Each level (e.g., group, bundle, strand, cord, ligament) is further defined by the number of groups of fibers twisted about each other and the number of fibers in each group of the first level twisted where the first level is define as a group, the second level as a bundle, the third as a strand and the fourth as a cord, the fifth as the ligament.

The model assumes that each group of multiple fibers act as a single fiber with an effective radius determined by the number of individual fibers and their inherent radius, i.e., the model discounts friction between the individual fibers due to its limited role in given a relatively high pitch angle.

Two applicable geometries (Matrix 1 and Matrix 2) of the many fiber construct geometrical configurations (see Table 10, supra) computed to yield mechanical properties mimicking those of a native ACL were derived for more detailed analysis. A six-cord construct was selected for use as the ACL replacement. Matrix configurations are as follows: Matrix 1:1 ACL prosthesis=6 parallel cords; 1 cord=3 twisted strands (3 twists/cm); 1 strand=6 twisted bundles (3 twists/cm); 1 bundle=30 parallel washed fibers; and Matrix 2: 1 ACL matrix=6 parallel cords; 1 cord=3 twisted strands (2 twists/cm); 1 strand=3 twisted bundles (2.5 twists/cm); 1 bundle=3 groups (3 twists/cm); 1 group=15 parallel extracted silk fibroin fibers. The number of fibers and geometries were selected such that the silk prostheses are similar to the ACL biomechanical properties in UTS, linear stiffness, yield point and % elongation at break (see Table 10, supra), thus serving as a solid starting point for the development of a tissue engineered ACL.

Mechanical properties of the silk fibroin were characterized using a servohydraulic Instron 8511 tension/compression system with Fast-Track software (Instron Corp., Canton, Mass., USA) (see FIG. 1D). Single pull-to-failure and fatigue analyses were performed on single silk fibers, extracted fibroin and organized cords. Fibers and fibroin were organized in both the parallel helical geometries of Matrix 1 (see FIG. 2C) and of Matrix 2 (see FIG. 2D) for characterization. Single pull to failure testing was performed at a strain rate of 100%/sec; force elongation histograms were generated and data analyzed using Instron Series IX software. Both Matrix 1 and Matrix 2 yielded similar mechanical and fatigue properties to the ACL in UTS, linear stiffness, yield point and percent elongation at break (see Table 10 and FIGS. 3A-D).

Fatigue analyses were performed using a servohydraulic Instron 8511 tension/compression system with Wavemaker software on single cords of both Matrix 1 and Matrix 2. Data was extrapolated to represent the 6-cord ACL prostheses, which is shown in FIGS. 3B and 3D. Cord ends were embedded in an epoxy mold to generate a 3-cm-long construct between anchors. Cycles to failure at UTS's of 1,680 N and 1,200 N (n=5 for each load) for Matrix 1 (see FIG. 3B) and at UTS's of 2280 N, 2100 N and 1800 N loads (n=3 for each load) for Matrix 2 (see FIG. 3D) were determined using a H-sine wave function at 1 Hz generated by Wavemaker 32 version 6.6 software (Instron Corp.). Fatigue testing was conducted in a neutral phosphate buffered saline (PBS) solution at room temperature.

Complete sericin removal was observed after 60 min at 90° C. as determined by SEM (see FIGS. 1A-C). Removal of sericin from silk fibers altered the ultrastructure of the fibers, resulting in a smoother fiber surface, and the underlying silk fibroin was revealed (shown in FIGS. 1A-C), with average diameter ranging between 20-40 μm. The fibroin exhibited a significant 15.2% decrease in ultimate tensile strength (1.033+/−0.042 N/fiber to 0.876+/−0.1 N/fiber) ($p<0.05$, paired Students t-test) (see FIG. 1D). The mechanical properties of the optimized silk matrices (see FIG. 2A-D & FIG. 3A-D) are summarized in Table 11 above and in FIG. 3A (for Matrix 1) and in FIG. 3C (for Matrix 2). It is evident from these results that the optimized silk matrices exhibited values comparable to those of native ACL, which have been reported to have an average ultimate tensile strength (UTS) of ~2100 N, stiffness of ~250 N/nm, yield point ~2100 N and 33% elongation at break (See Woo, SL-Y, et al., The Tensile Properties of Human Anterior Cruciate Ligament (ACL) and ACL Graft Tissue in Knee Ligaments: Structure, Function, Injury and Repair, 279-289, Ed. D. Daniel et al., Raven Press 1990).

Regression analysis of fiber construct fatigue data, shown in FIG. 3B for Matrix 1 and in FIG. 3D for Matrix 2, when extrapolated to physiological load levels (400 N) predict the number of cycles to failure in vivo, indicate a fiber construct life of 3.3 million cycles for Matrix 1 and a life of greater than 10 million cycles for Matrix 2. The helical fiber construct design utilizing washed silk fibers resulted in a fiber construct with physiologically equivalent structural properties, confirming its suitability as a scaffold for ligament tissue engineering.

In another example involving cell isolation and culture, bone marrow stromal cells (BMSC), pluripotent cells capable of differentiating into osteogenic, chondrogenic, tendonogenic, adipogenic and myogenic lineages, were chosen since the formation of the appropriate conditions can direct their differentiation into the desired ligament fibroblast cell line (Markolf et al., J. Bone Joint Surg. 71A: 887-893, 1989; Caplan et al., Mesenchymal stem cells and tissue repair, The Anterior Cruciate Ligament: Current and Future Concepts, Ed. D. W. Jackson et al., Raven Press, Ltd, New York, 1993; Young et al., J. Orthopaedic Res. 16: 406-413, 1998).

Human BMSCs were isolated from bone marrow from the iliac crest of consenting donors at least 25 years of age by a commercial vendor (Cambrex, Walkersville, Md.). Twenty-two milliliters of human marrow was aseptically aspirated into a 25 ml syringe containing three milliliters of heparinized (1000 units per milliliter) saline solution. The heparinized marrow solution was shipped overnight on ice to the laboratory for bone marrow stromal cells isolation and culture. Upon arrival from the vendor, the twenty-five milliliter aspirates were resuspended in Dulbecco's Modified Eagle Medium (DMEM) supplemented with 10% fetal bovine serum (FBS), 0.1 mM nonessential amino acids, 100 U/ml penicillin, 100 mg/L streptomycin (P/S), and 1 ng/ml basic fibroblast growth factor (bFGF) (Life Technologies, Rockville, Md.) and plated at 8-10 microliters of aspirate/cm2 in tissue culture flasks. Fresh medium was added to the marrow aspirates twice a week for up to nine days of culture. BMSCs were selected based on their ability to adhere to the tissue culture plastic; non-adherent hematopoietic cells were removed during medium replacement after 9-12 days in culture. Medium was changed twice per week thereafter. When primary BMSC became near confluent (12-14 days), they were detached using 0.25% trypsin/1 mM EDTA and replated at $5\times10^3$ cells/cm$^2$. First passage (P1) hBMSCs were trypsinized and frozen in 8% DMSO/10% FBS/DMEM for future use.

Frozen P1 hBMSCs were defrosted, replated at $5\times10^3$ cells/cm$^2$ (P2), trypsinized when near confluency, and used for fiber construct seeding. Sterilized (ethylene oxide) silk matrices (specifically, single cords of Matrices 1 and 2, bundles of 30 parallel extracted silk fibers, and helical ropes of collage fibers) were seeded with cells in customized seeding chambers (1 ml total volume) machined in Teflon blocks to minimize cell-medium volume and increase cell-fiber construct contact. Seeded matrices, following a 4 hour incubation period with the cell slurry ($3.3\times10^6$ BMSCs/ml) were transferred into a petri dish containing an appropriate amount of cell culture medium for the duration of the experiments.

To determine the degradation rate of the silk fibroin, ultimate tensile strength (UTS) was measured as a function of cultivation period in physiological growth conditions, i.e., in cell culture medium. Groups of 30 parallel silk fibers 3 cm in length were extracted, seeded with hBMSCs, and cultured on the fibroin over 21 days at 37° C. and 5% $CO_2$. Non-seeded control groups were cultured in parallel. Silk fibroin UTS was determined as a function of culture duration for seeded and non-seeded groups.

The response of bone marrow stromal cells to the silk fiber construct was also examined.

Figure 7A:
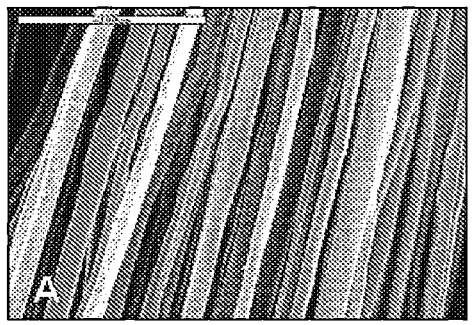
FIG. 7A illustrates SEM of extracted silk fibroin prior to seeding with cells.
Figure 7B:
FIG. 7B illustrates SEM of bone marrow stromal cells seeded and attached on silk fibroin immediately post seeding.
Figure 7C:
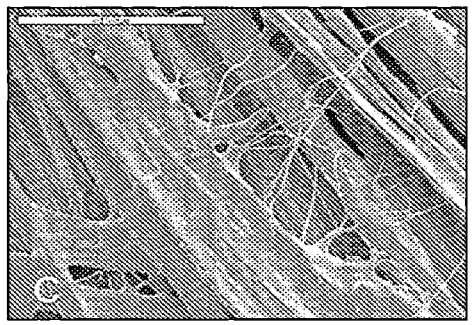
FIG. 7C illustrates SEM of bone marrow cells attached and spread on silk fibroin 1 day post seeding.
Figure 7D:
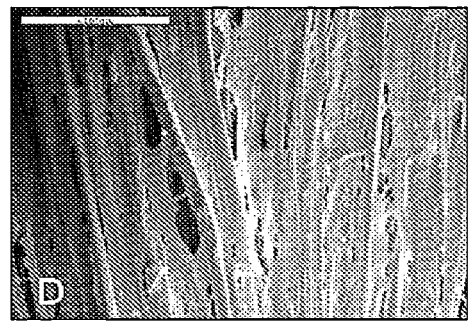
FIG. 7D illustrates SEM of bone marrow stromal cells seeded on silk fibroin 14 days post seeding forming an intact cell-extracellular matrix sheet.
Figure 8A:
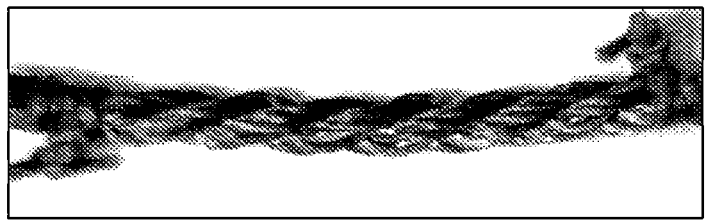
FIG. 8A illustrates a 3 cm length of the silk fibroin cord illustrated in FIG. 2C and seeded with bone marrow stromal cells, cultured for 14 days in a static environment and stained with MTT to show even cell coverage of the matrix following the growth period.
Figure 8B:
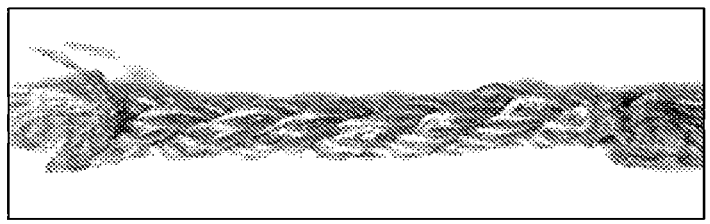
FIG. 8B illustrates a control strand of silk fibroin cord 3 cm in length stained with MTT.

BMSCs readily attached and grew on the silk and collagen matrices after 1 day in culture (See FIG. 7A-C and FIG. 16A), and formed cellular extensions to bridge neighboring fibers. As shown in FIG. 7D and FIG. 16B, a uniform cells sheet covering the construct was observed at 14 and 21 days of culture, respectively. MTT analysis confirmed complete fiber construct coverage by seeded BMSCs after 14 days in culture (see FIG. 8A-B). Total DNA quantification of cells grown on Matrix 1 (see FIG. 9A) and Matrix 2 (see FIG. 9B) confirmed that BMSCs proliferated and grew on the silk construct with the highest amount of DNA measured after 21 and 14 days, respectively, in culture.

Both BMSC-seeded or non-seeded extracted control silk fibroin groups of 30 fibers, maintained their mechanical integrity as a function of culture period over 21 days (see FIG. 10).

Figure 17:
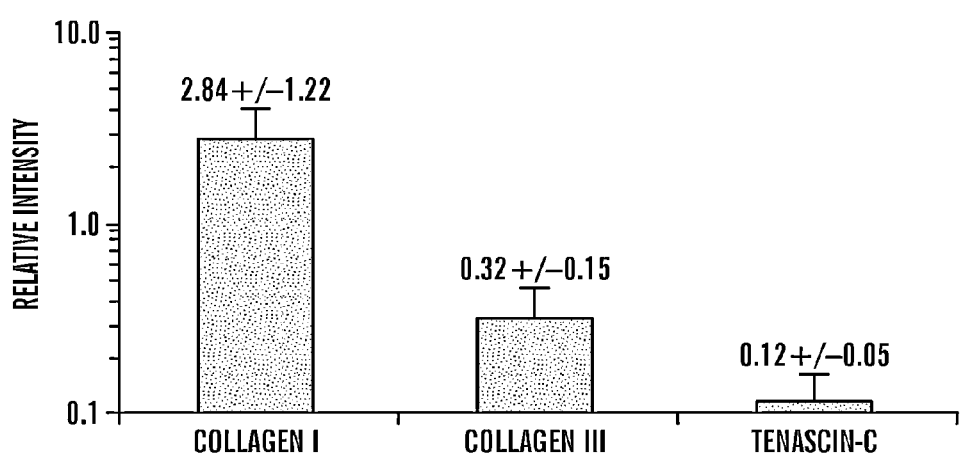
FIG. 17 illustrates real-time quantitative RT-PCR at 14 days that yielded a transcript ratio of collagen I to collagen III, normalized to GAPDH, of 8.9:1.

RT-PCR analysis of BMSCs seeded on cords of Matrix 2 indicated that both collagen I & III were upregulated over 14 days in culture (FIG. 14). Collagen type II and bone sialoprotein (as indicators of cartilage and bone specific differentiation, respectively) were either not detectable or negligibly expressed over the cultivation period. Real-time quantitative RT-PCR at 14 days yielded a transcript ratio of collagen I to collagen III, normalized to GAPDH, of 8.9:1 (see FIG. 17). The high ratio of collagen I to collagen III indicates that the response is not wound healing or scar tissue formation (as is observed with high levels of collagen type III), but rather ligament specific; the relative ratio of collagen I to collagen III in a native ACL is ~6.6:1 (Amiel et al., Knee Ligaments: Structure, Function, Injury, and Repair, 1990).

Additionally, studies are conducted to provide insight into the influence of directed multi-dimensional mechanical stimulation on ligament formation from bone marrow stromal cells in the bioreactor system. The bioreactor is capable of applying independent but concurrent cyclic multi-dimensional strains (e.g., translation, rotation) to the developing ligaments. After a 7 to 14 day static rest period (time post seeding), the rotational and translation strain rates and linear and rotational deformation are kept constant for 1 to 4 weeks. Translational strain (3.3%-10%, 1-3 mm) and rotational strain (25%, 90°) are concurrently applied at a frequency of 0.0167 Hz (one full cycle of stress and relaxation per minute) to the silk-based matrices seeded with BMSCs; an otherwise identical set of bioreactors with seeded matrices without mechanical loading serve as controls. The ligaments are exposed to the constant cyclic strains for the duration of the experiment days.

Following the culture period, ligament samples, both the mechanically challenged as well as the controls (static) are characterized for: (1) general histomorphological appearance (by visual inspection); (2) cell distribution (image processing of histological and MTT stained sections); (3) cell morphology and orientation (histological analysis); and (4) the production of tissue specific markers (RT-PCR, immunostaining).

Mechanical stimulation markedly affects the morphology and organization of the BMSCs and newly developed extracellular fiber construct, the distribution of cells along the fiber construct, and the upregulation of a ligament-specific differentiation cascade; BMSCs align along the long axis of the fiber, take on a spheroid morphology similar to ligament/tendon fibroblasts and upregulate ligament/tendon specific markers. Newly formed extracellular fiber construct (i.e., the composition of proteins produced by the cells) is expected to align along the lines of load as well as the long axis of the fiber construct. Directed mechanical stimulation is expected to enhance ligament development and formation in vitro in a bioreactor resulting from BMSCs seeded on the novel silk-based fiber construct. The longitudinal orientation of cells and newly formed fiber construct is similar to ligament fibroblasts found within an ACL in vivo (Woods et al., Amer. J. Sports Med. 19: 48-55, 1991). Furthermore, mechanical stimulation maintains the correct expression ratio between collagen type I transcripts and collagen type III transcripts (e.g., greater than 7:1) indicating the presence of newly formed ligament tissue versus scar tissue formation. The above results will indicate that the mechanical apparatus and bioreactor system provide a suitable environment (e.g., multi-dimensional strains) for in vitro formation of tissue engineered ligaments starting from bone marrow stromal cells and the novel silk-based fiber construct.

The culture conditions used in these preliminary experiments can be further expanded to more accurately reflect the physiological environment of a ligament (e.g., increasing the different types of mechanical forces) for the in vitro creation of functional equivalents of native ACL for potential clinical use. These methods are not limited to the generation of a bioengineered ACL. By applying the appropriate magnitude and variety of forces experienced in vivo, any type of ligament in the body as well as other types of tissue can be produced ex vivo by the methods of this disclosure.

Other embodiments are within the following claims.

TABLE 1

Ultimate tensile strength and stiffness (N/mm given a 3 cm long sample) as a function of sericin extraction from a 10-fiber silkworm silk yarn with 0 twists per inch (i.e., parallel) and (i) temperature and (ii) time. Repeat samples were processed two years after initial samples with no significant change in properties. N = 5 for all samples.

| Yarn | # of fibers | Temp | Time | UTS (N) | stdev | Stiff (N/mm) | stdev | UTS/ fiber (N) | Stiffness/ fiber (N/mm) |
|---|---|---|---|---|---|---|---|---|---|
| 10(0) | 10 | RT | 60 min | 10.74 | 0.83 | 6.77 | 0.65 | 1.07 | 0.68 |
| 10(0) | 10 | RT | 60 min (repeat) | 10.83 | 0.28 | 6.36 | 0.14 | 1.08 | 0.64 |
| 10(0) | 10 | 33 C. | 60 min | 10.44 | 0.17 | 6.68 | 0.55 | 1.04 | 0.67 |
| 10(0) | 10 | 37 C. | 60 min | 9.60 | 0.84 | 6.09 | 0.59 | 0.96 | 0.61 |
| 10(0) | 10 | 37 C. | 60 min (repeat) | 9.54 | 0.74 | 5.81 | 0.67 | 0.95 | 0.58 |
| 10(0) | 10 | 90 C. | 15 min | 9.22 | 0.55 | 4.87 | 0.62 | 0.92 | 0.49 |
| 10(0) | 10 | 90 C. | 30 min | 8.29 | 0.19 | 4.91 | 0.33 | 0.83 | 0.49 |
| 10(0) | 10 | 90 C. | 60 min | 8.60 | 0.61 | 4.04 | 0.87 | 0.86 | 0.40 |
| 10(0) | 10 | 90 C. | 60 min (repeat) | 8.65 | 0.67 | 4.55 | 0.69 | 0.87 | 0.46 |
| 10(0) | 10 | 94 C. | 60 min | 7.92 | 0.51 | 2.42 | 0.33 | 0.79 | 0.24 |
| 9(12s) × 3(9z) | 27 | non-extracted | | 24.50 | 0.38 | 8.00 | 0.49 | 0.91 | 0.30 |
| 9(12s) × 3(9z) | 27 | 90 C. | 60 min | 21.88 | 0.18 | 7.38 | 0.34 | 0.81 | 0.27 |
| 9(6s) × 3(3z) | 27 | non-extracted | | 24.94 | 0.57 | 9.51 | 0.57 | 0.92 | 0.35 |
| 9(6s) × 3(3z) | 27 | 90 C. | 60 min | 21.36 | 0.40 | 7.95 | 1.00 | 0.79 | 0.29 |

TABLE 1-continued

Ultimate tensile strength and stiffness (N/mm given a 3 cm long sample) as a function of sericin extraction from a 10-fiber silkworm silk yarn with 0 twists per inch (i.e., parallel) and (i) temperature and (ii) time. Repeat samples were processed two years after initial samples with no significant change in properties. N = 5 for all samples.

| Yarn | # of fibers | Temp | Time | UTS (N) | stdev | Stiff (N/mm) | stdev | UTS/ fiber (N) | Stiffness/ fiber (N/mm) |
|---|---|---|---|---|---|---|---|---|---|
| 9(12s) × 3(6z) | 27 | non-extracted | | 24.69 | 0.65 | 9.08 | 0.56 | 0.91 | 0.34 |
| 9(12s) × 3(6z) | 27 | 90 C. | 60 min | 21.80 | 0.47 | 7.48 | 0.97 | 0.81 | 0.28 |

TABLE 2

Mass loss as a function of sericin extraction. +/−0.43% standard deviation of an N = 5, reflects the greatest accuracy that can be achieved when confirming sericin removal, i.e., 0.87 or 1% error will always be inherent to the methods used and a mass loss of about 24% represents substantially sericin free constructs.

| yarn | non-extracted and dried (mg) | extracted and dried (mg) | % mass loss |
|---|---|---|---|
| 9(12) × 3(6) | 57.6 | 43.6 | 24.31 |
| 9(12) × 3(6) | 58.3 | 43.9 | 24.70 |
| 9(12) × 3(6) | 57.0 | 42.9 | 24.74 |
| 9(12) × 3(6) | 57.2 | 42.7 | 25.35 |
| average | 57.53 | 43.28 | 24.77 |
| stdev | 0.57 | 0.57 | 0.43 |

TABLE 3

Illustrates the change in mass as a function of a second sericin extraction. Correlated to FIG. 1E-1G, less than a 3% mass loss is likely indicative of fibroin mass loss due to mechanical damage during the 2$^{nd}$ extraction.

| yarn | mass after 1x extraction, dried (mg) | mass after 2x extracted, dried (mg) | % mass loss |
|---|---|---|---|
| 9(12) × 3(6) | 42.5 | 41.7 | 1.88 |
| 9(12) × 3(6) | 43.1 | 42 | 2.55 |
| 9(12) × 3(6) | 43.1 | 42.1 | 2.32 |
| 9(12) × 3(6) | 42.5 | 41.7 | 1.88 |
| 9(12) × 3(6) | 42.6 | 42.4 | 0.47 |
| 9(12) × 3(6) | 43.7 | 42.4 | 2.97 |
| 9(12) × 3(6) | 43.4 | 42.9 | 1.15 |
| 9(12) × 3(6) | 43.7 | 43.1 | 1.37 |
| 9(12) × 3(6) | 44 | 43.2 | 1.82 |
| average | 43.18 | 42.39 | 1.82 |
| stdev | 0.56 | 0.57 | 0.76 |

TABLE 4

| Geometry | Ply Method | Condition | # of levels of plying | Total # of Fibers | UTS average (N) | UTS stdev (N) | % Elong average | % Elong stdev | Stiffness avg (N/mm) | Stiffness stdev (N/mm) | UTS per fiber | Stiffness per fiber |
|---|---|---|---|---|---|---|---|---|---|---|---|---|
| 1(0) × 3(10) | cable | extracted | 2 | 3 | 1.98 | 0.05 | 10.42 | 1.63 | 2.17 | 0.51 | 0.66 | 0.72 |
| 1(0) × 4(10) | cable | extracted | 2 | 4 | 2.86 | 0.14 | 11.98 | 1.54 | 2.08 | 0.31 | 0.72 | 0.52 |
| 3(0) × 3(3) | cable | extracted | 2 | 9 | 6.72 | 0.17 | 12.30 | 0.72 | 4.54 | 0.16 | 0.75 | 0.50 |
| 1(0) × 3(10) × 3(9) | cable | extracted | 3 | 9 | 6.86 | 0.23 | 13.11 | 1.45 | 4.06 | 0.36 | 0.76 | 0.45 |
| 2(0) × 6(11) | cable | | 2 | 12 | 7.97 | 0.26 | 10.05 | 0.91 | | | 0.66 | |
| 4(6) × 3(3) | twist | non-extracted | 2 | 12 | 10.17 | 0.18 | 19.86 | 1.16 | | | 0.85 | |
| 1(0) × 3(10) × 4(9) | cable | extracted | 3 | 12 | 9.29 | 0.19 | 14.07 | 0.98 | 5.10 | 0.31 | 0.77 | 0.43 |
| 1(0) × 4(11) × 3(11) | twist | extracted | 3 | 12 | 9.70 | 0.14 | 12.56 | 1.03 | 7.60 | 0.33 | 0.81 | 0.63 |
| 1(0) × 4(10) × 3(9) | cable | extracted | 3 | 12 | 8.78 | 0.17 | 14.25 | 1.09 | 5.10 | 0.32 | 0.73 | 0.43 |
| 15 (textured) | textured | non-extracted, dry | 1 | 15 | 10.62 | 0.68 | 10.76 | 1.70 | 4.75 | 0.30 | 0.71 | 0.316 |
| 30(0) | parallel | extracted, wet | 1 | 30 | 20.24 | 1.46 | 26.32 | 3.51 | 1.14 | 0.15 | 0.67 | 0.038 |
| 30(0) | parallel | incubated 21 days, wet | 1 | 30 | 19.73 | 2.10 | 20.70 | 6.03 | | | 0.66 | |
| 30(0) | parallel | cell-seeded 21 days, wet | 1 | 30 | 20.53 | 1.02 | 29.68 | 7.08 | | | 0.68 | |
| 2 fibers/carrier in an 8 | braid | extracted, dry | 2 | 16 | 10.93 | 0.13 | | | 6.96 | 1.14 | 0.68 | 0.435 |
| 4 fibers/carrier in an 8 | braid | extracted, dry | 2 | 32 | 24.60 | 0.22 | | | 12.39 | 0.53 | 0.77 | 0.387 |
| 4(6) × 3(3) in 4 carrier | braid | extracted, dry | 3 | 48 | 37.67 | 0.18 | 22.38 | 0.98 | | | 0.78 | |
| 15(0) × 3(12) | cable | dry | 2 | 45 | 27.39 | 0.62 | 31.68 | 1.35 | 4.63 | 0.49 | 0.61 | 0.102889 |
| 15(0) × 3(12) × 3(10) | cable | non-extracted, 1 | 3 | 135 | 73.61 | 6.00 | 33.72 | 5.67 | 12.33 | 1.53 | 0.55 | 0.091333 |

TABLE 4-continued

| Geometry | Ply Method | Condition | # of levels of plying | Total # of Fibers | UTS average (N) | UTS stdev (N) | % Elong average | % Elong stdev | Stiffness avg (N/mm) | Stiffness stdev (N/mm) | UTS per fiber | Stiffness per fiber |
|---|---|---|---|---|---|---|---|---|---|---|---|---|
| 15(0) × 3(12) × 3(10) | cable | day after manufacturing non-extracted, 2 days after manufacturing | 3 | 135 | 72.30 | 5.68 | 31.18 | 4.35 | | | 0.54 | |
| 15(0) × 3(12) × 3(10) | cable | non-extracted, 3 days after manufacturing | 3 | 135 | 70.74 | 2.97 | 29.50 | 4.47 | | | 0.52 | |
| 15(0) × 3(12) × 3(10) | cable | non-extracted, 4 day after manufacturing | 3 | 135 | 75.90 | 1.57 | 34.57 | 4.12 | | | 0.56 | |
| 15(0) × 3(12) × 3(10) | cable | non-extracted, 5 days after manufacturing | 3 | 135 | 71.91 | 5.71 | 36.72 | 3.75 | | | 0.53 | |
| 15(0) × 3(12) × 3(10) | cable | non-extracted, 6 days after manufacturing | 3 | 135 | 74.57 | 1.45 | 37.67 | 4.27 | | | 0.55 | |
| 13(0) × 3(11) × 3(10) × 3(0) | cable | non-extracted, dry | 4 | 351 | 189.01 | 14.00 | 45.87 | 3.72 | | | 0.54 | |
| 13(0) × 3(11) × 3(10) × 3(0) | cable | non-extracted, cycled 30x to pretension, dry | 4 | 351 | 170.12 | 7.37 | 39.95 | 1.37 | | | 0.48 | |

TABLE 5

Comparison of UTS and stiffness between wet (2 hr incubation in PBS at 37° C.) and dry mechanical testing conditions. N = 5. Results show approximately a 17% drop in UTS as a function of testing wet.

| Yarn | # of Fibers | Yarn Test Conditions | UTS (N) | UTS stdev | Stiffness (N/mm) | Stiffness stdev | UTS/fiber (N) | Stiffness/fiber (N/mm) |
|---|---|---|---|---|---|---|---|---|
| 9(12s) × 3(9z) | 27 | extracted - dry | 21.88 | 0.18 | 7.38 | 0.34 | 0.81 | 0.27 |
| 9(12s) × 3(9z) | 27 | extracted - wet | 18.52 | 0.25 | 2.56 | 0.31 | 0.69 | 0.09 |
| 9(6s) × 3(3z) | 27 | extracted - dry | 21.36 | 0.40 | 7.95 | 1.00 | 0.79 | 0.29 |
| 9(6s) × 3(3z) | 27 | extracted - wet | 17.94 | 0.30 | 2.40 | 0.28 | 0.66 | 0.09 |
| 9(12s) × 3(6z) | 27 | extracted - dry | 21.80 | 0.47 | 7.48 | 0.97 | 0.81 | 0.28 |
| 9(12s) × 3(6z) | 27 | extracted - wet | 18.74 | 0.22 | 2.57 | 0.11 | 0.69 | 0.10 |
| 12(0) × 3(10s) | 36 | extracted - dry | 30.73 | 0.46 | 16.24 | 0.66 | 0.85 | 0.45 |
| 12(0) × 3(10s) | 36 | extracted - wet | 25.93 | 0.29 | 6.68 | 0.70 | 0.72 | 0.19 |
| 4(0) × 3(10s) × 3(9z) | 36 | extracted - dry | 30.07 | 0.35 | 15.49 | 1.06 | 0.84 | 0.43 |
| 4(0) × 3(10s) × 3(9z) | 36 | extracted - wet | 22.55 | 0.66 | 7.63 | 1.00 | 0.63 | 0.21 |

TABLE 6

Effect of TPI on UTS and Stiffness. N = 5

| Yarn | TPI | UTS (N) | stdev | Stiffness (N/mm) | stdev | UTS/fiber (N) | Stiffness/fiber (N/mm) |
|---|---|---|---|---|---|---|---|
| 12(0) × 3(2) | 2 | 23.27 | 0.28 | 6.86 | 0.60 | 0.65 | 0.19 |
| 12(0) × 3(4) | 4 | 24.69 | 0.31 | 7.61 | 1.17 | 0.69 | 0.21 |
| 12(0) × 3(6) | 6 | 25.44 | 0.42 | 6.51 | 1.35 | 0.71 | 0.18 |
| 12(0) × 3(8) | 8 | 25.21 | 0.23 | 5.80 | 0.67 | 0.70 | 0.16 |
| 12(0) × 3(10) | 10 | 25.94 | 0.24 | 6.45 | 0.77 | 0.72 | 0.18 |
| 12(0) × 3(12) | 12 | 25.87 | 0.19 | 6.01 | 0.69 | 0.72 | 0.17 |
| 12(0) × 3(14) | 14 | 22.21 | 0.58 | 5.63 | 0.71 | 0.62 | 0.16 |

TABLE 7

Additional tpi data to verify that up to 30 tpi can be used without causing damage to the yarn that would result in a dramatic decrease in UTS and stiffness; note, all matrices (N = 5 per group) were twisted.

| Yarn | # of fibers | UTS (N) | stdev (N) | Stiffness (N/mm) | stdev (N/mm) | UTS/ fiber (N) | Stiffness/ fiber (N/mm) | Conditions |
|---|---|---|---|---|---|---|---|---|
| 1(30) × 6(20) × 3(4.5) | 18 | 10.92 | 0.44 | 1.21 | 0.02 | 0.61 | 0.07 | non-extracted, wet |
| 1(30) × 6(20) × 3(10) | 18 | 11.48 | 0.37 | 1.25 | 0.06 | 0.64 | 0.07 | non-extracted, wet |
| 1(30) × 6(6) | 6 | 3.83 | 0.24 | 0.37 | 0.04 | 0.64 | 0.06 | non-extracted, wet |
| 15(20) | 15 | 13.19 | 0.27 | 6.03 | 0.67 | 0.88 | 0.40 | extracted, dry |

TABLE 8

Effect of yarn hierarchy on mechanical properties (i.e. the number of levels and the number of fibers per level can significantly influence yarn and fabric outcomes.

| Geometry | Condition | # of levels of plying | Total # of Fibers | UTS (N) | UTS stdev (N) | % Elong average | % Elong stdev | Stiffness avg (N/mm) | Stiffness stdev (N/mm) | UTS per fiber | Stiffness per fiber |
|---|---|---|---|---|---|---|---|---|---|---|---|
| 1(0) × 3(10) | extracted | 2 | 3 | 1.98 | 0.05 | 10.42 | 1.63 | 2.17 | 0.51 | 0.66 | 0.72 |
| 1(0) × 3(10) × 3(9) | extracted | 3 | 9 | 6.86 | 0.23 | 13.11 | 1.45 | 4.06 | 0.36 | 0.76 | 0.45 |
| 1(0) × 3(10) × 4(9) | extracted | 3 | 12 | 9.29 | 0.19 | 14.07 | 0.98 | 5.10 | 0.31 | 0.77 | 0.43 |
| 1(0) × 4(10) | extracted | 2 | 4 | 2.86 | 0.14 | 11.98 | 1.54 | 2.08 | 0.31 | 0.72 | 0.52 |
| 1(0) × 4(10) × 3(9) | extracted | 3 | 12 | 8.78 | 0.17 | 14.25 | 1.09 | 5.10 | 0.32 | 0.73 | 0.43 |
| 15(0) × 3(12) | non-extracted dry | 2 | 45 | 27.39 | 0.62 | 31.68 | 1.35 | 4.63 | 0.49 | 0.61 | 0.10 |
| 15(0) × 3(12) × 3(10) | non-extracted dry | 3 | 135 | 73.61 | 6.00 | 33.72 | 5.67 | 12.33 | 1.53 | 0.55 | 0.09 |

TABLE 9

Surface modification (RGD and ETO gas sterilization) effects on extracted silk matrix mechanical properties; PBS was used as a negative control during modification treatments.

| Yarn | # of fibers | Surface Modification/ Sterilization | UTS (N) | stdev | Stiffness (N/mm) | stdev | UTS/ fiber (N) | Stiffness/ fiber (N/mm) |
|---|---|---|---|---|---|---|---|---|
| 12(0) × 3(10s) | 36 | Non-treated | 25.94 | 0.24 | 6.45 | 0.77 | 0.72 | 0.18 |
| 12(0) × 3(10s) | 36 | RGD | 23.82 | 2.10 | 3.79 | 2.06 | 0.66 | 0.11 |
| 12(0) × 3(10s) × 3(9z) | 108 | Non-treated | 48.89 | 4.84 | 9.22 | 0.84 | 0.45 | 0.09 |
| 12(0) × 3(10s) × 3(9z) | 108 | RGD | 55.28 | 3.28 | 8.17 | 0.81 | 0.51 | 0.08 |
| 4(11s) × 3(11z) × 3(10s) | 36 | ETO | 18.72 | 0.45 | 5.52 | 0.42 | 0.52 | 0.15 |
| 4(11s) × 3(11z) × 3(10s) | 36 | RGD + ETO | 19.30 | 0.62 | 4.67 | 0.3 | 0.54 | 0.13 |

TABLE 10

| | UTS (N) | Stiffness (N/mm) | Yield Pt. (N) | Elongation (%) |
|---|---|---|---|---|
| Silk matrix 1 | 2337 +/− 72 | 354 +/− 26 | 1262 +/− 36 | 38.6 +/− 2.4 |
| Silk Matrix 2 | 3407 +/− 63 | 580 +/− 40 | 1647 +/− 214 | 29 +/− 4 |
| Human ACL | 2160 +/− 157 | 242 +/− 28 | ~1200 | ~26-32% |

Mechanical properties for two different cords based on a cord length of 3 cm as compared to human ACL properties.

TABLE 11

| | Twisting Level (# of twists/cm) | | | | | | |
|---|---|---|---|---|---|---|---|
| | Matrix 1 | Matrix 2 | Matrix 3 | Matrix 4 | Matrix 5 | Matrix 6 | Matrix 7 |
| # fibers per group | 30 (0) | 15 (0) | 1300 (0) | 180 (0) | 20 (0) | 10 (0) | 15 (0) |
| # groups per bundle | 6 (3) | 3 (3) | 3 (2) | 3 (3.5) | 6 (3) | 6 (3) | 3 (3) |
| # bundles per strand | 3 (3) | 6 (2.5) | 1 (0) | 3 (2) | 3 (2) | 3 (2.5) | 3 (2.5) |
| # strands per cord | 6 (0) | 3 (2.0) | — | 2 (0) | 3 (1) | 3 (2) | 3 (2) |

TABLE 11-continued

| | Twisting Level (# of twists/cm) | | | | | | |
|---|---|---|---|---|---|---|---|
| | Matrix 1 | Matrix 2 | Matrix 3 | Matrix 4 | Matrix 5 | Matrix 6 | Matrix 7 |
| # cords per ACL | — | 6 (0) | — | — | 3 (0) | 6 (0) | 12 (0) |
| UTS (N) | 2337 | 3407 | 2780 | 2300 | 2500 | 2300 | 3400 |
| Stiffness (N/mm) | 354 | 580 | 300 | 350 | 550 | 500 | 550 |

Examples of several geometry hierarchies that would result in suitable mechanical properties for replacement of the ACL.
Note:
Matrix 1 and 2 have been developed as shown in the examples; Matrix 3 would yield a single bundle prosthesis, Matrix 4 would yield a 2 strand prosthesis, Matrix 5 would yield a 3 cord prosthesis, Matrix 6 is another variation of a 6 cord prosthesis, and Matrix 7 will yield a 12 cord prosthesis.

We claim:

1. A method for facilitating tissue generation comprising the step of implanting a biodegradable silk fabric into the individual, wherein:
    (a) the biodegradable silk fabric is comprised of one or more individual yarns comprised of silkworm derived, sericin-extracted silk fibroin fibers, and;
    (b) the silk fibroin fibers have not been dissolved and reconstituted.

2. The method of claim 1, wherein the fabric is implanted intramuscularly.

3. The method of claim 1, wherein the fabric is implanted into an individual to replace or repair damaged tissue.

4. The method of claim 1, wherein the fabric is implanted subcutaneously.

5. The method of claim 1, wherein the fabric has one or more biomechanical properties of a connective tissue.

6. A method for facilitating tissue generation comprising the step of subcutaneously implanting in an individual a biodegradable silk fabric that has one or more biomechanical properties of a connective tissue into the individual, wherein:
    (a) the biodegradable silk fabric is comprised of one or more individual yarns comprised of silkworm derived, sericin extracted silk fibroin fibers, and;
    (b) the silk fibroin fibers have not been dissolved and reconstituted, and wherein the fabric is implanted into the individual to replace or repair damaged tissue.

* * * * *

UNITED STATES PATENT AND TRADEMARK OFFICE
CERTIFICATE OF CORRECTION

PATENT NO. : 9,089,501 B2  
APPLICATION NO. : 14/137712  
DATED : July 28, 2015  
INVENTOR(S) : Gregory H. Altman et al.

Page 1 of 1

It is certified that error appears in the above-identified patent and that said Letters Patent is hereby corrected as shown below:

On Sheet 5 of 23, in Figure 3D, Y-axis, line 1, delete "LOAD" and insert -- LOAD (N) --, therefor.

On Sheet 13 of 23, in Figure 11A, line 3, delete "PROTEALYTIC" and insert -- PROTEOLYTIC --, therefor.

In column 11, line 59, delete "staining" and insert -- staining. --, therefor.

In column 28, line 36, delete "Ligaments" and insert -- Ligaments: --, therefor.

In column 34, line 31, delete "cm2" and insert -- $cm^2$ --, therefor.

Signed and Sealed this  
Twenty-eighth Day of June, 2016

Michelle K. Lee  
*Director of the United States Patent and Trademark Office*